(12) United States Patent
Golde et al.

(10) Patent No.: US 11,345,738 B2
(45) Date of Patent: May 31, 2022

(54) COMPOUNDS FOR TREATING NEURODEGENERATIVE PROTEINOPATHIES

(71) Applicant: University of Florida Research Foundation, Incorporated, Gainesville, FL (US)

(72) Inventors: Todd E. Golde, Gainesville, FL (US); Paramita Chakrabarty, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 165 days.

(21) Appl. No.: 16/011,728

(22) Filed: Jun. 19, 2018

(65) Prior Publication Data

US 2018/0355018 A1 Dec. 13, 2018

Related U.S. Application Data

(62) Division of application No. 14/775,302, filed as application No. PCT/US2014/029202 on Mar. 14, 2014, now Pat. No. 10,030,067.

(60) Provisional application No. 61/802,184, filed on Mar. 15, 2013.

(51) Int. Cl.
| | | |
|---|---|---|
| *C07K 14/705* | (2006.01) | |
| *A61K 38/17* | (2006.01) | |
| *A61P 25/28* | (2006.01) | |
| *A61K 38/00* | (2006.01) | |

(52) U.S. Cl.
CPC ...... *C07K 14/70596* (2013.01); *A61K 38/177* (2013.01); *C07K 14/705* (2013.01); *A61K 38/00* (2013.01); *A61P 25/28* (2018.01); *C07K 2319/30* (2013.01); *C07K 2319/31* (2013.01); *C07K 2319/32* (2013.01); *C07K 2319/40* (2013.01); *C07K 2319/43* (2013.01)

(58) Field of Classification Search
CPC ............ C07K 14/705; C07K 14/70596; C07K 2319/30–32; C07K 2319/40; C07K 2319/43; A61K 48/00; C12N 2799/022; C12N 15/861; C12N 15/8613
See application file for complete search history.

(56) References Cited

U.S. PATENT DOCUMENTS

| | | | |
|---|---|---|---|
| 10,030,067 B2 | 7/2018 | Golde et al. | |
| 2007/0275416 A1 | 11/2007 | Gloeckner et al. | |
| 2009/0208501 A1 | 8/2009 | Visintin et al. | |
| 2010/0092462 A1* | 4/2010 | Jordan | A61K 38/177 424/130.1 |

FOREIGN PATENT DOCUMENTS

| | | | | |
|---|---|---|---|---|
| AU | 2010212293 B2 * | 7/2012 | ............. | C12N 15/86 |
| JP | 2008-538498 A | 10/2008 | | |
| WO | WO-03020760 A1 * | 3/2003 | ......... | A61K 38/1709 |
| WO | WO 2006/111946 A2 | 10/2006 | | |
| WO | WO 2009/000929 A2 | 12/2008 | | |
| WO | WO-2009090493 A2 * | 7/2009 | ........... | C07K 14/705 |
| WO | WO-2010031801 A2 * | 3/2010 | ......... | A61K 38/1709 |
| WO | WO 2012/016973 A1 | 2/2012 | | |
| WO | WO 2013/004607 A1 | 1/2013 | | |

OTHER PUBLICATIONS

Botos I et al. The structural biology of Toll-Like Receptors. Structure, 19(4): 447-459. (Year: 2011).*
Hanamsagar R et al. Toll-like receptor (TLR) and inflammasome actions in the central nervous system. Trends Immunology, 33(7): 333-342. (Year: 2012).*
Trudler D et al. Toll-like receptor expression and signaling in glia cells in neuro-amyloidogenic diseases: Towards future therapeutic application. Mediators of Inflammation, Article ID 497987, 12 pages. (Year: 2010).*
Walter S et al. Role of the Toll-like receptor 4 in neuroinflammation in Alzheimer's disease. Cell Physiol Biochem. 2007, 20:947-956. (Year: 2007).*
Amor et al. Immunology, 2010, 129: 154-169. (Year: 2010).*
Beraud et al. Parkinsonism Relat Disord. Jan. 2012, 18(0 1): S17-S20. (Year: 2012).*
Carvalho et al. Mucosal Immunol. 4(1): 102-111. (Year: 2011).*
Fellner et al. Glia, 2013, 61: 349-360. (Year: 2013).*
Lee et al. Neuropathol. Appl. Neurobiol. 2013, 39: 69-85. (Year: 2013).*
Stefanova et al. Am. J. Pathol. 2011. 179(2): 954-963. (Year: 2011).*
International Preliminary Report on Patentability dated Sep. 24, 2015 in connection with International Application No. PCT/US2014/02902.
International Search Report and Written Opinion dated Jul. 17, 2014 in connection with International Application No. PCT/US2014/029202.
Extended European Search Report for EP 14764448.8 dated Jul. 28, 2016.
Alzforum, Innate immune cells enlisted to clear amyloid, fight disease. SERIES: Society for Neuroscience (SfN) Annual Meeting 2013 (Epub Dec. 5, 2013). (Web address: www.alzforum.org/news/conference-coverage/innate-immune-cells-enlisted-clear-amyloid-fight-disease). Last accessed May 12, 2014. 8 Pages.
Brandl et al., A designed TLR4/MD-2 complex to capture LPS. J Endotoxin Res. 2005;11(4):197-206. Erratum in J Endotoxin Res. Aug. 2012;18(4):672.

(Continued)

*Primary Examiner* — Kimberly Ballard
(74) *Attorney, Agent, or Firm* — Wolf, Greenfield & Sacks, P.C.

(57) ABSTRACT

This invention relates to compounds (e.g., those delineated herein), pharmaceutically acceptable salts, prodrugs, solveates, and hydrates thereof. This invention also provides compositions comprising a compound of this invention and the use of such compounds and compositions in methods of treating diseases and conditions that are beneficially treated by administering modulating compounds or compositions that modulate Aβ, PAMPS and DAMPS.

16 Claims, 45 Drawing Sheets
Specification includes a Sequence Listing.

(56) References Cited

OTHER PUBLICATIONS

Carty et al., Evaluating the role of Toll-like receptors in diseases of the central nervous system. Biochem Pharmacol. Apr. 1, 2011;81(7):825-37. doi: 10.1016/j.bcp.2011.01.003. Epub Jan. 15, 2011.

Chakrabarty, Alzheimer's disease expressing engineered receptor domains to treat Alzheimer's disease soluble Toll-like receptors: potential anti amyloid beta agents; Bright Focus Foundation, Jul. 7, 2011. Retrieved from the internet: www.brightfocus.org/alzheimers/grant/soluble-toll-receptors-potential-anti-amyloid-beta-agents . Last accessed Jul. 11, 2016. 3 Pages.

Einhauer et al., The FLAG peptide, a versatile fusion tag for the purification of recombinant proteins. J Biochem Biophys Methods. Oct. 30, 2001;49(1-3):455-65.

Glass et al. Mechanisms underlying inflammation in Neurodegeneration. Cell. Mar. 19, 2010;140 (6):918-34.

Gloeckner et al., A novel tandem affinity purification strategy for the efficient isolation and characterisation of native protein complexes. Proteomics. Dec. 2007;7(23):4228-34.

Groβ et al., Lipopolysaccharide-trap-Fc, a Multifunctional Agent To Battle Gram-Negative Bacteria. Infection and Immunity. Jul. 2009; 77(7):2925-31.

Jung et al., Toll-like receptor 4 decoy, TOY, attenuates gram-negative bacterial sepsis. PLoS One. Oct. 9, 2009;4(10):e7403. doi: 10.1371/journal.pone.0007403.

LeBouder et al., Soluble forms of Toll-like receptor (TLR)2 capable of modulating TLR2 signaling are present in human plasma and breast milk. J Immunol. Dec. 15, 2003;171(12):6680-9.

Li, Commonly used tag combinations for tandem affinity purification. Biotechnol Appl Biochem. Feb. 15, 2010;55(2):73-83. doi: 10.1042/BA20090273.

Liew et al., Negative regulation of toll-like receptor-mediated immune responses. Nat Rev Immunol. Jun. 2005;5(6):446-58.

Liu et al., TLR2 is a primary receptor for Alzheimer's amyloid β peptide to trigger neuroinflammatory activation. J Immunol. Feb. 1, 2012;188(3):1098-107. doi: 10.4049/jimmunol.1101121. Epub Dec. 23, 2011.

Mizel et al., Identification of a sequence in human toll-like receptor 5 required for the binding of Gram-negative flagellin. J Biol Chem. Jun. 27, 2003;278(26):23624-9. Epub Apr. 23, 2003.

Raby et al., Soluble TLR2 reduces inflammation without compromising bacterial clearance by disrupting TLR2 triggering. J Immunol. Jul. 1, 2009;183(1):506-17. doi: 10.4049/jimmunol.0802909.

Re et al., Monomeric Recombinant MD-2 Binds Toll-Like Receptor 4 Tightly and Confers Lipopolysaccharide Responsiveness. Journal of Biological Chemistry. 2002; 277(26):23427-32 Epub Apr. 25, 2002.

Tsujita et al., Fish soluble Toll-like receptor (TLR)5 amplifies human TLR5 response via physical binding to flagellin. Vaccine. Mar. 15, 2006;24(12):2193-9. Epub Nov. 14, 2005.

Visintin et al., Pharmacological inhibition of endotoxin responses is achieved by targeting the TLR4 coreceptor, MD-2. J Immunol. Nov. 15, 2005;175(10):6465-72.

Walter et al., Role of the toll-like receptor 4 in neuroinflammation in Alzheimer's disease. Cell Physiol Biochem. 2007;20(6):947-56.

Zhou et al., Toll-like receptor 5 forms asymmetric dimers in the absence of flagellin. J Struct Biol. Feb. 2012;177(2):402-9. doi: 10.1016/j.jsb.2011.12.002. Epub Dec. 8, 2011.

Zunt et al., Soluble forms of Toll-like receptor 4 are present in human saliva and modulate tumour necrosis factor-alpha secretion by macrophage-like cells. Clin Exp Immunol. May 2009;156(2):285-93. doi: 10.1111/j.1365-2249.2009.03854.x. Epub Mar. 9, 2009.

Fiala et al., Innate immunity and transcription of MGAT-III and Toll-like receptors in Alzheimer's disease patients are improved by bisdemethoxycurcumin. Proc Natl Acad Sci U S A. Jul. 31, 2007;104(31): 12849-54. Epub Jul. 24, 2007.

Frank et al., Differential regulation of toll-like receptor mRNAs in amyloid plaque-associated brain tissue of aged APP23 transgenic mice. Neurosci Lett. Mar. 27, 2009;453(1):41-4. doi: 10.1016/j.neulet.2009.01.075. Epub Feb. 4, 2009.

Müller et al., Activity of soluble OX40 ligand is enhanced by oligomerization and cell surface immobilization. FEBS J. May 2008;275(9):2296-304. doi: 10.1111/j.1742-4658.2008.06382.x. Epub Apr. 3, 2008.

Tsoi et al., Identification of a transcript encoding a soluble form of toll-like receptor 5 (TLR5) in Atlantic salmon during Aeromonas salmonicida infection. Vet Immunol Immunopathol. Jan. 15, 2006;109(1-2):183-7. Epub Aug. 19, 2005.

Wyzgol et al., Trimer stabilization, oligomerization, and antibody-mediated cell surface immobilization improve the activity of soluble trimers of CD27L, CD40L, 41 BBL, and glucocorticoid-induced TNF receptor ligand. J Immunol. Aug. 1, 2009;183(3):1851-61. doi: 10.4049/jimmunol.0802597. Epub Jul. 13, 2009.

* cited by examiner

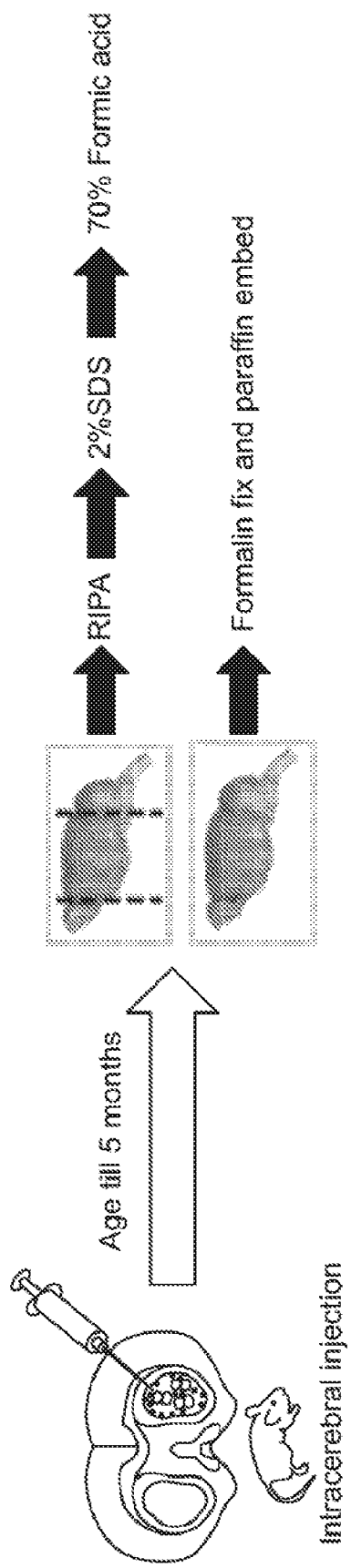

FIG. 3A

Engineered Soluble TLRs:

Please refer to Table 3 for a summary of the constructs used in the assays.

```
Mouse sequences:
Mouse soluble TLR2
ATGCCACATACTTTGTGGATGGTGTGGGTCTTGGGGGTCATCATCAGCCTCTCCAAGGAA
GAATCCTCCAATCAGGCTTCTCTGTCTTGTGACCGCAATGGTATCTGCAAGGGCAGCTCA
GGATCTTTAAACTCCATTCCCTCAGGGCTCACAGAAGCTGTAAAAAGCCTTGACCTGTCC
AACAACAGGATCACCTACATTAGCAACAGTGACCTACAGAGGTGTGTGAACCTCCAGGCT
CTGGTGCTGACATCCAATGGAATTAACACAATAGAGGAAGATTCTTTTTCTTCCCTGGGC
AGTCTTGAACATTTAGACTTATCCTATAATTACTTATCTAATTTATCGTCTTCCTGGTTC
AAGCCCCTTTCTTCTTTAACATTCTTAAACTTACTGGGAAATCCTTACAAAACCCTAGGG
GAAACATCTCTTTTTTCTCATCTCACAAAATTGCAAATCCTGAGAGTGGGAAATATGGAC
ACCTTCACTAAGATTCAAAGAAAAGATTTTGCTGGACTTACCTTCCTTGAGGAACTTGAG
ATTGATGCTTCAGATCTACAGAGCTATGAGCCAAAAAGTTTGAAGTCAATTCAGAACGTA
AGTCATCTGATCCTTCATATGAAGCAGCATATTTTACTGCTGGAGATTTTTGTAGATGTT
ACAAGTTCCGTGGAATGTTTGGAACTGCGAGATACTGATTTGGACACTTTCCATTTTTCA
GAACTATCCACTGGTGAAACAAATTCATTGATTAAAAAGTTTACATTTAGAAATGTGAAA
ATCACCGATGAAAGTTTGTTTCAGGTTATGAAACTTTTGAATCAGATTTCTGGATTGTTA
GAATTAGAGTTTGATGACTGTACCCTTAATGGAGTTGGTAATTTTAGAGCATCTGATAAT
GACAGAGTTATAGATCCAGGTAAAGTGGAAACGTTAACAATCCGGAGGCTGCATATTCCA
AGGTTTTACTTATTTTATGATCTGAGCACTTTATATTCACTTACAGAAAGAGTTAAAAGA
ATCACAGTAGAAAACAGTAAAGTTTTTCTGGTTCCTTGTTTACTTTCACAACATTTAAAA
TCATTAGAATACTTGGATCTCAGTGAAAATTTGATGGTTGAAGAATACTTGAAAAATTCA
GCCTGTGAGGATGCCTGGCCCTCTCTACAAACTTTAATTTTAAGGCAAAATCATTTGGCA
TCATTGGAAAAAACCGGAGAGACTTTGCTCACTCTGAAAAACTTGACTAACATTGATATC
AGTAAGAATAGTTTTCATTCTATGCCTGAAACTTGTCAGTGGCCAGAAAAGATGAAATAT
TTGAACTTATCCAGCACACGAATACACAGTGTAACAGGCTGCATTCCCAAGACACTGGAA
ATTTTAGATGTTAGCAACAACAATCTCAATTTATTTTCTTTGAATTTGCCGCAACTCAAA
GAACTTTATATTTCCAGAAATAAGTTGATGACTCTACCAGATGCCTCCCTCTTACCCATG
TTACTAGTATTGAAAATCAGTAGGAATGCAATAACTACGTTTTCTAAGGAGCAACTTGAC
TCATTTCACACACTGAAGACTTTGGAAGCTGGTGGCAATAACTTCATTTGCTCCTGTGAA
TTCCTCTCCTTCACTCAGGAGCAGCAAGCACTGGCCAAAGTCTTGATTGATTGGCCAGCA
AATTACCTGTGTGACTCTCCATCCCATGTGCGTGGCCAGCAGGTTCAGGATGTCCGCCTC
TCGGTGTCGGAATGTCACAGGACAGCACTGGTGTCTGGCATGTGCTGTGCTCTGTTCCTG
```

FIG. 3B

Mouse soluble TLR4
ATGATGTCTGCCTCGCGCCTGGCTGGGACTCTGATCCCAGCCATGGCCTTCCTCTCCTGC
GTGAGACCAGAAAGCTGGGAGCCCTGCGTGGAGGTGGTTCCTAATATTACTTATCAATGC
ATGGAGCTGAATTTCTACAAAATCCCCGACAACCTCCCCTTCTCAACCAAGAACCTGGAC
CTGAGCTTTAATCCCCTGAGGCATTTAGGCAGCTATAGCTTCTTCAGTTTCCCAGAACTG
CAGGTGCTGGATTTATCCAGGTGTGAAATCCAGACAATTGAAGATGGGGCATATCAGAGC
CTAAGCCACCTCTCTACCTTAATATTGACAGGAAACCCCATCCAGAGTTTAGCCCTGGGA
GCCTTTTCTGGACTATCAAGTTTACAGAAGCTGGTGGCTGTGGAGACAAATCTAGCATCT
CTAGAGAACTTCCCCATTGGACATCTCAAAACTTTGAAAGAACTTAATGTGGCTCACAAT
CTTATCCAATCTTTCAAATTACCTGAGTATTTTCTAATCTGACCAATCTAGAGCACTTG
GACCTTCCAGCAACAAGATTCAAAGTATTTATTGCACAGACTTGCGGGTTCTACATCAA
ATGCCCCTACTCAATCTCTCTTTAGACCTGTCCCTGAACCCTATGAACTTTATCCAACCA
GGTGCATTTAAAGAAATTAGGCTTCATAAGCTGACTTTAAGAAATAATTTTGATAGTTTA
AATGTAATGAAAACTTGTATTCAAGGTCTGGCTGGTTTAGAAGTCCATCGTTTGGTTCTG
GGAGAATTTAGAAATGAAGGAAACTTGGAAAAGTTTGACAAATCTGCTCTAGAGGGCCTG
TGCAATTTGACCATTGAAGAATTCCGATTAGCATACTTAGACTACTACCTCGATGATATT
ATTGACTTATTTAATTGTTTGACAAATGTTTCTTCATTTTCCCTGGTGAGTGTGACTATT
GAAAGGGTAAAAGACTTTTCTTATAATTTCGGATGGCAACATTTAGAATTAGTTAACTGT
AAATTTGGACAGTTTCCCACATTGAAACTCAAATCTCTCAAAAGGCTTACTTTCACTTCC
AACAAAGGTGGGAATGCTTTTTCAGAAGTTGATCTACCAAGCCTTGAGTTTCTAGATCTC
AGTAGAAATGGCTTGAGTTTCAAAGGTTGCTGTTCTCAAAGTGATTTTGGGACAACCAGC
CTAAAGTATTTAGATCTGAGCTTCAATGGTGTTATTACCATGAGTTCAAACTTCTTGGGC
TTAGAACAACTAGAACATCTGGATTTCCAGCATTCCAATTTGAAACAAATGAGTGAGTTT
TCAGTATTCCTATCACTCAGAAACCTCATTTACCTTGACATTTCTCATACTCACACCAGA
GTTGCTTTCAATGGCATCTTCAATGGCTTGTCCAGTCTCGAAGTCTTGAAAATGGCTGGC
AATTCTTTCCAGGAAAACTTCCTTCCAGATATCTTCACAGAGCTGAGAAACTTGACCTTC
CTGGACCTCTCTCAGTGTCAACTGGAGCAGTTGTCTCCAACAGCATTTAACTCACTCTCC
AGTCTTCAGGTACTAAATATGAGCCACAACAACTTCTTTTCATTGGATACGTTTCCTTAT
AAGTGTCTGAACTCCCTCCAGGTTCTTGATTACAGTCTCAATCACATAATGACTTCCAAA
AAACAGGAACTACAGCATTTTCCAAGTAGTCTAGCTTTCTTAAATCTTACTCAGAATGAC
TTTGCTTGTACTTGTGAACACCAGAGTTTCCTGCAATGGATCAAGGACCAGAGGCAGCTC
TTGGTGGAAGTTGAACGAATGGAATGTGCAACACCTTCAGATAAGCAGGGCATGCCTGTG
CTGAGTTTGAATATCACCTGTCAGATGAATAAG

FIG. 3C

Mouse soluble TLR5
ATGGGAGACCACCTGGACCTTCTCCTAGGAGTGGTGCTCATGGCCGGTCCTGTGTTTGGA
ATTCCTTCCTGCTCCTTTGATGGCCGAATAGCCTTTTATCGTTTCTGCAACCTCACCCAG
GTCCCCCAGGTCCTCAACACCACTGAGAGGCTCCTGCTGAGCTTCAACTATATCAGGACA
GTCACTGCTTCATCCTTCCCCTTTCTGGAACAGCTGCAGCTGCTGGAGCTCGGGAGCCAG
TATACCCCCTTGACTATTGACAAGGAGGCCTTCAGAAACCTGCCCAACCTTAGAATCTTG
GACCTGGGAAGTAGTAAGATATACTTCTTGCATCCAGATGCTTTTCAGGGACTGTTCCAT
CTGTTTGAACTTAGACTGTATTTCTGTGGTCTCTCTGATGCTGTATTGAAAGATGGTTAT
TTCAGAAATTTAAAGGCTTTAACTCGCTTGGATCTATCCAAAAATCAGATTCGTAGCCTT
TACCTTCATCCTTCATTTGGGAAGTTGAATTCCTTAAAGTCCATAGATTTTTCCTCCAAC
CAAATATTCCTTGTATGTGAACATGAGCTCGAGCCCCTACAAGGGAAAACGCTCTCCTTT
TTTAGCCTCGCAGCTAATAGCTTGTATAGCAGAGTCTCAGTGGACTGGGGAAAATGTATG
AACCCATTCAGAAACATGGTGCTGGAGATACTAGATGTTTCTGGAAATGGCTGGACAGTG
GACATCACAGGAAACTTTAGCAATGCCATCAGCAAAAGCCAGGCCTTCTCTTTGATTCTT
GCCCACCACATCATGGGTGCCGGGTTTGGCTTCCATAACATCAAAGATCCTGACCAGAAC
ACATTTGCTGGCCTGGCCAGAAGTTCAGTGAGACACCTGGATCTTTCACATGGGTTTGTC
TTCTCCCTGAACTCACGAGTCTTTGAGACACTCAAGGATTTGAAGGTTCTGAACCTTGCC
TACAACAAGATAAATAAGATTGCAGATGAAGCATTTTACGGACTTGACAACCTCCAAGTT
CTCAATTTGTCATATAACCTTCTGGGGGAACTTTACAGTTCGAATTTCTATGGACTACCT
AAGGTAGCCTACATTGATTTGCAAAAGAATCACATTGCAATAATTCAAGACCAAACATTC
AAATTCCTGGAAAAATTACGGACCTTGGATCTCCGAGACAATGCTCTTACAACCATTCAT
TTTATTCCAAGCATACCCGATATCTTCTTGAGTGGCAATAAACTAGTGACTTTGCCAAAG
ATCAACCTTACAGCGAACCTCATCCACTTATCAGAAAACAGGCTAGAAAATCTAGATATT
CTCTACTTTCTCCTACGGGTACCTCATCTCCAGATTCTCATTTTAAATCAAATCGCTTC
TCCTCCTGTAGTGGAGATCAAACCCCTTCAGAGAATCCCAGCTTAGAACAGCTTTTCCTT
GGAGAAAATATGTTGCAACTTGCCTGGGAAACTGAGCTCTGTTGGGATGTTTTTGAGGGA
CTTTCTCATCTTCAAGTTCTGTATTTGAATCATAACTATCTTAATTCCCTTCCACCAGGA
GTATTTAGCCATCTGACTGCATTAAGGGGACTAAGCCTCAACTCCAACAGGCTGACAGTT
CTTTCTCACAATGATTTACCTGCTAATTTAGAGATCCTGGACATATCCAGGAACCAGCTC
CTAGCTCCTAATCCTGATGTATTTGTATCACTTAGTGTCTTGGATATAACTCATAACAAG
TTCATTTGTGAATGTGAACTTAGCACTTTTATCAATTGGCTTAATCACACCAATGTCACT
ATAGCTGGGCCTCCTGCAGACATATATTGTGTGTACCCTGACTCGTTCTCTGGGGTTTCC
CTCTTCTCTCTTTCCACGGAAGGTTGTGATGAAGAGGAAGTCTTAAAG

FIG. 3D

Human sequences:
Human soluble TLR2
ATGCCACATACTTTGTGGATGGTGTGGGTCTTGGGGGTCATCATCAGCCTCTCCAAGGAA
GAATCCTCCAATCAGGCTTCTCTGTCTTGTGACCGCAATGGTATCTGCAAGGGCAGCTCA
GGATCTTTAAACTCCATTCCCTCAGGGCTCACAGAAGCTGTAAAAAGCCTTGACCTGTCC
AACAACAGGATCACCTACATTAGCAACAGTGACCTACAGAGGTGTGTGAACCTCCAGGCT
CTGGTGCTGACATCCAATGGAATTAACACAATAGAGGAAGATTCTTTTTCTTCCCTGGGC
AGTCTTGAACATTTAGACTTATCCTATAATTACTTATCTAATTTATCGTCTTCCTGGTTC
AAGCCCCTTTCTTCTTTAACATTCTTAAACTTACTGGGAAATCCTTACAAAACCCTAGGG
GAAACATCTCTTTTTTCTCATCTCACAAAATTGCAAATCCTGAGAGTGGGAAATATGGAC
ACCTTCACTAAGATTCAAAGAAAAGATTTTGCTGGACTTACCTTCCTTGAGGAACTTGAG
ATTGATGCTTCAGATCTACAGAGCTATGAGCCAAAAAGTTTGAAGTCAATTCAGAACGTA
AGTCATCTGATCCTTCATATGAAGCAGCATATTTTACTGCTGGAGATTTTTGTAGATGTT
ACAAGTTCCGTGGAATGTTTGGAACTGCGAGATACTGATTTGGACACTTTCCATTTTTCA
GAACTATCCACTGGTGAAACAAATTCATTGATTAAAAAGTTTACATTTAGAAATGTGAAA
ATCACCGATGAAAGTTTGTTTCAGGTTATGAAACTTTTGAATCAGATTTCTGGATTGTTA
GAATTAGAGTTTGATGACTGTACCCTTAATGGAGTTGGTAATTTTAGAGCATCTGATAAT
GACAGAGTTATAGATCCAGGTAAAGTGGAAACGTTAACAATCCGGAGGCTGCATATTCCA
AGGTTTTACTTATTTTATGATCTGAGCACTTTATATTCACTTACAGAAAGAGTTAAAAGA
ATCACAGTAGAAAACAGTAAAGTTTTTCTGGTTCCTTGTTTACTTTCACAACATTTAAAA
TCATTAGAATACTTGGATCTCAGTGAAAATTTGATGGTTGAAGAATACTTGAAAAATTCA
GCCTGTGAGGATGCCTGGCCCTCTCTACAAACTTTAATTTTAAGGCAAAATCATTTGGCA
TCATTGGAAAAAACCGGAGAGACTTTGCTCACTCTGAAAAACTTGACTAACATTGATATC
AGTAAGAATAGTTTTCATTCTATGCCTGAAACTTGTCAGTGGCCAGAAAAGATGAAATAT
TTGAACTTATCCAGCACACGAATACACAGTGTAACAGGCTGCATTCCCAAGACACTGGAA
ATTTTAGATGTTAGCAACAACAATCTCAATTTATTTTCTTTGAATTTGCCGCAACTCAAA
GAACTTTATATTTCCAGAAATAAGTTGATGACTCTACCAGATGCCTCCCTCTTACCCATG
TTACTAGTATTGAAAATCAGTAGGAATGCAATAACTACGTTTTCTAAGGAGCAACTTGAC
TCATTTCACACACTGAAGACTTTGGAAGCTGGTGGCAATAACTTCATTTGCTCCTGTGAA
TTCCTCTCCTTCACTCAGGAGCAGCAAGCACTGGCCAAAGTCTTGATTGATTGGCCAGCA
AATTACCTGTGTGACTCTCCATCCCATGTGCGTGGCCAGCAGGTTCAGGATGTCCGCCTC
TCGGTGTCGGAATGTCACAGGACA

FIG. 3E

Human soluble TLR4
ATGGAGCTGAATTTCTACAAAATCCCCGACAACCTCCCCTTCTCAACCAAGAACCTGGAC
CTGAGCTTTAATCCCCTGAGGCATTTAGGCAGCTATAGCTTCTTCAGTTTCCCAGAACTG
CAGGTGCTGGATTTATCCAGGTGTGAAATCCAGACAATTGAAGATGGGGCATATCAGAGC
CTAAGCCACCTCTCTACCTTAATATTGACAGGAAACCCCATCCAGAGTTTAGCCCTGGGA
GCCTTTTCTGGACTATCAAGTTTACAGAAGCTGGTGGCTGTGGAGACAAATCTAGCATCT
CTAGAGAACTTCCCCATTGGACATCTCAAAACTTTGAAAGAACTTAATGTGGCTCACAAT
CTTATCCAATCTTTCAAATTACCTGAGTATTTTTCTAATCTGACCAATCTAGAGCACTTG
GACCTTTCCAGCAACAAGATTCAAAGTATTTATTGCACAGACTTGCGGGTTCTACATCAA
ATGCCCCTACTCAATCTCTCTTTAGACCTGTCCCTGAACCCTATGAACTTTATCCAACCA
GGTGCATTTAAAGAAATTAGGCTTCATAAGCTGACTTTAAGAAATAATTTTGATAGTTTA
AATGTAATGAAAACTTGTATTCAAGGTCTGGCTGGTTTAGAAGTCCATCGTTTGGTTCTG
GGAGAATTTAGAAATGAAGGAAACTTGGAAAAGTTTGACAAATCTGCTCTAGAGGGCCTG
TGCAATTTGACCATTGAAGAATTCCGATTAGCATACTTAGACTACTACCTCGATGATATT
ATTGACTTATTTAATTGTTTGACAAATGTTTCTTCATTTTCCCTGGTGAGTGTGACTATT
GAAAGGGTAAAAGACTTTTCTTATAATTTCGGATGGCAACATTTAGAATTAGTTAACTGT
AAATTTGGACAGTTTCCCACATTGAAACTCAAATCTCTCAAAAGGCTTACTTTCACTTCC
AACAAAGGTGGGAATGCTTTTTCAGAAGTTGATCTACCAAGCCTTGAGTTTCTAGATCTC
AGTAGAAATGGCTTGAGTTTCAAAGGTTGCTGTTCTCAAAGTGATTTTGGGACAACCAGC
CTAAAGTATTTAGATCTGAGCTTCAATGGTGTTATTACCATGAGTTCAAACTTCTTGGGC
TTAGAACAACTAGAACATCTGGATTTCCAGCATTCCAATTTGAAACAAATGAGTGAGTTT
TCAGTATTCCTATCACTCAGAAACCTCATTTACCTTGACATTTCTCATACTCACACCAGA
GTTGCTTTCAATGGCATCTTCAATGGCTTGTCCAGTCTCGAAGTCTTGAAAATGGCTGGC
AATTCTTTCCAGGAAAACTTCCTTCCAGATATCTTCACAGAGCTGAGAAACTTGACCTTC
CTGGACCTCTCTCAGTGTCAACTGGAGCAGTTGTCTCCAACAGCATTTAACTCACTCTCC
AGTCTTCAGGTACTAAATATGAGCCACAACAACTTCTTTTCATTGGATACGTTTCCTTAT
AAGTGTCTGAACTCCCTCCAGGTTCTTGATTACAGTCTCAATCACATAATGACTTCCAAA
AAACAGGAACTACAGCATTTTCCAAGTAGTCTAGCTTTCTTAAATCTTACTCAGAATGAC
TTTGCTTGTACTTGTGAACACCAGAGTTTCCTGCAATGGATCAAGGACCAGAGGCAGCTC
TTGGTGGAAGTTGAACGAATGGAATGTGCAACACCTTCAGATAAGCAGGGCATGCCTGTG
CTGAGTTTGAATATCACCTGTCAGATGAATAAG

FIG. 3F

Human soluble TLR5
ATGGGAGACCACCTGGACCTTCTCCTAGGAGTGGTGCTCATGGCCGGTCCTGTGTTTGGA
ATTCCTTCCTGCTCCTTTGATGGCCGAATAGCCTTTTATCGTTTCTGCAACCTCACCCAG
GTCCCCAGGTCCTCAACACCACTGAGAGGCTCCTGCTGAGCTTCAACTATATCAGGACA
GTCACTGCTTCATCCTTCCCCTTTCTGGAACAGCTGCAGCTGCTGGAGCTCGGGAGCCAG
TATACCCCCTTGACTATTGACAAGGAGGCCTTCAGAAACCTGCCCAACCTTAGAATCTTG
GACCTGGGAAGTAGTAAGATATACTTCTTGCATCCAGATGCTTTTCAGGGACTGTTCCAT
CTGTTTGAACTTAGACTGTATTTCTGTGGTCTCTCTGATGCTGTATTGAAAGATGGTTAT
TTCAGAAATTTAAAGGCTTTAACTCGCTTGGATCTATCCAAAAATCAGATTCGTAGCCTT
TACCTTCATCCTTCATTTGGGAAGTTGAATTCCTTAAAGTCCATAGATTTTTCCTCCAAC
CAAATATTCCTTGTATGTGAACATGAGCTCGAGCCCCTACAAGGGAAAACGCTCTCCTTT
TTTAGCCTCGCAGCTAATAGCTTGTATAGCAGAGTCTCAGTGGACTGGGGAAAATGTATG
AACCCATTCAGAAACATGGTGCTGGAGATACTAGATGTTTCTGGAAATGGCTGGACAGTG
GACATCACAGGAAACTTTAGCAATGCCATCAGCAAAAGCCAGGCCTTCTCTTTGATTCTT
GCCCACCACATCATGGGTGCCGGGTTTGGCTTCCATAACATCAAAGATCCTGACCAGAAC
ACATTTGCTGGCCTGGCCAGAAGTTCAGTGAGACACCTGGATCTTTCACATGGGTTTGTC
TTCTCCCTGAACTCACGAGTCTTTGAGACACTCAAGGATTTGAAGGTTCTGAACCTTGCC
TACAACAAGATAAATAAGATTGCAGATGAAGCATTTTACGGACTTGACAACCTCCAAGTT
CTCAATTTGTCATATAACCTTCTGGGGGAACTTTACAGTTCGAATTTCTATGGACTACCT
AAGGTAGCCTACATTGATTTGCAAAAGAATCACATTGCAATAATTCAAGACCAAACATTC
AAATTCCTGGAAAAATTACGGACCTTGGATCTCCGAGACAATGCTCTTACAACCATTCAT
TTTATTCCAAGCATACCCGATATCTTCTTGAGTGGCAATAAACTAGTGACTTTGCCAAAG
ATCAACCTTACAGCGAACCTCATCCACTTATCAGAAAACAGGCTAGAAAATCTAGATATT
CTCTACTTTCTCCTACGGGTACCTCATCTCCAGATTCTCATTTTAAATCAAAATCGCTTC
TCCTCCTGTAGTGGAGATCAAACCCCTTCAGAGAATCCCAGCTTAGAACAGCTTTTCCTT
GGAGAAAATATGTTGCAACTTGCCTGGGAAACTGAGCTCTGTTGGGATGTTTTTGAGGGA
CTTTCTCATCTTCAAGTTCTGTATTTGAATCATAACTATCTTAATTCCCTTCCACCAGGA
GTATTTAGCCATCTGACTGCATTAAGGGGACTAAGCCTCAACTCCAACAGGCTGACAGTT
CTTTCTCACAATGATTTACCTGCTAATTTAGAGATCCTGGACATATCCAGGAACCAGCTC
CTAGCTCCTAATCCTGATGTATTTGTATCACTTAGTGTCTTGGATATAACTCATAACAAG
TTCATTTGTGAATGTGAACTTAGCACTTTTATCAATTGGCTTAATCACACCAATGTCACT
ATAGCTGGGCCTCCTGCAGACATATATTGTGTGTACCCTGACTCGTTCTCTGGGGTTTCC
CTCTTCTCTCTTTCCACGGAAGGTTGTGATGAAGAGGAAGTCTTAAAGTCCCTAAAG

FIG. 3G

Molecular tags used (C terminal)

TAP
GATTATAAAGATGATGATGATAAAGGGTCGGCCGCCAGCTGGAGCCACCCTCAGTTCGAG
AAGGGAGGAGGAAGCGGCGGAGGCAGCGGAGGAGGAAGCTGGAGCCACCCGCAGTTCGAG
AAACATCATCACCATCACCATACCGGTCATCATCACCATCACCATTGA

Mouse IgG1 Fc sequence tagged with V5
GTGCCCAGGGATTGTGGTTGTAAGCCTTGCATATGTACAGTCCCAGAAGTATCATCTGTC
TTCATCTTCCCCCCAAAGCCCAAGGATGTGCTCACCATTACTCTGACTCCTAAGGTCACG
TGTGTTGTGGTAGACATCAGCAAGGATGATCCCGAGGTCCAGTTCAGCTGGTTTGTAGAT
GATGTGGAGGTGCACACAGCTCAGACGCAACCCCGGGAGGAGCAGTTCAACAGCACTTTC
CGCTCAGTCAGTGAACTTCCCATCATGCACCAGGACTGGCTCAATGGCAAGGAGTTCAAA
TGCAGGGTMAACAGTGCAGCTTTCCCTGCCCCATCGAGAAAACCATCTCCAAAACCAAA
GGCAGACCGAAGGCTCCACAGGTGTACACCATTCCACCTCCCAAGGAGCAGATGGCCAAG
GATAAAGTCAGTCTGACCTGCATGATAACAGACTTCTTCCCTGAAGACATTACTGTGGAG
TGGCAGTGGAATGGGCAGCCAGCGGAGAACTACAAGAACACTCAGCCCATCATGGACACA
GATGGCTCTTACTTCGTCTACAGCAAGCTCAATGTGCAGAAGAGCAACTGGGAGGCAGGA
AATACTTTCACCTGCTCTGTGTTACATGAGGGCCTGCACAACCACCATACTGAGAAGAGC
CTCTACCACCTGGTAAATAGCGGTAAGCCTATCCCTAACCCTCTCCTCGGTCTCGATTCT
ACGTAA
*V5 sequence is underlined Human IgG1 Fc sequence tagged with FLAG
GAGTCCAAATATGGTCCCCCATGCCCATCATGCCCAGCACCTGAGTTCCTGGGGGGACCA
TCAGTCTTCCTGTTCCCCCCAAAACCCAAGGACACTCTCATGATCTCCCGGACCCCTGAG
GTCACGTGCGTGGTGGTGGACGTGAGCCAGGAAGACCCCGAGGTCCAGTTCAACTGGTAC
GTGGATGGCGTGGAGGTGCATAATGCCAAGACAAAGCCGCGGGAGGAGCAGTTCAACAGC
ACGTACCGTGTGGTCAGCGTCCTCACCGTCCTGCACCAGGACTGGCTGAACGGCAAGGAG
TACAAGTGCAAGGTCTCCAACAAAGGCCTCCCGTCCTCCATCGAGAAAACCATCTCCAAA
GCCAAAGGGCAGCCCCGAGAGCCACAGGTGTACACCCTGCCCCCATCCCAGGAGGAGATG
ACCAAGAACCAGGTCAGCCTGACCTGCCTGGTCAAAGGCTTCTACCCCAGCGACATCGCC
GTGGAGTGGGAGAGCAATGGGCAGCCGGAGAACAACTACAAGACCACGCCTCCCGTGCTG
GACTCCGACGGCTCCTTCTTCCTCTACAGCAGGCTAACCGTGGACAAGAGCAGGTGGCAG
GAGGGGAATGTCTTCTCATGCTCCGTGATGCATGAGGCTCTGCACAACCACTACACACAG
AAGAGCCTCTCCCTGTCTCTGGGTAAACTCGAGGGAGGAGGAAGCGATTATAAAGATGAT
GATGATAAATAA
*FLAG sequence is underlined

FIG. 3H

Cloning vectors used:
pAG3-Zeo (illegible sequence listing)

```
5101 gaggcacta tctcagcgat ctgtcatcca tagttgcctg actcccgtc
5161 gtgtagataa ctacgatacg ggagggctta ccatctggcc ccagtgctgc aatgataccg
5221 cgagacccac gctcaccggc tccagattta tcagcaataa accagccagc cggaaggggcc
5281 gagcgcagaa gtggtcctgc aactttatcc gcctccatcc agtctattaa ttgttgccgg
5341 gaagctagag taagtagttc gccagttaat agtttgcgca acgttgttgc cattgctaca
5401 ggcatcgtgg tgtcacgctc gtcgtttggt atggcttcat tcagctccgg ttcccaacga
5461 tcaaggcgag ttacatgatc ccccatgttg tgcaaaaaag cggttagctc cttcggtcct
5521 ccgatcgttg tcagaagtaa gttggccgca gtgttatcac tcatggttat ggcagcactg
5581 cataattctc ttactgtcat gccatccgta agatgctttt ctgtgactgg tgagtactca
5641 accaagtcat tctgagaata gtgtatgcgg cgaccgagtt gctcttgccc ggcgtcaata
5701 cgggataata ccgcgccaca tagcagaact ttaaaagtgc tcatcattgg aaaacgttct
5761 tcggggcgaa aactctcaag gatcttaccg ctgttgagat ccagttcgat gtaacccact
5821 cgtgcaccca actgatcttc agcatctttt actttcacca gcgtttctgg gtgagcaaaa
5881 acaggaaggc aaaatgccgc aaaaaaggga ataagggcga cacggaaatg ttgaatactc
5941 atactcttcc tttttcaata ttattgaagc atttatcagg gttattgtct catgagcgga
6001 tacatatttg aatgtattta gaaaaataaa caaataggg ttccgcgcac atttccccga
6061 aaagtgccac ctgacgtc
``` pTR2-CB-MC5-TAP-BGHpA (referred to as 'AAV vector')

```
   1 gggcggggcg ggggaggcgt ggcctctgga ggccatctcc ctcctcgct cactgaggcc
  61 gggcgaccaa agtcgccctc gacgcccggg ctgcctcagt ggccaggcga gaccaacgca
 121 gcacggagag aaggagctgc caactagcgt acatagtttc atatagttc atctgttgtc
 181 cctagtatt aatagtaatc aattacgggg tcattagttc atagcccata tatggagttc
 241 cgcgttacat aacttacggt aaatggcccg cctggctgac cgcccaacga cccccgccca
 301 ttgacgtcaa taatgacgta tgttcccata gtaacgccaa tagggacttt ccattgacgt
 361 caatgggtgg actatttacg gtaaactgcc cacttggcag tacatcaagt gtatcatat
 421 ccaagtacgc cccctattga cgtcaatgac ggtaaatggc ccgcctggca ttatgcccag
 481 tacatgacct tatgggactt tcctacttgg cagtacatct atgtattagt catcgctatt
```

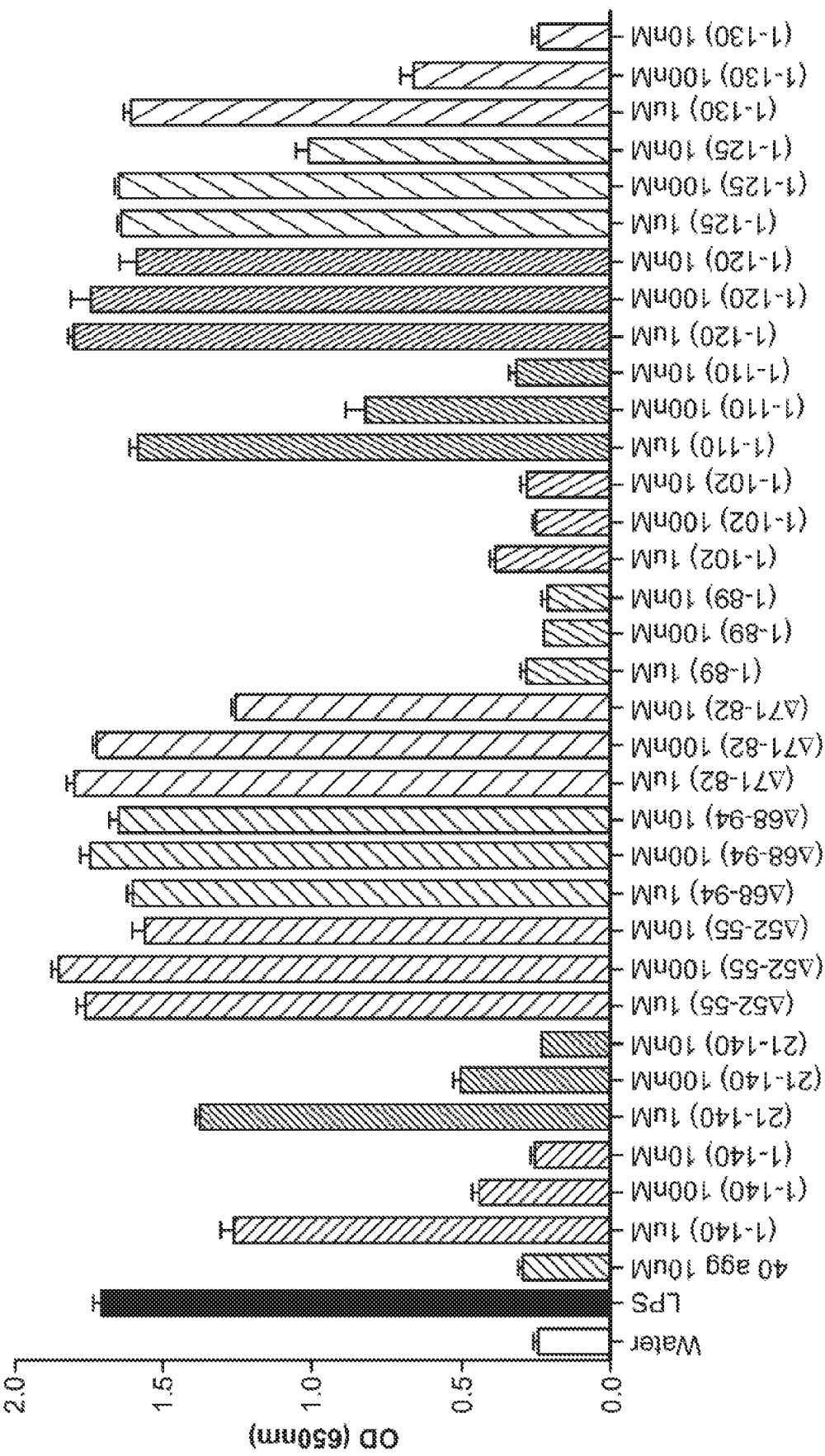

COMPOUNDS FOR TREATING NEURODEGENERATIVE PROTEINOPATHIES

RELATED APPLICATIONS

The present application is a Division of U.S. application Ser. No. 14/775,302, filed Sep. 11, 2015, entitled "Compounds for Treating Neurodegenerative Proteinopathies", which is a national stage filing under 35 U.S.C. § 371 of International PCT application PCT/US2014/029202, filed Mar. 14, 2014, which claims priority to, and the benefit under 35 U.S.C. § 119(e) of U.S. provisional patent application No. 61/802,184, entitled "Compounds for Treating Neurodegenerative Proteinopathies," filed Mar. 15, 2013. The entire content of the aforementioned patent applications are incorporated herein by reference.

STATEMENT OF RIGHTS TO INVENTIONS MADE UNDER FEDERALLY SPONSORED RESEARCH

The invention was made with government support under Grant No. AG018454 awarded by the National Institutes of Health. The government has certain rights in the invention.

BACKGROUND OF THE INVENTION

Toll Like Receptors (TLRs) are endogenous pattern recognition receptors that recognize exogenous pathogen and endogenous danger associated molecular patterns (PAMPs and DAMPs). TLRs are upregulated in neurodegenerative proteinopathies, such as Alzheimer's disease (AD) and Parkinson's disease (PD), and may lead to excessive inflammatory signaling.

Effective therapy for AD, PD and related neurodegenerative diseases remains a huge unmet medical need. Immunotherapeutic approaches remain a major focus of the effort to develop effect disease modifying therapeutics for AD. As opposed to secretase inhibitors that target $A\beta$ production, anti-$A\beta$ immunotherapies have potential to clear preexisting deposits, neutralize toxic $A\beta$ aggregates, or both; thus, there is better rationale for testing immunotherapies in patients with preexisting pathology. In addition, specific immunotherapies that may be capable of targeting tau and $\alpha$-synuclein are of interest.

SUMMARY OF THE INVENTION

This invention relates to novel compounds (e.g., those delineated herein), pharmaceutically acceptable salts, solvates, prodrugs, and hydrates thereof. This invention also provides compositions comprising a compound of this invention and the use of such compounds and compositions in methods of treating diseases and conditions that are beneficially treated by administering compounds that attenuate.

In one aspect, the invention provides an isolated and/or purified compound that is a soluble Toll-Like Receptor (sTLR) or fragment thereof comprising a ligand binding site of a Toll-Like Receptor; an sTLR-Fc fusion protein comprising (i) a sTLR polypeptide comprising a ligand binding site of a Toll-Like Receptor and (ii) an Fc polypeptide; including heterodimers thereof; or combinations of the sTLRs; or a pharmaceutically acceptable salts, esters, amides, hydrates, stereoisomers, prodrugs, or solvates thereof. The sTLRs and sTLR-Fc fusion proteins delineated herein include human and mouse sTLRs and sTLR-Fc fusion proteins.

In one aspect, the invention provides an isolated soluble Toll-Like Receptor (sTLR) or fragment thereof comprising a ligand binding site of a Toll-Like Receptor.

In another aspect, the isolated soluble Toll-Like Receptor (sTLR) is that wherein the ligand binding site is selected from Toll-Like Receptor 2 (TLR2), Toll-Like Receptor 4 (TLR4), Toll-Like Receptor 5 (TLR5), or Toll-Like Receptor 6 (TLR6).

In another aspect, the isolated soluble Toll-Like Receptor (sTLR) is that wherein the ligand binding site binds a disease associated molecular pattern (DAMP) and/or pathogen associated molecular pattern (PAMP).

In another aspect, the isolated soluble Toll-Like Receptor (sTLR) is that wherein the disease associated molecular pattern (DAMP) is one or more of $A\beta40$, $A\beta42$, tau, and synuclein.

In another aspect, the isolated soluble Toll-Like Receptor (sTLR) is that wherein the soluble Toll-Like Receptor is sTLR2-TAP, sTLR4-TAP, sTLR5-TAP, sTLR6-TAP, sTLR2-FLAG, sTLR4-FLAG, sTLR5-FLAG, or sTLR6-FLAG.

In another aspect, the isolated sTLR-Fc fusion protein is that comprising (i) a sTLR polypeptide comprising a ligand binding site of a Toll-Like Receptor and (ii) an Fc polypeptide.

In another aspect, the isolated sTLR-Fc fusion protein is that wherein the sTLR polypeptide and the Fc polypeptide are connected by a peptide linker.

In another aspect, the isolated sTLR-Fc fusion protein is that wherein the C-terminus of the sTLR polypeptide is connected to the N-terminus of the Fc polypeptide.

In another aspect, the isolated sTLR-Fc fusion protein is that wherein the ligand binding site is selected from Toll-Like Receptor 2 (TLR2), Toll-Like Receptor 4 (TLR4), Toll-Like Receptor 5 (TLR5), or Toll-Like Receptor 6 (TLR6).

In another aspect, the isolated sTLR-Fc fusion protein is that wherein the ligand binding site binds a disease associated molecular pattern (DAMP) and/or pathogen associated molecular pattern (PAMP).

In another aspect, the isolated sTLR-Fc fusion protein is that wherein the disease associated molecular pattern (DAMP) is one or more of $A\beta40$, $A\beta42$, tau, and synuclein.

In another aspect, the isolated sTLR-Fc fusion protein is that wherein the sTLR-Fc fusion protein is sTLR2-Fc-V5, sTLR4-Fc-V5, sTLR5-Fc-V5, sTLR6-Fc-V5, sTLR2-Fc-FLAG, sTLR4-Fc-FLAG, sTLR5-Fc-FLAG, or sTLR6-Fc-FLAG.

Another aspect is a method of treating a neurodegenerative proteinopathy disease or disorder in a subject, the method comprising administering to the subject an effective amount of a soluble polypeptide comprising a ligand binding site of a Toll-Like Receptor (TLR).

In another aspect, the method is that wherein the disease or disorder is Alzheimer's disease (AD), Parkinson's disease (PD), synucleinopathy, or tauopathy.

In another aspect, the method is that wherein the sTLR is delivered peripherally or directly to the brain.

Another aspect is a method of modulating $A\beta$ plaque deposition in a subject (e.g., a subject identified as being in need of such treatment), the method comprising administering to the subject an effective amount of a polypeptide comprising polypeptide comprising a soluble polypeptide comprising a ligand binding site of a Toll-Like Receptor (TLR).

Another aspect is a method of modulating plaque associated glial activation in a subject (e.g., a subject identified as being in need of such treatment), the method comprising administering to the subject an effective amount of a polypeptide comprising soluble polypeptide comprising a ligand binding site of a Toll-Like Receptor (TLR).

Another aspect is a method of blocking Aβ, tau, and/or synuclein toxicity in a subject (e.g., a subject identified as being in need of such treatment), the method comprising administering to the subject an effective amount of a soluble polypeptide comprising a ligand binding site of a Toll-Like Receptor (TLR).

Another aspect is a method of modulating harmful effects of Aβ and/or DAMPS in a subject (e.g., a subject identified as being in need of such treatment), the method comprising administering to the subject an effective amount of soluble polypeptide comprising a ligand binding site of a Toll-Like Receptor (TLR).

In another aspect, the method is that wherein the ligand binding site is selected from Toll-Like Receptor 2 (TLR2), Toll-Like Receptor 4 (TLR4), Toll-Like Receptor 5 (TLR5), or Toll-Like Receptor 6 (TLR6).

In another aspect, the method is that wherein the ligand binding site binds a disease associated molecular pattern (DAMP).

In another aspect, the method is that wherein the disease associated molecular pattern (DAMP) is one or more of Aβ40, Aβ42, tau, and synuclein.

In another aspect, the method is that wherein the polypeptide is an isolated soluble Toll-Like Receptor (sTLR) or sTLR-Fc fusion protein.

In another aspect, the method is that wherein the polypeptide is one or more of sTLR2-TAP, sTLR4-TAP, sTLR5-TAP, sTLR6-TAP, sTLR2-FLAG, sTLR4-FLAG, sTLR5-FLAG, sTLR6-FLAG, sTLR2-Fc-V5, sTLR4-Fc-V5, sTLR5-Fc-V5, sTLR6-Fc-V5, sTLR2-Fc-FLAG, sTLR4-Fc-FLAG, sTLR5-Fc-FLAG, or sTLR6-Fc-FLAG.

In another aspect, the method is that wherein the soluble polypeptide comprising a ligand binding site of a Toll-Like Receptor (TLR) is expressed from a vector.

In another aspect, the method is that wherein the vector is an Adeno-associated viral vector (AAV), lentiviral vector, retroviral vector, or herpes simplex viral vector.

In another aspect, the method is that wherein the method decreases inflammation.

Another aspect is a nucleic acid molecule encoding a soluble Toll-Like Receptor (sTLR) herein or a sTLR-Fc fusion protein herein.

Another aspect is a vector comprising a nucleic acid molecule encoding the soluble Toll-Like Receptor (sTLR) herein or a sTLR-Fc fusion protein herein.

In another aspect, the vector of is that wherein the vector is an Adeno-associated viral vector (AAV), lentiviral vector, retroviral vector, or herpes simplex viral vector.

Another aspect is a pharmaceutical composition comprising a soluble polypeptide comprising an isolated soluble Toll-Like Receptor (sTLR) herein or sTLR-Fc fusion protein herein or a vector comprising a nucleic acid sequence comprising a soluble Toll-Like Receptor (sTLR) herein or sTLR-Fc fusion protein herein, and a pharmaceutically acceptable carrier or diluent suitable for injection.

In another aspect, the composition is that further comprising an additional therapeutic agent.

In another aspect, the invention provides a pharmaceutical composition comprising a compound of any of the formulae delineated herein, or a pharmaceutically acceptable salt, ester, amide, hydrate, stereoisomer, prodrug, or solvate thereof, together with a pharmaceutically acceptable carrier or diluent. In other embodiments, the pharmaceutical composition is suitable for administration by injection (subcutaneous, intravenous, parenterally, intraperitoneally, intrathecal), oral administration, rectal administration or transdermal administration. In other embodiments, the pharmaceutically acceptable carrier is suitable for administration by injection (subcutaneous, intravenous, parenterally, intraperitoneally, intrathecal), oral administration, rectal administration or transdermal administration. In other embodiments the composition is not for inhalation. In other embodiments the pharmaceutically acceptable carrier is not for inhalation.

The invention also provides the use of a compound of any of the formulae herein, or a pharmaceutically acceptable salt, ester, amide, hydrate, stereoisomer, prodrug, or solvate thereof, for the manufacture of a medicament for treatment of a disease or condition identified herein.

The invention also provides the use of a compound of any of the formulae herein, or a pharmaceutically acceptable salt, ester, amide, hydrate, stereoisomer, prodrug, or solvate thereof, for administration to a subject for treatment of a disease or condition identified herein.

In another aspect, the invention provides a method of treating an inflammatory, neurodegenerative, or immunomodulatory disease or disorder in a subject (e.g., a subject identified as in need of such treatment), wherein the method comprises administering to the subject an effective amount of a compound of any of the formulae herein, or a pharmaceutically acceptable salt, ester, amide, hydrate, stereoisomer, prodrug, or solvate thereof.

In another aspect, the invention provides a method of treating a disease or disorder in a subject (e.g., a subject identified as being in need of such treatment), wherein the method comprises administering to the subject an effective amount of a compound of any of the formulae herein, or a pharmaceutically acceptable salt, ester, amide, hydrate, stereoisomer, prodrug, or solvate thereof, or composition thereof. In certain embodiments, the disease or disorder is selected from the group consisting of Alzheimer's disease (AD), Parkinson's disease (PD), synucleinopathy, or tauopathy, (e.g., acute, chronic, etc.). In certain embodiments, the disease or disorder is one beneficially treated with immunomodulatory agent (e.g., any compound or composition herein).

In another aspect, the invention provides a method of modulating immune activity in vitro, in a subject, or in a cell. The method comprising contacting (e.g., combining, introducing, administering) a compound of any of the formulae herein or composition thereof with/to the cell and/or subject.

Another aspect of the invention provides a method for preventing or treating a neurodegenerative or neurologic disease such as Alzheimer's disease ("AD"), Parkinson's Disease ("PD"), Amyotrophic Lateral Sclerosis ("ALS"), Multiple Sclerosis ("MS"), Stroke or Frontal temporal Dementia, or a disease or disorder that exhibits a systemic inflammatory condition, such as sepsis, osteoarthritis, rheumatoid arthritis or inflammatory bowel disease in a subject by administering to the subject an effective amount of a soluble polypeptide that possesses a ligand binding site of a Toll-Like Receptor (TLR), to thereby prevent or treat such a disease or disorder. In certain embodiments, the extent of prevention or treatment is evaluated by reference to an appropriate control population, marker level, phenotypic characterization indicative of the disease or disorder, etc. for the indication that is being treated or prevented.

The invention also provides methods for isolation, structure determination, and biological determination of a compound of any of the formulae herein, or a pharmaceutically acceptable salt, ester, amide, hydrate, stereoisomer, prodrug, or solvate thereof. The methods comprise one or a combination of steps or actions essentially as delineated herein, including those specifically recited in the examples herein.

BRIEF DESCRIPTION OF THE DRAWINGS

The present invention is further described below with reference to the following non-limiting examples and with reference to the following figures, in which:

FIGS. 1A and 1B are a schematic of a study methodology to assess the activity of soluble TLRs. FIG. 1A is a schematic depicting construction and verification of soluble TLR constructs. FIG. 1B is a schematic depicting injection of rAAV constructs in neonatal Po TgCRND8 mice, and analysis of tissue.

FIG. 2A is a schematic representation of the different domains in TLRs. Schematic of a typical TLR and its domains (top, left panel). Different TLRs (2, 4, 5 and 6) and their heterodimers are shown with their classic ligands (top, right panel). The soluble TLRs were constructed by removing the intra-membrane and cytoplasmic domains of selected TLRs by PCR cloning from commercially available full length mouse TLRs (bottom panel). FIG. 2B depicts representative mouse sTLR-TAP (left panel) and sTLR-Fc-V5 (right panel) constructs in pTR2 plasmid. The area bounded by the arrowheads was cloned upstream of TAP tag and expressed as soluble non-signaling receptors. Not to scale. LRR, Leucine repeat domain; PCC, polycistine domain; TIR, Toll/IL1beta1 receptor. FIG. 2C depicts representative human sTLR-FLAG (left panel) and sTLR-Fc-FLAG (right panel) constructs in pTR2 plasmid. Not to scale. LRR, Leucine repeat domain; PCC, polycistine domain; TIR, Toll/IL1beta1 receptor. FIG. 2D is an image of a representative anti-FLAg western blot of HEK293 cells transiently transfected with mouse sTLR4 and 5. Mouse sTLR4 and 5 tagged with TAP tag, B. Mouse sTLR4 and 5 tagged with Fc-V5. GFP (green fluorescent protein) is the negative control.

FIGS. 3A-3N depict nucleotide sequences of the constructs described herein. FIG. 3A depicts SEQ ID NO: 1, FIG. 3B depicts SEQ ID NO: 2, FIG. 3C depicts SEQ ID NO: 3, FIG. 3D depicts SEQ ID NO: 4, FIG. 3E depicts SEQ ID NO: 5, FIG. 3F depicts SEQ ID NO: 6, FIG. 3G depicts SEQ ID NOs: 7 (top panel), 8 (middle panel), and 9 (bottom panel), FIGS. 3H-3J and the top panel of FIG. 3K depict SEQ ID NO: 10, and the bottom panel of FIG. 3K and FIGS. 3L-3N depict SEQ ID NO: 11. FIG. 3A shows the nucleotide sequence of mouse soluble TLR2. FIG. 3B shows the nucleotide sequence of mouse soluble TLR4. FIG. 3C shows the nucleotide sequence of mouse soluble TLR5. FIG. 3D shows the nucleotide sequence of mouse soluble TLR2. FIG. 3E shows the nucleotide sequence of human soluble TLR4. FIG. 3F shows the nucleotide sequence of human soluble TLR5. FIG. 3G shows the nucleotide sequences of the molecular tags used (C terminal). FIG. 3H shows the nucleotide sequence of pAG3-Zeo (1-1620). FIG. 3I shows the nucleotide sequence of pAG3-Zeo (1621-3360). FIG. 3J shows the nucleotide sequence of pAG3-Zeo (3361-5100). FIG. 3K shows the nucleotide sequence of pAG3-Zeo (5101-6078) and pTR2-CB-MC5-TAP-BGHpA (1-540). FIG. 3L shows the nucleotide sequence of pTR2-CB-MC5-TAP-BGHpA (541-2220). FIG. 3M shows the nucleotide sequence of pTR2-CB-MC5-TAP-BGHpA (2221-3900). FIG. 3N shows the nucleotide sequence of pTR2-CB-MC5-TAP-BGHpA (3901-5393).

FIG. 14A is a graph depicting the effect of monomeric α-synuclein (a-syn) in TLR4-SEAP assay. HEK-Blue TLR cells stably coexpressing human TLR4/MD-2gene and an NF-κB-inducible SEAP (secreted embryonic alkaline phosphatase) reporter gene was used to test whether different fragments of monomeric synuclein act as TLR ligands in vitro. The numbers denote the amino acids of synuclein that were altered, as denoted in the bottom panel. For example, 1-89 denoted a C terminal deletion of amino acids 89-140 whereas Δ468-94 denotes a deletion of internal amino acids 68 through 94. Assay was performed as per manufacturer's protocol (Invivogen). TLR binding and intracellular signaling was monitored using the SEAP detection media QUANTI-Blue at OD 650 nm. LPS, lipopolysaccharide; 40 agg, aggregated Aβ40.

As shown in FIG. 25B, presence of sTLR5FcV5 protein was tested in sequentially extracted RIPA soluble and detergent (2% SDS) soluble fractions using a V5 immunoprecipitation (IP) assay. (In such experiments, "Bead" lane indicates a mock IP assay; "M" lane indicates molecular weight standards (from top to bottom in kDa, 250, 150, 100, 75, 50, 37); lanes 1-3, rAAV2/1-sTLR5FcV5 injected brain lysates and lanes 4-7, rAAV2/1-GFP injected mice brain lysates; Pos Ct=positive control lanes to test efficiency of V5 IP assay; "4B1" lane was media from sTLR4FcV5-CHO clonal cell line and "5D6" lane was media from sTLR5FcV5-CHO clonal cell line.) The arrow in FIG. 25B corresponds to the expected molecular weight of sTLR5FcV5 protein, which was most prominently observed in RIPA-extracted lanes 1-3, as well as in positive control lanes (the "4B1" lane that contained media from the sTLR4FcV5-CHO clonal cell line and the "5D6" lane that contained media from the sTLR5FcV5-CHO clonal cell line).

In FIG. 26A, TBS-extracted soluble brain lysates obtained from 6 month old mice neonatally injected with rAAV2/1-sTLR5FcV5 or rAAV2/1-GFP were incubated with two different anti-Aβ antibodies bound to Sepharose beads: 4G8 (Covance) corresponding to amino acids 17-24 and Ab5 (T. Golde) corresponding to amino acids 1-16. After binding, immune complexes were then pulled down, separated on a SDS PAGE and tested for the presence of sTLR5FcV5 using anti-V5 tag antibody. Meanwhile, a mock pulldown assay served as a negative control and a lane of purified sTLR5FcV5 protein was loaded at left to assist in molecular weight determination. Total inputs in each lane were assessed using an anti-actin antibody (FIG. 26A, lower panel). In FIG. 26B, dual Li-Cor immunoblotting was used to show that neither purified sTLR5FcV5 nor purified sTLR4FcV5 was recognized by anti-Aβ antibodies 4G8 or Ab5 by themselves (lanes 1 show molecular weight markers, lanes 2 show sTLR4FcV5 results and lanes 3 show sTLR5FcV5 results).

DETAILED DESCRIPTION OF THE INVENTION

Figure 1A:
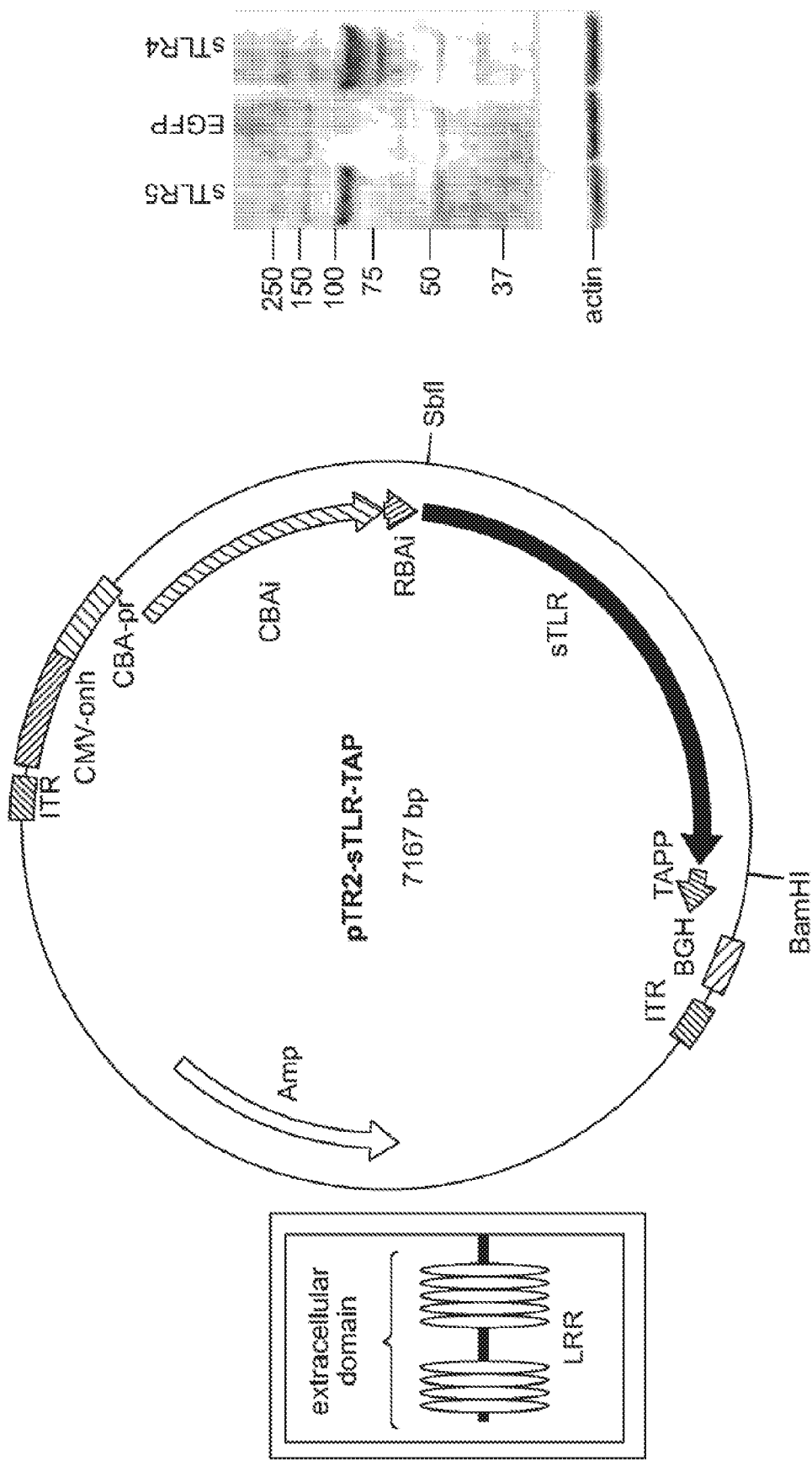

The invention features compounds, compositions, and methods of using such compounds for treating diseases or disorders. In one embodiment, the compounds are useful as novel immune modulatory agents that can attenuate neurotoxicity induced by pathologic disease-associated DAMPS and effectively remove such harmful DAMPs. In one embodiment, the compounds are useful as biologic therapeutics targeting amyloid and other proteinaceous aggregates in neurodegenerative proteinopathies.

The invention is based, at least in part, on the discovery of compounds herein and their use as novel compounds for modulating neurodegenerative disease mechanisms.

Definitions

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, organ or organism.

As used in the specification and claims, the singular term "a", "an" and "the" include plural references unless the context clearly dictates otherwise. For example, the term "a cell" includes a plurality of cells, including mixtures thereof.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "agent" refers to a small molecule compound, a polypeptide, polynucleotide, or fragment, or analog thereof, or other biologically active molecule.

The term "chiral" refers to molecules which have the property of non-superimposability of the mirror image partner, while the term "achiral" refers to molecules which are superimposable on their mirror image partner.

The terms "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, an "amyloid-related disease or disorder" includes Alzheimer's Disease (AD) and Parkinson's Disease (PD).

Exemplary proteinopathies of the invention include AD, Parkinson's Disease, Amyotrophic Lateral Sclerosis ("ALS"), Multiple Sclerosis ("MS"), Stroke and Frontal temporal Dementia.

Diseases or disorders for which prevention and/or treatment is contemplated via administration of the sTLRs of the invention include AD, Parkinson's Disease, Amyotrophic Lateral Sclerosis ("ALS"), Multiple Sclerosis ("MS"), Stroke and Frontal temporal Dementia, and diseases or disorders that exhibit a systemic inflammatory condition, such as sepsis, osteoarthritis, rheumatoid arthritis or inflammatory bowel disease.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

With respect to the nomenclature of a chiral center, terms "d" and "l" configuration are as defined by the IUPAC Recommendations. As to the use of the terms, diastereomer, racemate, epimer and enantiomer is used in their normal context to describe the stereochemistry of preparations.

The term "effective amount" includes an amount effective, at dosages and for periods of time necessary, to achieve the desired result, e.g., sufficient to treat a disease or disorder delineated herein. An effective amount of compound of the invention may vary according to factors such as the disease state, age, and weight of the subject, and the ability of the compound of the invention to elicit a desired response in a cell or in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound (i.e., an effective dosage) may range from about 0.005 µg/kg to about 200 mg/kg, about 0.1 µg/kg to about 100 mg/kg, or about 1 mg/kg to about 50 mg/kg of body weight. In other embodiments, a therapeutically effective concentration may range from about 1.0 nM to about 1 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, between 2 to 10 weeks, between about 1 to 8 weeks, or for about 4, 5, or 6 weeks. It will also be appreciated that the effective dosage of a compound used for treatment may increase or decrease over the course of a particular treatment.

The term "in combination with" is intended to refer to all forms of administration that provide an a compound of the invention together with an additional pharmaceutical agent, such as a second compound used in clinic for treating or preventing osteoclast-related disease or disorder, where the two are administered concurrently or sequentially in any order.

The term "compound," as used herein, is also intended to include any salts, prodrugs, solvates or hydrates thereof.

The term "hydrate" means a compound of the present invention or a salt thereof, which further includes a stoichiometric or non-stoichiometric amount of water bound by non-covalent intermolecular forces.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The terms "isolated," "purified," "pure" or "biologically pure" refer to material that is substantially or essentially free from components (such as proteins, nucleic acids, carbohydrates, and other cellular materials) that normally accompany it as found in its native or natural state, e.g., its state in an organism in which the compound or material naturally occurs. Purity and homogeneity are typically determined using analytical chemistry techniques such as polyacrylamide gel electrophoresis or high performance liquid chromatography. In certain embodiments, a compound of this invention is at least 50% pure, 60% pure, 75% pure, 80% pure, 85% pure, at least 90% pure, or at least 95% pure (e.g., by weight). In certain instances, the compound is at least 98% pure, 99% pure, 99.5% pure, 99.8% pure, or 99.9% pure.

The term "modulate" refers to an increase or decrease, e.g., in the ability of a compound inhibiting activity of a target in response to exposure to a compound of the invention, including for example in an subject (e.g., animal, human) such that a desired end result is achieved, e.g., a therapeutic result.

The term "obtaining" as in "obtaining a compound" capable of modulating (agonizing, antagonizing) a target delineated herein includes purchasing, synthesizing or otherwise acquiring the compound.

The term "subject" includes organisms which are capable of suffering from a disorder as described herein or who could otherwise benefit from the administration of a compound of the present invention, such as human and non-human animals. Preferred humans include human patients suffering from or prone to suffering from diseases or disorders as discussed above, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, fish, etc. A "subject identified as being in need of treatment" includes a subject diagnosed, e.g., by a medical or veterinary professional, as suffering from or susceptible to a disease, disorder or condition described herein.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate) analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The compounds of the present invention may contain an asymmetric carbon atom, for example, as the result of deuterium substitution or otherwise. As such, compounds of this invention can exist as either individual enantiomers, or mixtures of the two enantiomers. Accordingly, a compound of the present invention will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl.

"Stereoisomer" refers to both enantiomers and diastereomers.

"Tert", "*t*", and "t-" each refer to tertiary.

"US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The compounds herein may be in the form of racemic mixtures, enriched in a particular enantiomer or diastereomer. Although specific stereoisomers may be depicted, all such optically active forms and mixtures are contemplated.

Exemplary Synthesis

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds herein and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods to make the compounds described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Toll-Like Receptors (TLRs)

Toll-like Receptors (TLRs) are major positive effectors of innate immunity and central to the development of antimicrobial inflammatory responses initiated by PAMP (pathogen associated molecular pattern) binding. A typical TLR has leucine rich (LRR) ligand binding ectodomain, a transmembrane domain and the cytoplasmic signaling TIR domain (see FIG. 1). Binding of different DAMPs and PAMPs with the ectodomain leads to engagement of adaptor proteins to the intracellular TIR domain, leading to activation of transcription of inflammatory mediators. Adaptor proteins, MyD88, MAL/TRAP, TRW, SARM and TRAM, transduce signals from the TIR domain by activating a series of protein kinases which in activate pro-inflammatory transcription factors (e.g., NF-κB, IRFs). All TLRs are constitutively expressed in the central nervous system (CNS) and they have been reported to confer neuroprotection and neurotoxicity, but there has been relatively limited study of TLRs in neurodegenerative proteinopathies. Consistent with their role in innate immunity TLRs are expressed on microglia and astrocytes in the brain, but they also can be expressed on neurons.

There are 10 human TLRs with TLRs 1, 2, 4, 5, 6 and 10 functioning as extracellular receptors. These TLRs are found primarily on the cell surface and are activated by extracellular ligands. TLRs 3, 7, 8 and 9 function as lumenal receptors, as they are primarily expressed in endosomes and the ER and are activated by ligands binding in the lumen of these organelles. TLRs can from noncovalent homodimers and some form heterodimers. Generally, TLR ligands fall into three classes: lipids and lapidated peptides (which bind TLR4 and the heterodimers TLR2/1 and TLR2/6), proteins (TLR5), and nucleic acids (TLR 3, 7, 8, 9). TLRs not only recognize exogenous pathogen associated molecular patterns (PAMPs) but also endogenous disease associated molecular patterns (DAMPs). Significantly, recent evidence demonstrates that misfolded amyloidlike proteins including Aβ and α-synuclein aggregates represent DAMPs that can bind and active select TLRs. In vitro studies have shown that Aβ aggregates can bind and activate TLR2, 4 and a tripartite complex of CD36-TLR2-TLR6. Other amyloids and α-synuclein aggregates are also impacted as ligands and activators of TLR2 and 4 18, 65. TLRs have also been shown to regulate Aβ deposition. Administration of TLR4 and TLR9 agonists decreases Aβ loads in APP transgenic mice brains, whereas knocking down TLR2 or TLR4 in APP mice exacerbates Aβ plaque pathology.

Activation of TLR co-receptors or adaptor proteins like Myd88 also appears to regulate Aβ aggregate induced inflammation and deposition. TLR4 and TLR2 exacerbates Aβ induced neuronal injury, and abolishing Myd88 signaling rescues cells from Aβ-induced neurotoxicity, indicating that Aβ aggregate-induced TLR engagement may be detrimental to cell viability. Though these data all paint a picture that Aβ-aggregates and other DAMPs activate several TLRs increasing inflammation and thereby reduce Aβ; one study of Myd88 KO showed that loss of Myd88 paradoxically reduced Aβ deposition, whereas myd88 haploinsuffcieny was reported to be beneficalas well. Of interest, TLR2 and 4 variants have also been associated with AD risk Chinese populations Generation of soluble TLRs is a naturally occurring phenomenon for many innate immune receptors, whereby ectodomain shedding of the ligand binding domain results in decoy receptor that blocks singling thorough the intact receptor. Although not all TLRs are known to have a naturally occurring soluble form, TLR 2, 4, 5 and 6 do. Given the structural similarities among all the TLRs there is no a priori reason why engineered TLRs cannot be utilized. As described herein, decoy receptors were generated by removing the transmembrane domain and the TIR domain of native full length TLRs (flTLR) and expressing these (see FIG. 1, the region bounded by arrowheads,) as sTLRs. For example, soluble immune decoy receptors provide important negative regulatory mechanisms for cytokines and chemokines, and for their respective receptor interactions. Such decoy receptors can essentially bind and/or sequester ligands and be removed from the circulation by complement and other innate immune system components following ligand binding. Multiple sTLRs that could effectively block TLR signaling (Table 1). Without being bound to a particular theory, natural soluble TLRs (sTLR) are thought to prevent excessive triggering of membrane-bound TLRs and subsequent overactivation of the innate immune system (Table 1). Such a mechanism has the potential to provide a direct attenuation of acute host inflammatory responses to pathogenic ligands and stress proteins.

TABLE 1

Naturally occurring sTLRs

| Protein | Source | Function | Reference |
|---|---|---|---|
| sTLR2 | Breast milk | Inhibits HIV proliferation and cell free HIV infection | Henrick, 2012, PLoS One |
| sTLR4, sTLR2 | Human saliva | Inhibits LPS signaling; | Zunt, Clin Exp |
| sTLR2 | | Modulates IL-8 production by monocytes | Imunol 2009; Kuroishi, 2007, Mol Immunol |
| sTLR2 | Human plasma, breast milk | Serum depletion results in higher sensitivity to LPS | LeBouder, 2003, J Immunol |

TABLE 1-continued

Naturally occurring sTLRs

| Protein | Source | Function | Reference |
|---|---|---|---|
| sTLR2 | Human amniotic fluid | Antagonizes TLR2 signaling in vitro | Dulay, 2009, J Immunol |
| sTLR2 | sTLR2 ip in mice | reduces inflammation without compromising bacterial clearance | Raby, 2009, J Immunol |
| sCD14, sTLR2 | saliva | Biomarker of burning mouth syndrome | Srinivasan, 2008, Clin Immunol; |
| sCD14 | saliva | | Uehara, 2003, Clin Diagn Lab Immunol |
| sCD14 | Synovial fluid | Biomarker of early stage osteoarthritis | Nair, 2012, Arthrith Rheum |
| sCD14 | Human astrocyte (functional screen) | Agonist of TLR2 signaling in vitro | Bsibsi, 2007, Glia |
| sTLR9 | Invitro (HEK293, RAW, HeLA) | Binds to CpG and negatively regulates TLR9 signaling | Chockalingam, 2011, Eur J Immunol |
| sTLR5 | Brain, heart, kidney of Japanese flounder; Catfish; Atlantic salmon | Upregulated in flounder following flagellin stimulation | Hwang, 2010; Fish Shellfish Immunol; Baoprasertkul, 2007, Fish Shellfish Immunol; Tsoi, 2006, Vet Immunol Immunopathol |
| sTLR5 | Rainbow trout | Binds to flagellin | Tsujita, 2006, Vaccine |

Negatively targeting TLR-induced inflammasome by such endogenous decoy receptors has the potential to harness the beneficial effects of innate immune signaling (i.e., Aβ removal by activated glia) while minimizing bystander toxicity (i.e., inflammasome-induced sterile inflammation) in a mouse model of Alzheimer's disease, as described herein. Compared to using widely available TLR inhibitors or antagonists (Table 2), this approach enables one to utilize the beneficial component of innate immune activation (i.e., binding and removing DAMPs, while attenuating activation of excessive cytokines and other harmful factors). It is possible that using TLR inhibitors may have unexpected detrimental effects by shutting down the cells' first line of defense (i.e., the innate immune system) in the face of accumulating DAMPs. Advantageously, sTLRs have broader biological activity, as they are capable of targeting Aβ, synuclein, and tau. Fully human versions would be well tolerated and non-immunogenic.

TABLE 2

Clinical development status of TLR antagonists

| Compound | Targeting TLR | Developing company | Indications | Clinical status |
|---|---|---|---|---|
| OPN-305 | TLR2 | Opsona Therapeutics | Inflammation, autoimmunity, ischemia/reperfusion | Preclinical |
| OPN-401 | TLR4 | Opsona Therapeutics | Inflammatory bowel disease, RA | Preclinical |
| Eritoran | TLR4 | Eisai Pharma | Sepsis and septic shock | Phase III |
| TAK-242 | TLR4 | Takeda Pharma | Sepsis | Suspended in Phase III |
| Cpn10 | TLR4 | CBio Ltd | RA, MS, psoriasis | Phase II |
| NI-0101 | TLR4 | NovImmune | Acute and chronic inflammation | Preclinical |
| 1A6 | TLR4 | NovImmune | Colitis | Preclinical |
| AV411 | TLR4 | Avigen | Pain management and withdrawal | Phase II |

TABLE 2-continued

Clinical development status of TLR antagonists

| Compound | Targeting TLR | Developing company | Indications | Clinical status |
|---|---|---|---|---|
| IRS-954 (DV-1079) | TLR7 and 9 | Dynavax Technologies | SLE, HIV | Preclinical |
| IMO-3100 | TLR7 and 9 | Idera Pharma | SLE, RA, MS | Phase I |
| CPG-52364 | PolyTLR | Pfizer | SLE | Phase I completed |

RA: Rheumatoid arthritis;
SLE: Systemic lupus erythematosus

Therefore, using sTLRs as alternatives to TLR inhibitors or antagonists may synergize with the natural defense capacity of the body to recognize and remove harmful DAMPs. In addition, different sTLRs have been designed that are tagged with immunoglobulin (IgG) at their C terminal ends. The purpose of this is manifold: 1) it increases solubility and extends half-life of molecules in vivo, 2) the TLRs are phagocytosed more effectively by cellular mechanisms, such as FcR mediated mechanisms, and 3) it allows fast and efficient purification and detection in vitro. Mutliple anti-Abeta anitbodies (passive immunotherapeis) for AD are in trial.

Compositions

The invention also provides compositions comprising an effective amount of a compound herein, or a pharmaceutically acceptable salt, prodrug, solvate, or hydrate of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80, solutol and the like) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Brain pumps are explicitly contemplated as an exemplary mode of delivery for the therapeutics of the invention.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as a compound of any of the formulae herein.

Preferably, the second therapeutic agent is an agent useful in the treatment or prevention of a disease or condition selected from neurodegeneration, inflammation, immunomodulation, or neuroinflammation (e.g., acute, chronic, etc.).

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can vary dependent on the subject. Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention is expected to vary from about 0.005 µg/kg to about 200 mg/kg per day, or 0.001 milligram per kilogram of body weight per day (mg/kg/day) to about 100 mg/kg/day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for a compound of any of the formulae herein.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of directly or indirectly modulating the activity of amyloid-like protein aggregation, DAMPS, or PAMPS in a cell, comprising contacting a cell with one or more compounds herein.

According to another embodiment, the invention provides a method of treating a patient suffering from, or susceptible to, a disease that is beneficially treated by a compound of any of the formulae herein comprising the step of administering to said patient an effective amount of a compound or a composition of this invention. Such diseases are well known in the art and are disclosed herein as well.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method). In other methods, the subject is prescreened or identified as in need of such treatment by assessment for a relevant marker or indicator of suitability for such treatment.

In another embodiment, any of the above methods of treatment comprises the further step of co-administering to said patient one or more second therapeutic agents. The choice of second therapeutic agent may be made from any second therapeutic agent known to be useful for co-administration with a compound of any of the formulae herein. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In yet another aspect, the invention provides the use of a compound delineated herein (e.g., sTLR, sTLR-Fc fusion protein) alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound delineated herein for use in the treatment or prevention in a patient of a disease, disorder or symptom thereof delineated herein.

The administration of a composition of the invention for the treatment of a neurodegenerative proteinopathy disease or disorder may be by any suitable means that results in expression of an effective amount of sTLR that, combined with other components, is effective in ameliorating, reducing, or stabilizing the disease. For example, an amount that reduces plaque formation, including amyloid (Aβ40, Aβ42), tau, and/or synuclein, plaque formation. A therapeutic sTLR expression vector or sTLR polypeptide may be contained in any appropriate amount in any suitable carrier substance, and is generally present in an amount of 1-95% by weight of the total weight of the composition. The composition may be provided in a dosage form that is suitable for parenteral (e.g., intravenously, intra-arterial) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

If desired, therapeutic compositions of the invention (e.g., a viral expression vector comprising a polynucleotide encoding an sTLR polypeptide) are provided together with other agents that are useful for reducing inflammation or that are otherwise therapeutic for neurodegenerative proteinopathy disease or disorder.

Polynucleotide Therapy

For therapeutic uses, a viral expression vector comprising a polynucleotide encoding an sTLR polypeptide disclosed herein may be administered systemically, for example, formulated in a pharmaceutically-acceptable buffer, such as physiological saline. Preferable routes of administration include, for example, intravenous, intra-arterial, into the cerebrospinal fluid, into the ventricles of the brain, or any other injection site that provides continuous, sustained levels of expression in the patient to treat a neurodegenerative proteinopathy disease or disorder.

The invention provides methods for recombinantly expressing sTLR in a cell, tissue, or organ. If desired, a viral vector (e.g., an adeno-associated viral vector) is used to inducibly or constitutively express an sTLR polypeptide. Polynucleotide therapy featuring a polynucleotide (e.g., an AAV expression vector, such as an AAV-2, AAV-9 vector) encoding a sTLR protein, variant, or fragment thereof is one therapeutic approach for treating a neurodegenerative proteinopathy disease or disorder (e.g., Alzheimer's disease, Parkinson's disease). Such sTLR-expressing nucleic acid molecules can be delivered to cells (e.g., neurons, endothelial cells, astrocytes, glia) of a subject having a neurodegenerative proteinopathy disease or disorder. The polynucleotide encoding a sTLR protein must be delivered to the cells of a subject in a form in which they can be taken up so that therapeutically effective levels of sTLR can be produced. Preferably, persistent expression of an sTLR polypeptide is maintained at an effective level for longer than 1 week, 2 weeks, 3 weeks, or longer than 1, 3, 6, or 12 months. If desired, the expression of sTLR is combined with any standard method of treating a neurodegenerative proteinopathy disease or disorder (e.g., Alzheimer's disease, Parkinson's disease).

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an sTLR polypeptide, variant, or fragment thereof, can be cloned into a retroviral vector and expression can be driven from its endogenous promoter, from a retroviral long terminal repeat, or from a promoter specific for a target cell type of interest (e.g., neurons, endothelial cells).

In other embodiments, any of the following vectors may be used: Adeno-associated viral vector (AAV), lentiviral vector, retroviral vector, herpes simplex viral vector. More specifically, vectors useful in the methods of the invention include a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). In one embodiment, an adeno-associated viral vector (e.g., serotype 2, 9) is used to administer a polynucleotide intravenously, into the cerebrospinal fluid, or by surgical injection into the brain.

Non-viral approaches can also be employed for the introduction of a therapeutic to a cell of a patient requiring treatment or prevention of a neurodegenerative proteinopathy disease or disorder (e.g., Alzheimer's disease, Parkinson's disease). For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). In one embodiment, the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue or delivered via a canula.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types (e.g. endothelial cells, neurons, astrocytes, glia) can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant sTLR variant, or fragment thereof, either directly to the site of a potential or actual disease-affected tissue, to an organ where the polypeptide will have a therapeutic effect, or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions.

A pharmaceutical composition comprising a viral expression vector comprising a polynucleotide encoding an sTLR polypeptide may be administered by injection (intravenous, intra-arterial, intra-spinal, intra-ventricular or the like), infusion or implantation in dosage forms, formulations, or via suitable delivery devices or implants containing conventional, non-toxic pharmaceutically acceptable carriers and adjuvants. In one embodiment, a therapeutic composition of the invention is provided via an osmotic pump. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. Apart from the active sTLR polynucleotide therapeutic(s), the composition may include suitable parenterally acceptable carriers and/or excipients. The active sTLR polynucleotide therapeutic (s) may be incorporated into an osmotic pump, microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in a form suitable for sterile injection. To prepare such a composition, the suitable active sTLR polynucleotide therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

In one embodiment, a therapeutic composition of the invention (e.g., sTLR polypeptide, an expression vector comprising a polynucleotide encoding an sTLR polypeptide, or cell comprising such agents) is provided locally via a canula.

Kits

The present invention also provides kits for use to treat a disease or disorder in a subject (e.g., a disorder delineated herein). In certain embodiments, the disease or disorder is one beneficially treated with a therapeutic agent (e.g., any compound or composition herein). These kits comprise (a) a pharmaceutical composition comprising a compound herein, or a salt, hydrate, prodrug, or solvate thereof, wherein said pharmaceutical composition is in a container; and (b) instructions describing a method of using the pharmaceutical composition to treat a disease or disorder in a subject (e.g., a disorder delineated herein).

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

The following examples are provided by way of illustration and are not intended to limit the scope of the invention.

EXPERIMENTAL SECTION

Example 1 sTLR4 and sTLR5 Reduced Amyloid Plaques in an Alzheimer's Disease Mouse Model

A study was designed to assess the activity of soluble TLRs, including construction and verification of soluble TLR constructs, injection of rAAV constructs in neonatal P0 TgCRND8 mice, and analysis of tissue. Extracellular TLRs 2, 4, 5 and 6 were selected for study, as they have been described as having a naturally occurring soluble form. In particular, TLR5 was chosen because flagellin is a protein PAMP for TLR5. Without being bound to a particular theory, TLR5 might also recognize ordered protein DAMPs such as Aβ amyloid. Interestingly, flagellin proteins lacking the N- or C-terminus form polymers of reduced filament stability, especially the N terminal 1-15 residues readily form β Sheet fibrils, resembling β-amyloid and prion peptides (Hakalehto, 2004).

Figure 2A:
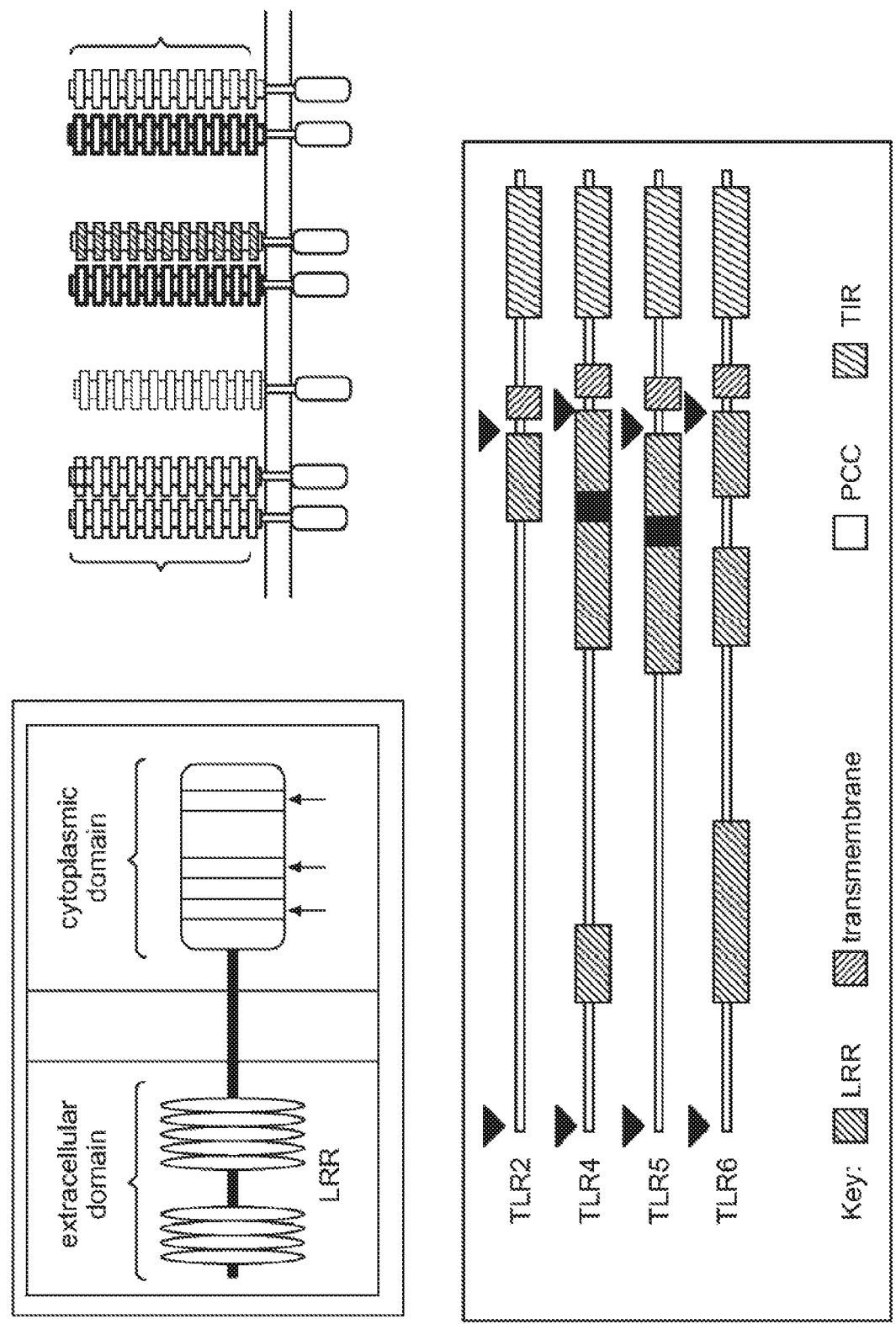
FIGS. 2A-2D depict the construction and verification of soluble TLR constructs.
Figure 2B:
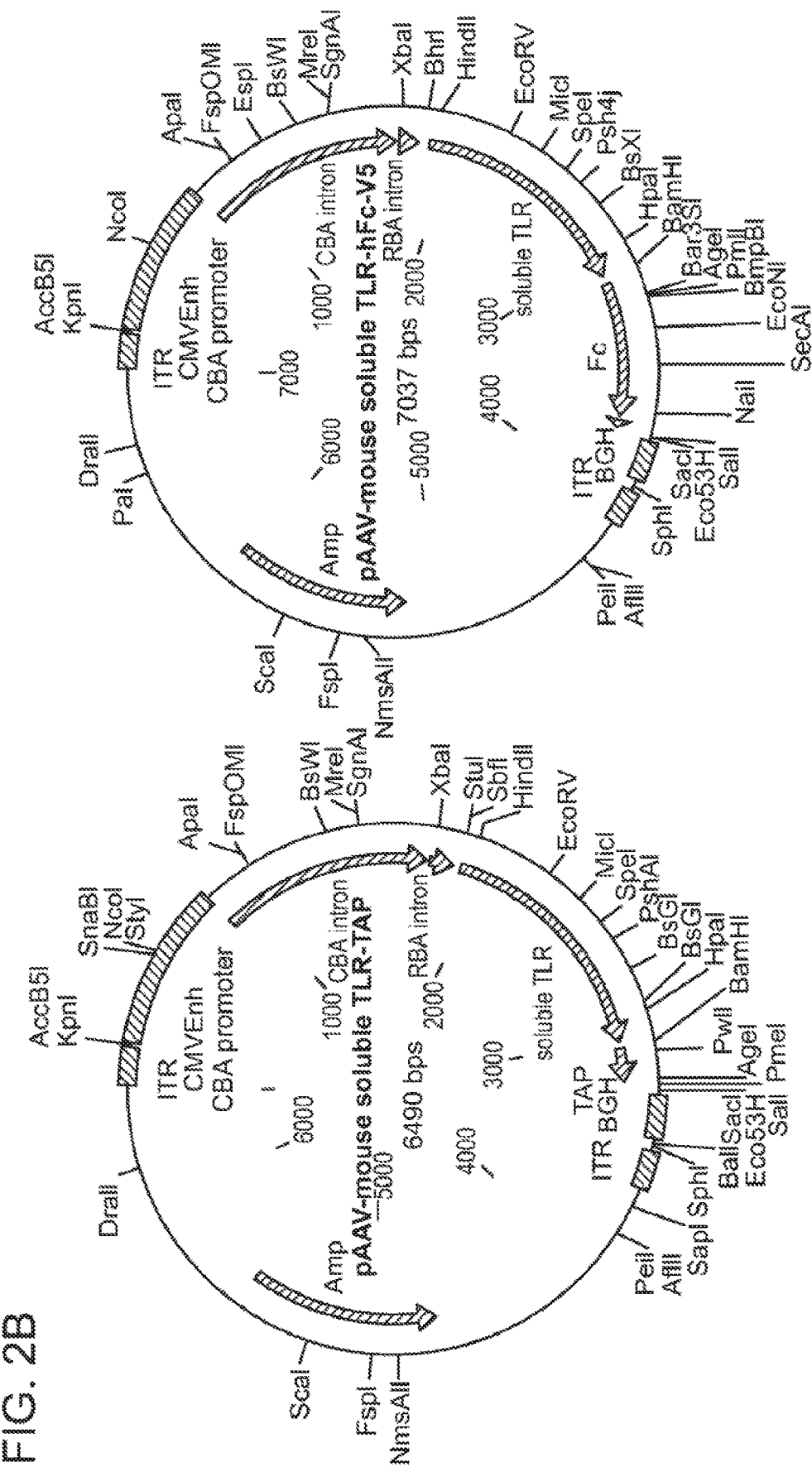
Figure 2C:
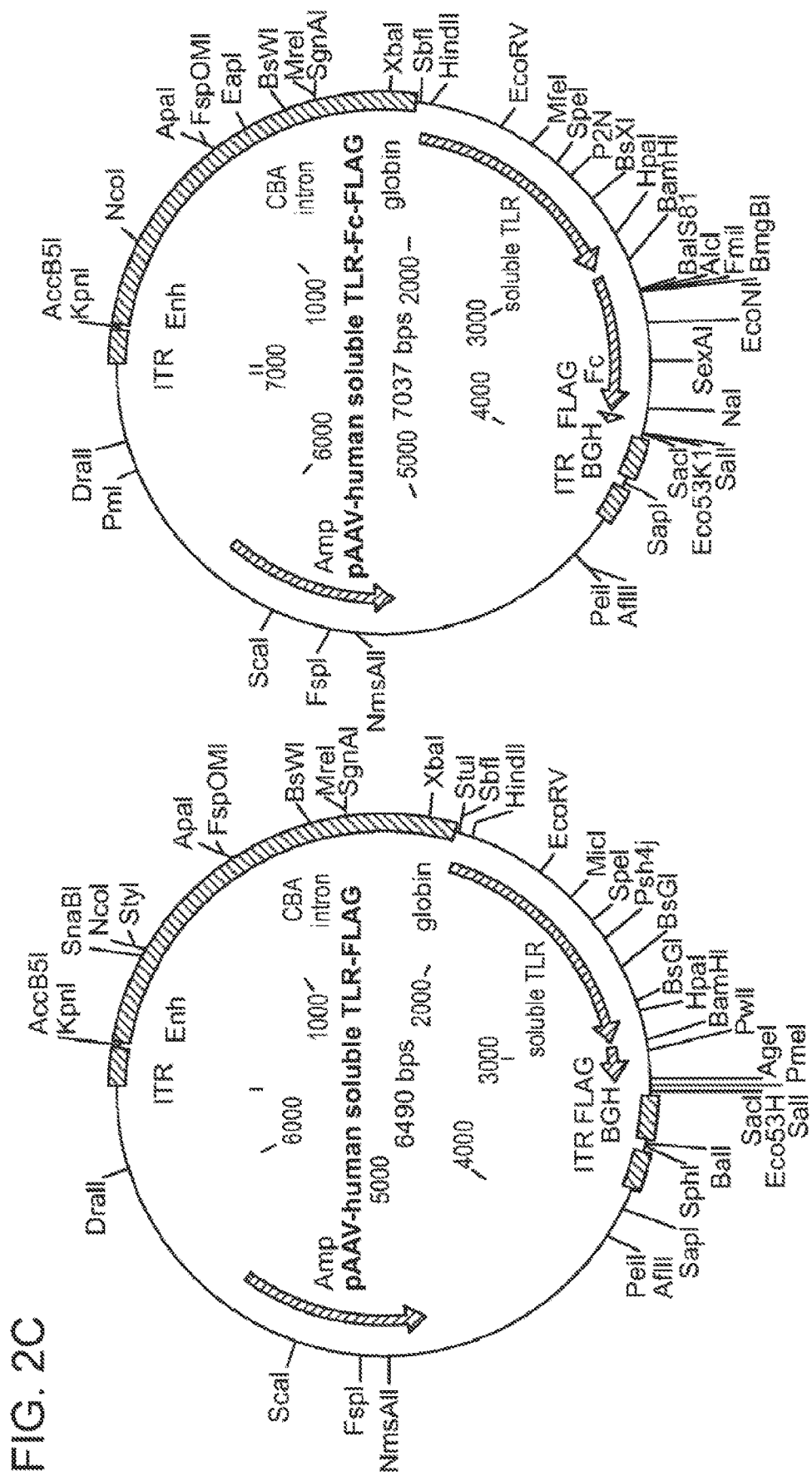
Figure 2D:
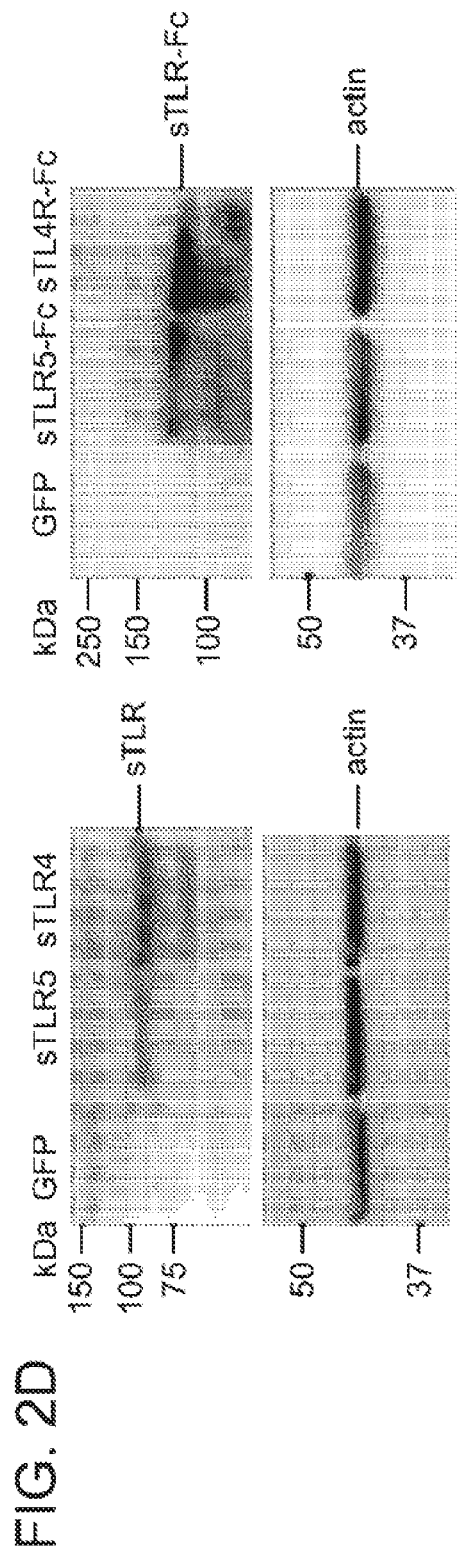

Mouse sTLR2, 4, 5 and 6 were cloned and expressed in pAG3 vector and pAAV2 vectors (FIG. 2A). Both these vectors contain a TAP tag (Strep/FLAG tandem affinity purification Gloeckner, 2007) in the C terminus. These were also re-cloned upstream of a mouse IgG Fc sequence flanked by the V5 tag (Table 3; FIG. 2B). The corresponding human sequences were cloned in both pAG3 and pAAV2 vectors, flanked by a C terminal FLAG sequence or a fusion of human IgG Fc and FLAG sequence (FIG. 2C). The predicted sizes are described at Table 4. Human and mouse TLRs, although conserved in terms of overall domain organization and size, are not identical—the sequence identity in the amino acid level are TLR2 (71%), TLR4 (67%), TLR5 (73%) and TLR6 (74%). A representative immunoblot showing transiently transfected HEK293 cells expressing mouse sTLR-TAP is depicted (FIG. 2D). Individual DNA sequences of all the constructs (mentioned in Table 4) are provided in FIGS. 3A-3N.

TABLE 3

Description of constructs used.

| Molecule | Species | Accesion # of parent molecule | Length (nt) | Amino Acid | Predicted MW, kD |
|---|---|---|---|---|---|
| sTLR2-TAP | Mouse | NM_011905.3 | 1973 | 657 | 73.9 |
| sTLR4-TAP | Mouse | NM_021297.2 | 2066 | 688 | 77.8 |
| sTLR5-TAP | Mouse | NM_016928.2 | 2081 | 693 | 78 |
| sTLR6-TAP | Mouse | NM_006068.4 | 1298 | 432 | 49.6 |
| sTLR2-Fc-V5 | Mouse | NM_011905.3 | 2534 | 844 | 95.1 |
| sTLR4-Fc-V5 | Mouse | NM_021297.2 | 2627 | 875 | 98.9 |
| sTLR5-Fc-V5 | Mouse | NM_016928.2 | 2642 | 880 | 99.1 |
| sTLR6-Fc-V5 | Mouse | NM_006068.4 | 1859 | 619 | 70.8 |
| sTLR2-FLAG | Human | NM_003264.3 | 1814 | 604 | 68.1 |
| sTLR4-FLAG | Human | NM_003266.3 | 1823 | 607 | 68.8 |
| sTLR5-FLAG | Human | NM_003268.5 | 2618 | 872 | 99.3 |
| sTLR6-FLAG | Human | NM_011604.3 | 2432 | 810 | 93.4 |
| sTLR2-Fc-FLAG | Human | NM_003264.3 | 2501 | 833 | 93.9 |
| sTLR4-Fc-FLAG | Human | NM_003266.3 | 2510 | 836 | 94.6 |
| sTLR5-Fc-FLAG | Human | NM_003268.5 | 1917 | 884 | 99.5 |
| sTLR6-Fc-FLAG | Human | NM_011604.3 | 2504 | 834 | 94.9 |

Figure 3I:
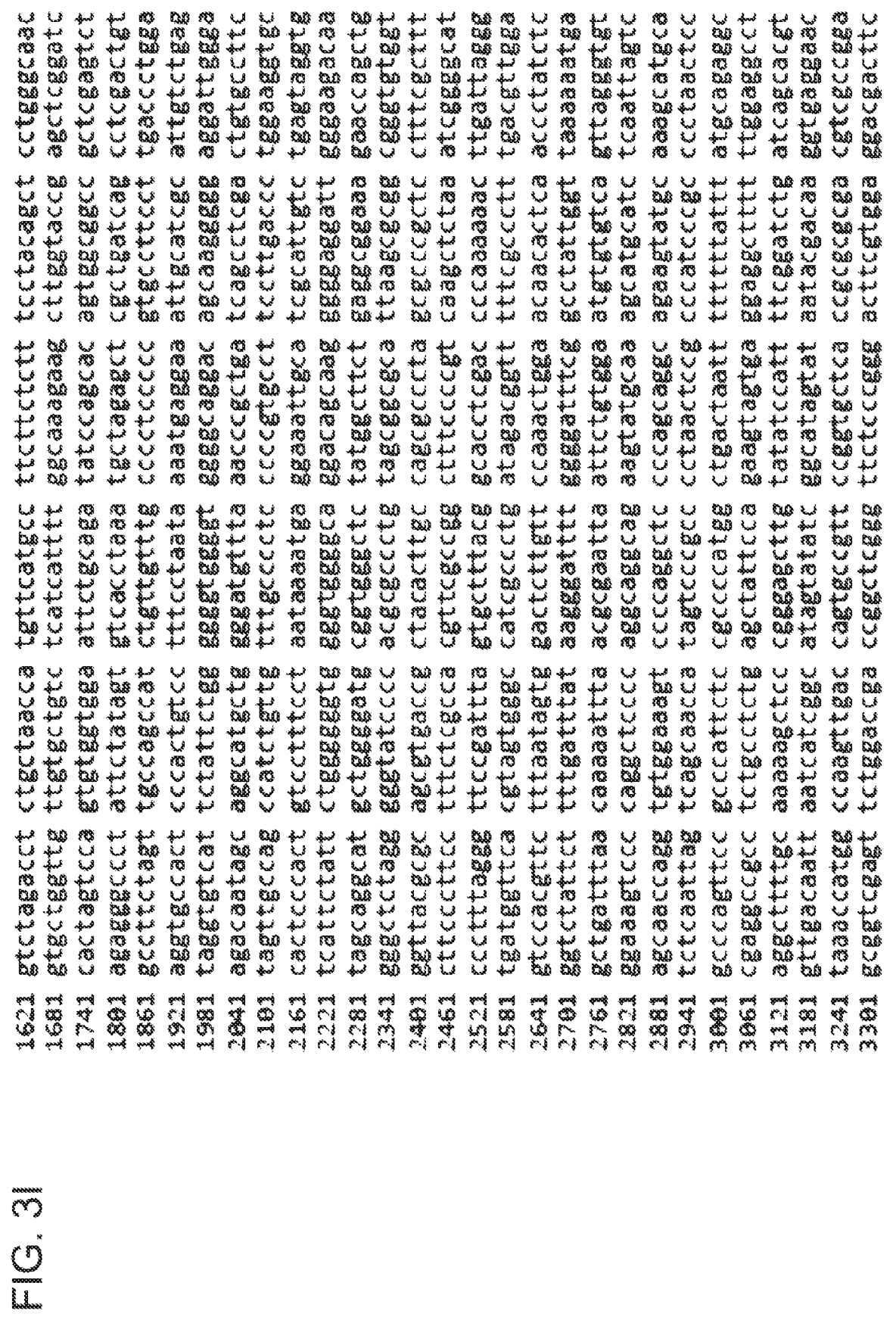
Figure 3J:
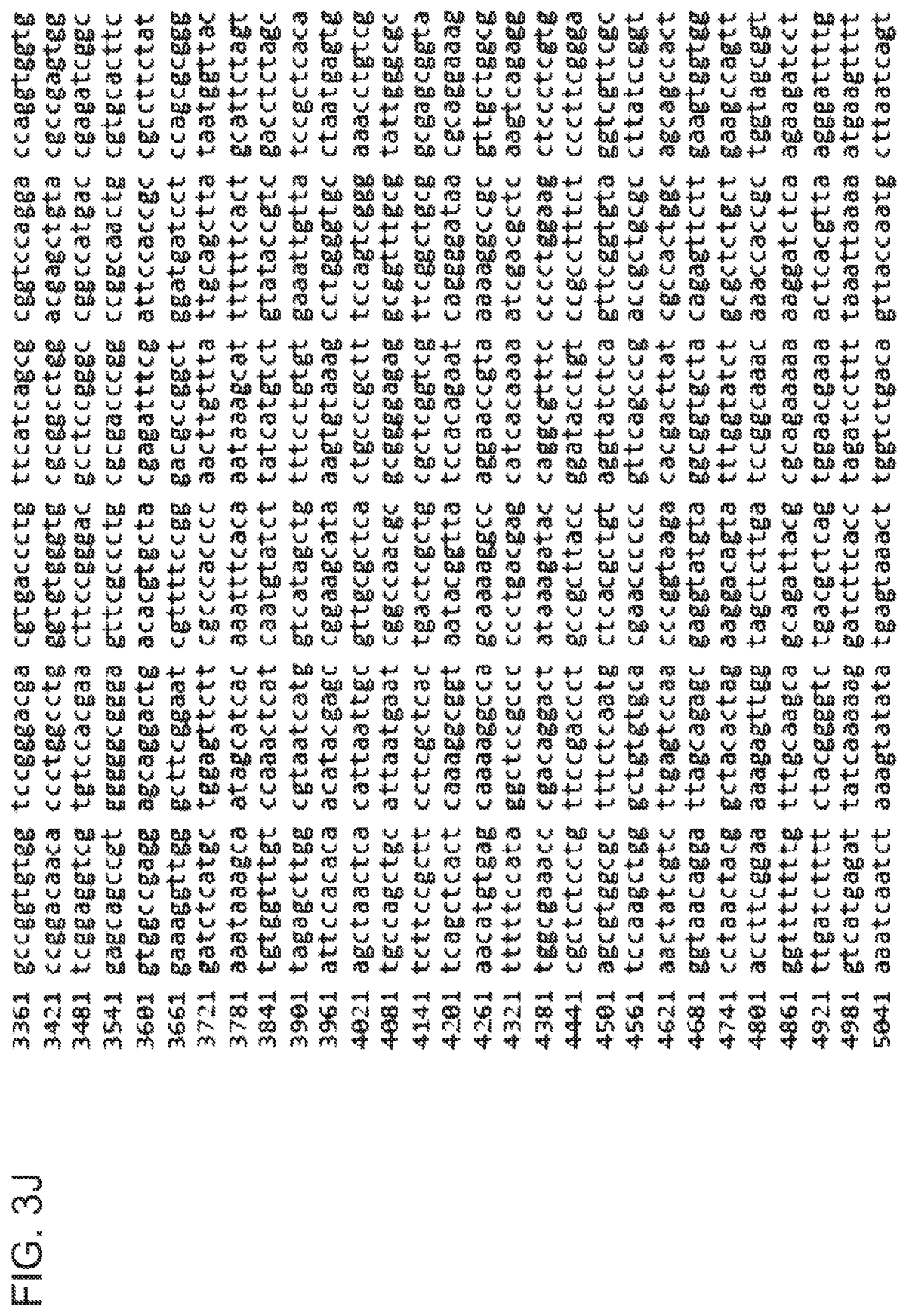
Figure 3L:
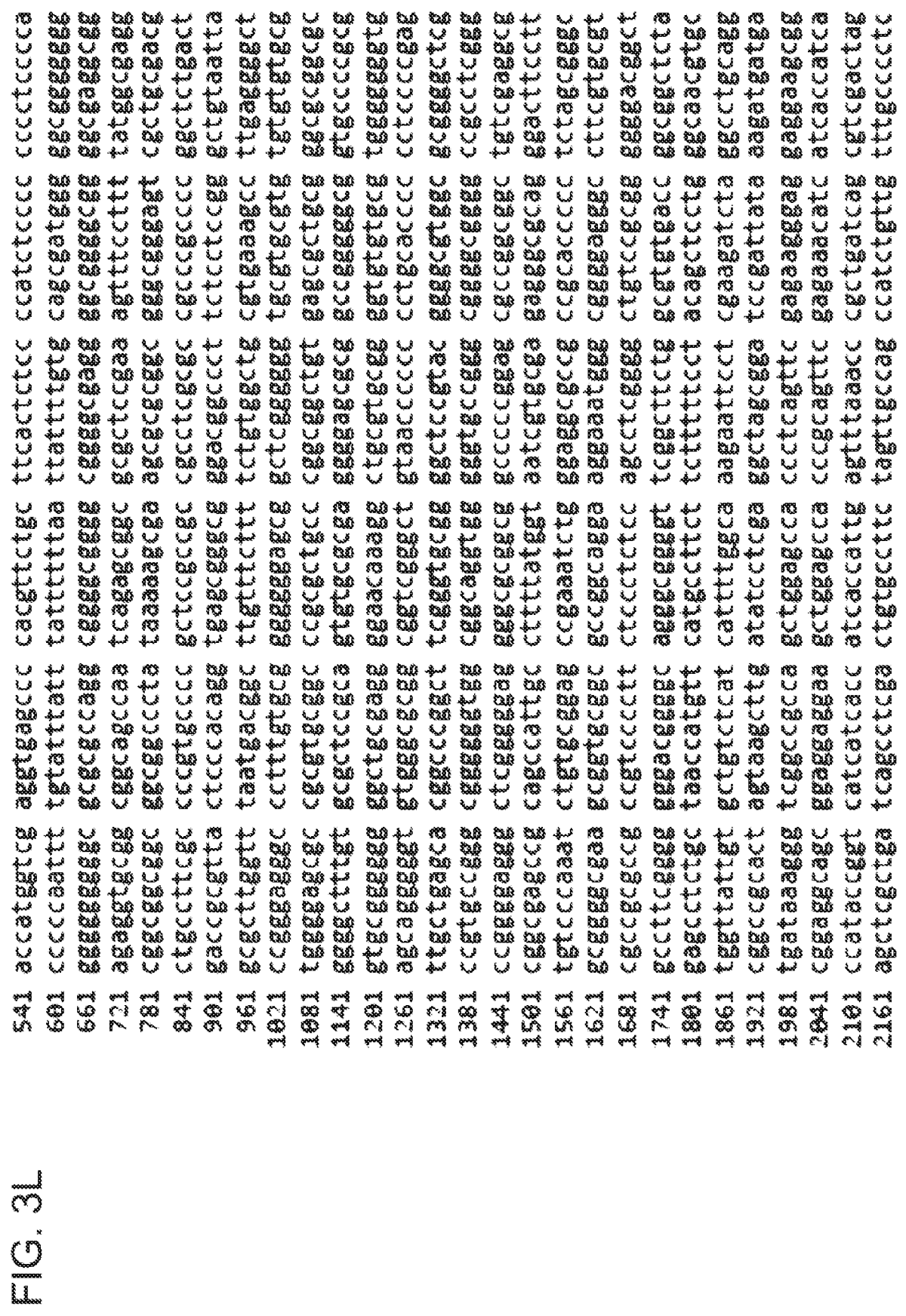
Figure 3M:
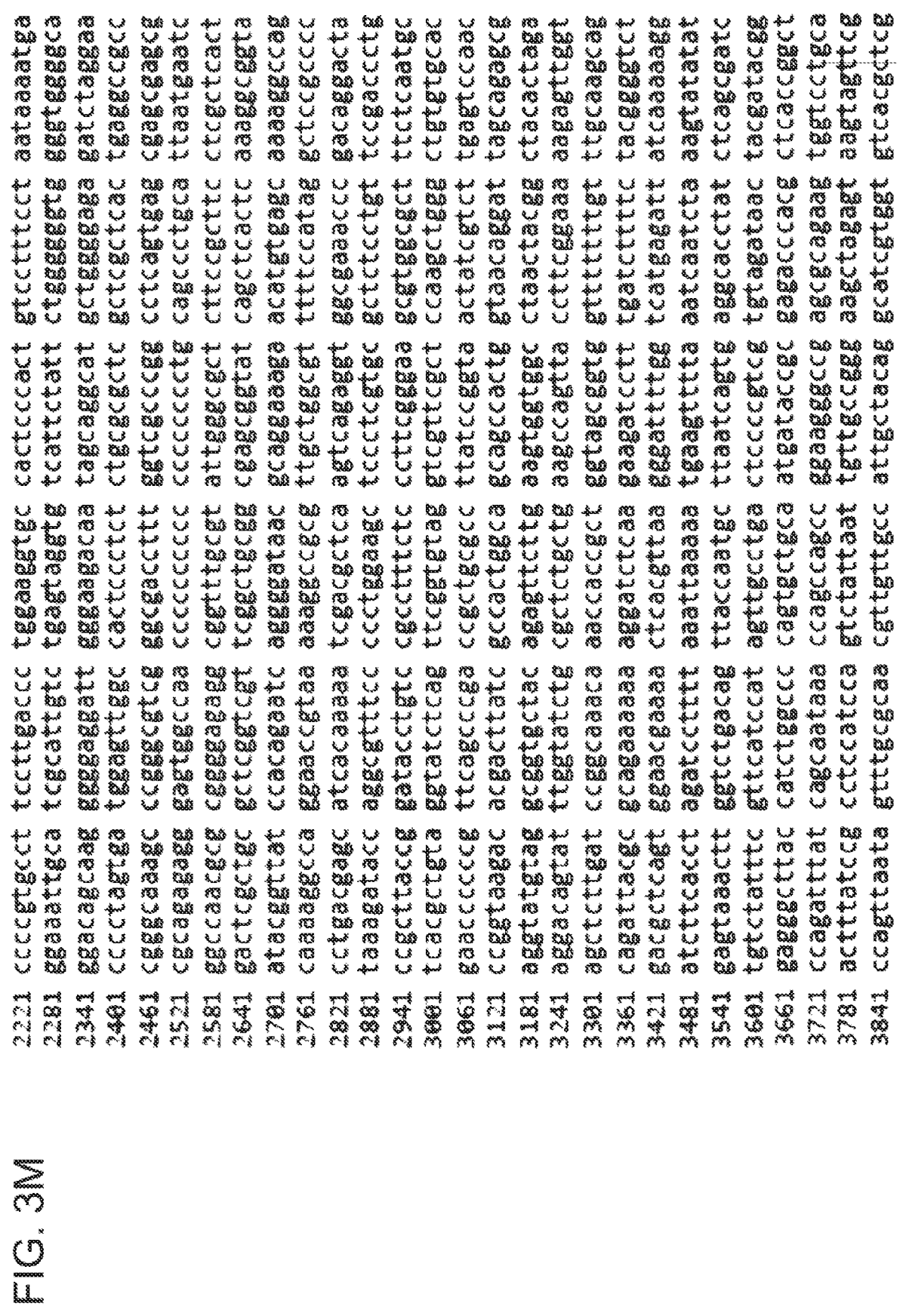
Figure 3N:
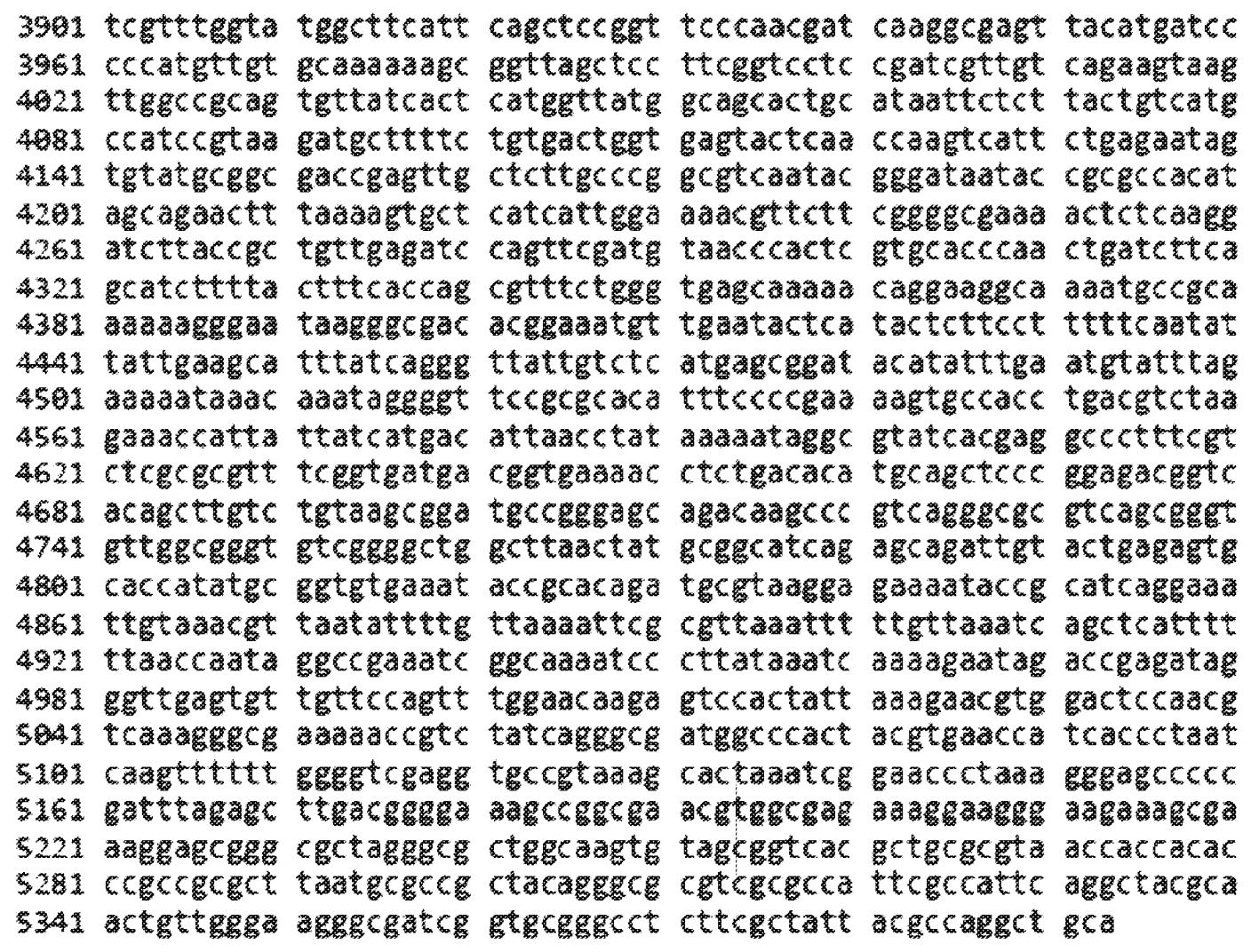

See FIGS. 3A-3N for nucleotide sequences.

Figure 4A:
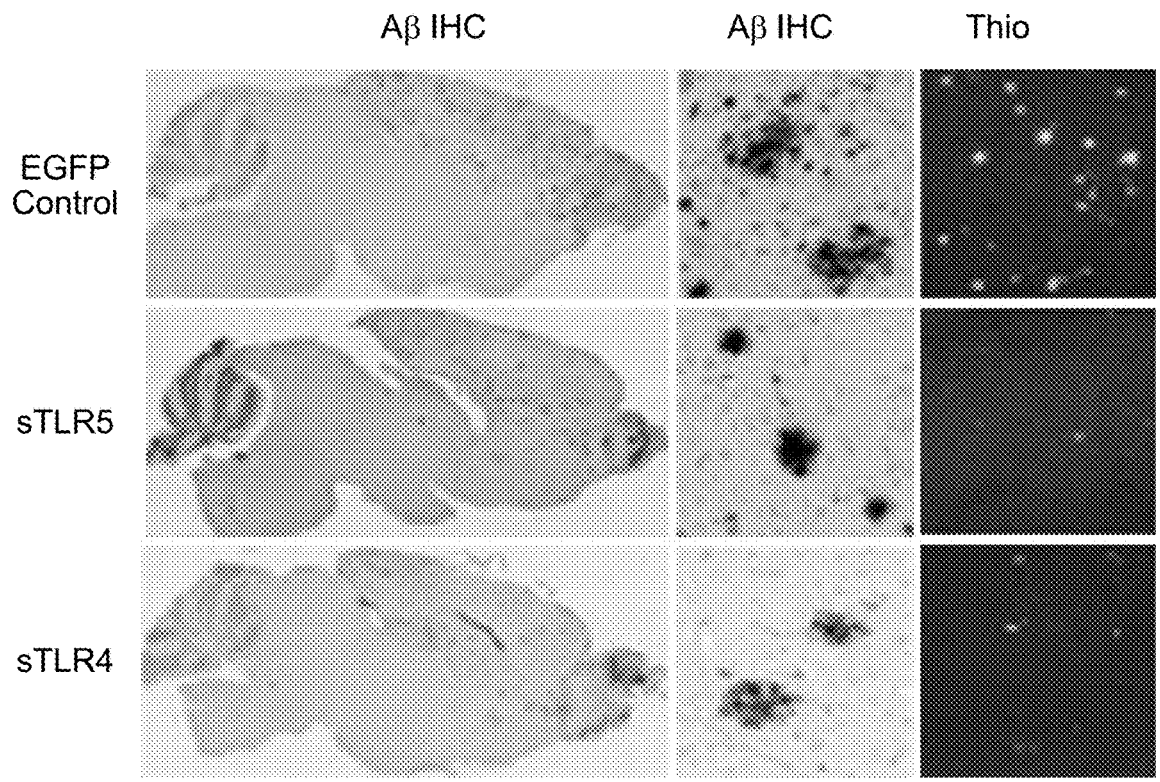
FIGS. 4A and 4B show that sTLRs reduced Aβ plaque pathology in Alzheimer's disease mice brains. rAAV2/1 mediated delivery of sTLR4 and 5 to neonatal day P0 CRND8 mice brains shows marked decreases in Aβ deposition at 5 months of age. Both total plaque burden, total number of Thioflavin S cored plaques and formic acid extracted insoluble Aβ levels decreased in sTLR4 and sTLR5 expressing mice compared to controls. Quantification of Plaque Burden (Aperio pixel count program) and Thio S positive plaques (n=6-8 per group) were done on formalin fixed paraffin embedded brain sections.
Figure 4B:
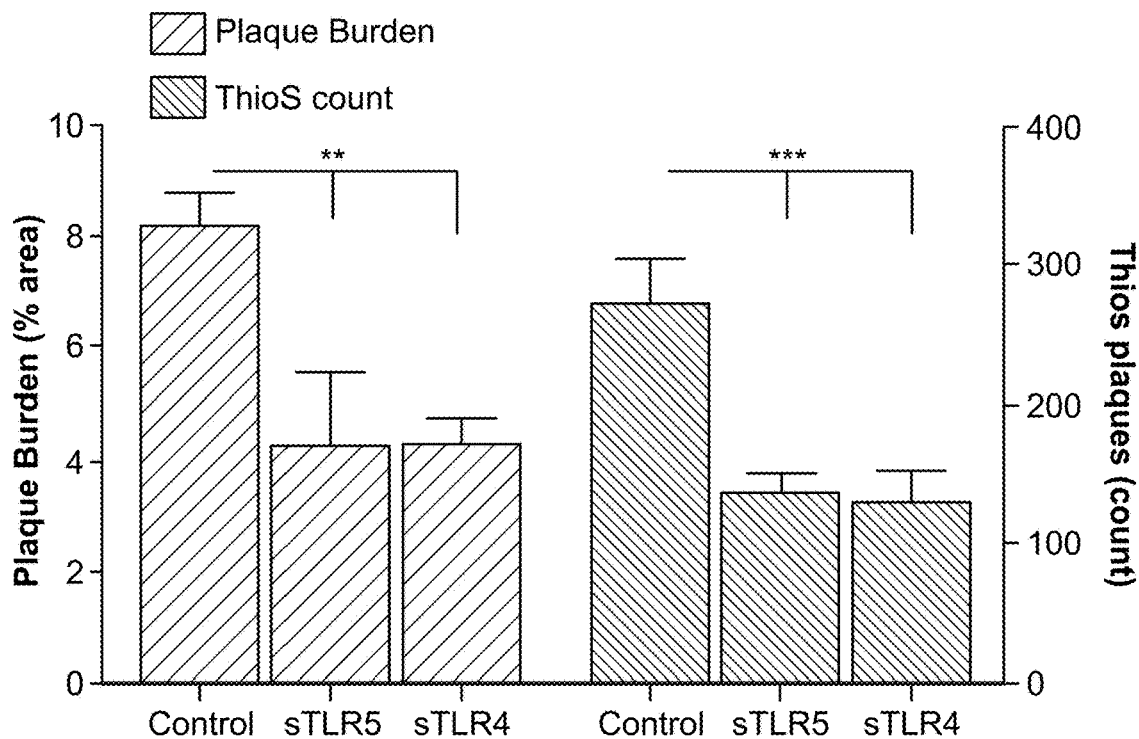
Figure 5:
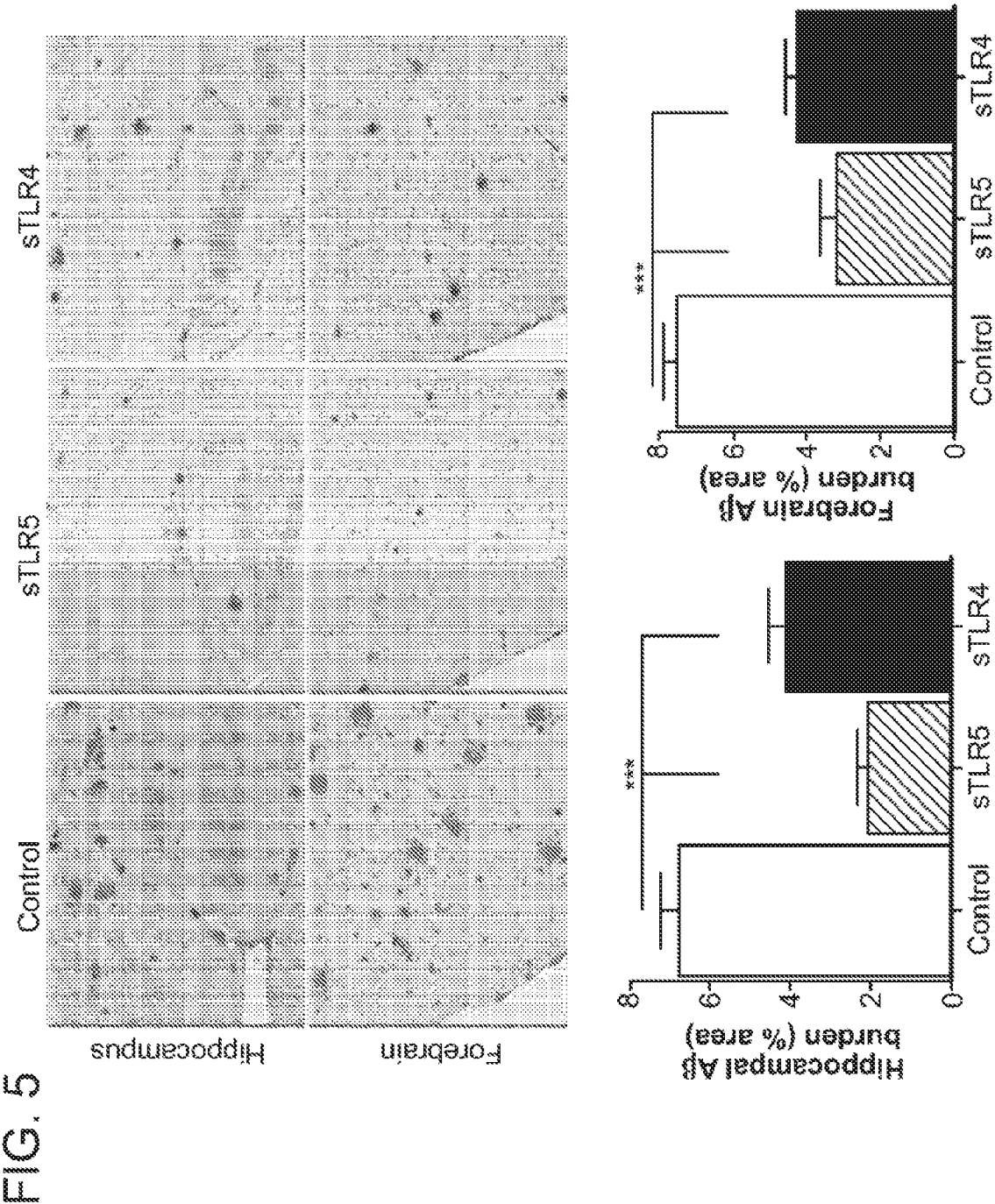
FIG. 5 depicts the effect of sTLR4 and 5 on plaque loads in APP overexpressing TgCRND8 mice. Both sTLR4 and 5 effectively reduced amyloid plaque loads in the forebrain and hippocampus of CRND8 mice at 5 months of age. Plaques were stained with 33.1.1 antibody (T Golde) and visualized using di-aminobenzidine (top panel). Plaque burden was counted using the pixel count program in Scanscope (Aperio) (bottom panel).
Figure 6:
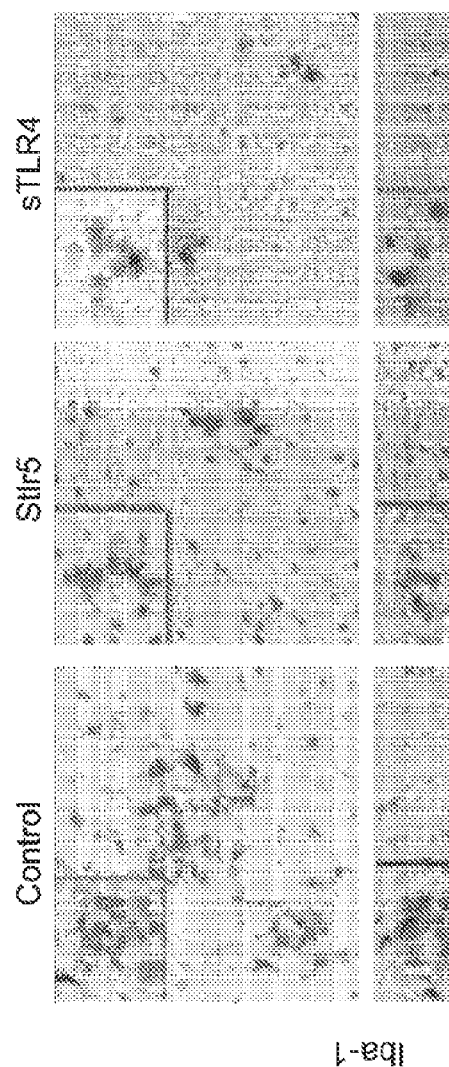
FIG. 6 depicts analysis of microglial activation in sTLR4 and sTLR5 expressing RND8 mice brains. Ibal immunoreactivity (marker for microglia) showed decrease plaque associated microglia in sTLR4 expressing CRND8 mice (top panel). Immunoblotting with cd1 1 b antibody showed reduced glial activation in sTLR4-CRND8 mice whereas the cd11 b levels in sTLR5-CRND8 mice were not significantly altered compared to control CRND8 mice (bottom panel). Plaques are marked with asterisks. *p<0.05, n=4/group.
Figure 6:
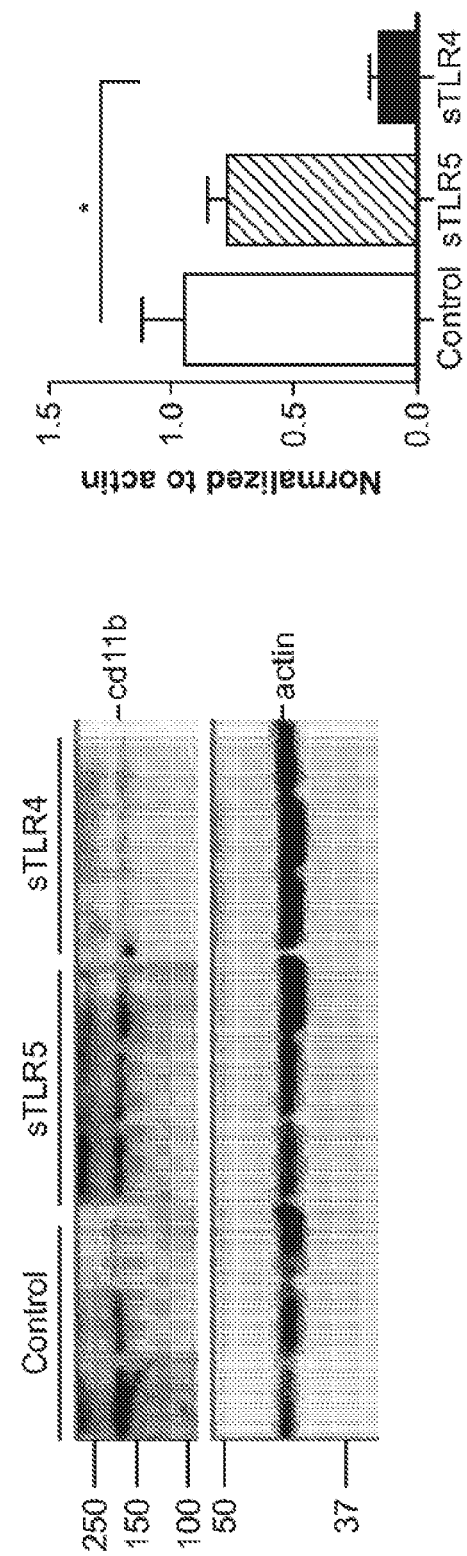
Figure 7:
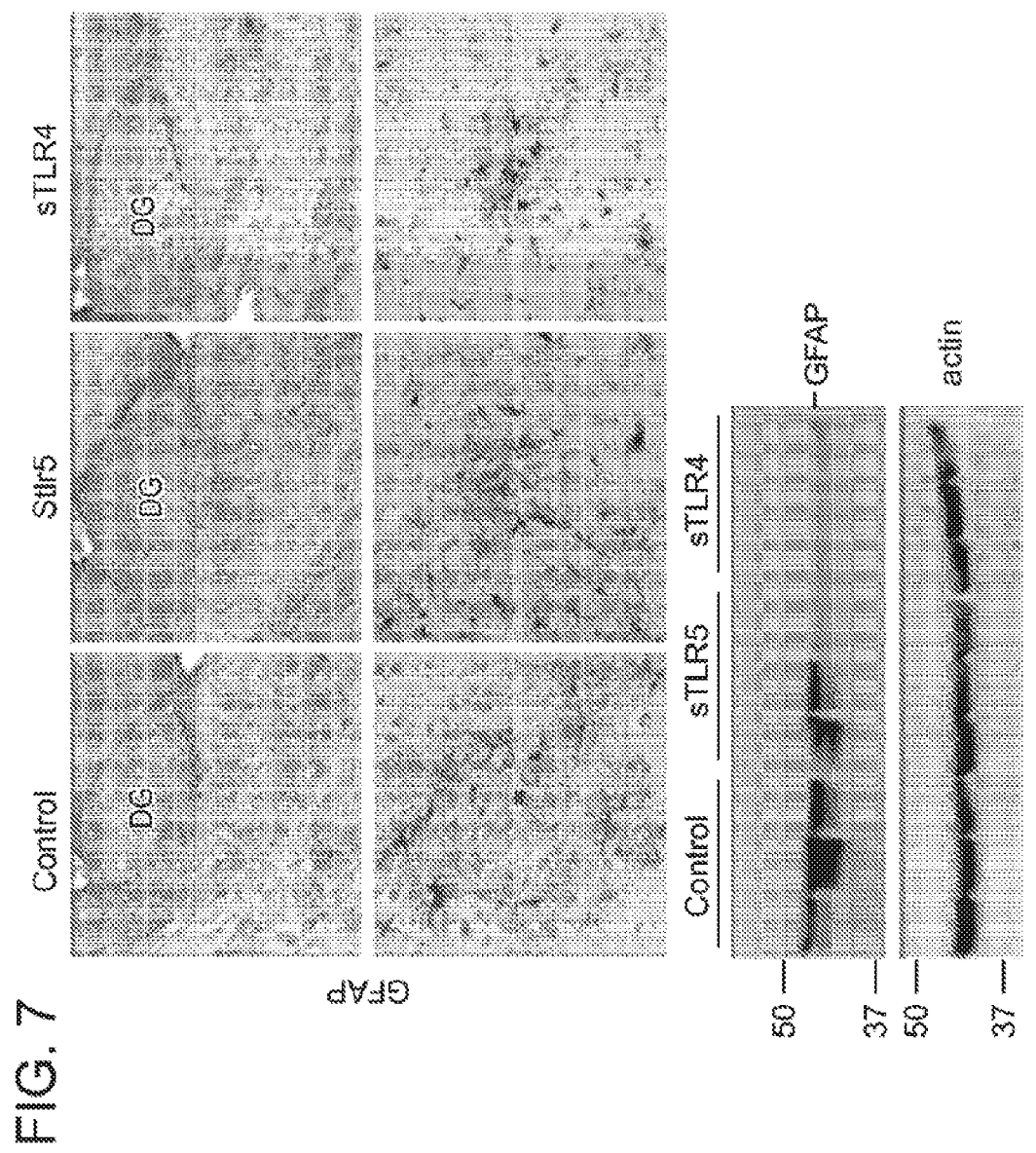
FIG. 7 shows analysis of astrocytic activation in sTLR4 and sTLR5 expressing CRND8 mice brains. GFAP immunoreactivity (marker for astrocyte) shows decreased plaque associated astrocyte in the hippocampus (DG, dentate gyrus) of sTLR4 expressing CRND8 mice (top panel). Higher magnification panels showing individual plaque associated astrocytosis is also shown. Immunoblotting with GFAP antibody showed reduced astrocytic presence in sTLR4-CRND8 mice whereas the GFAP levels in sTLR5-CRND8 mice were not significantly altered compared to control CRND8 mice (bottom panel). Plaques are marked with asterisks. *p<0.05, n=4/group.
Figure 8:
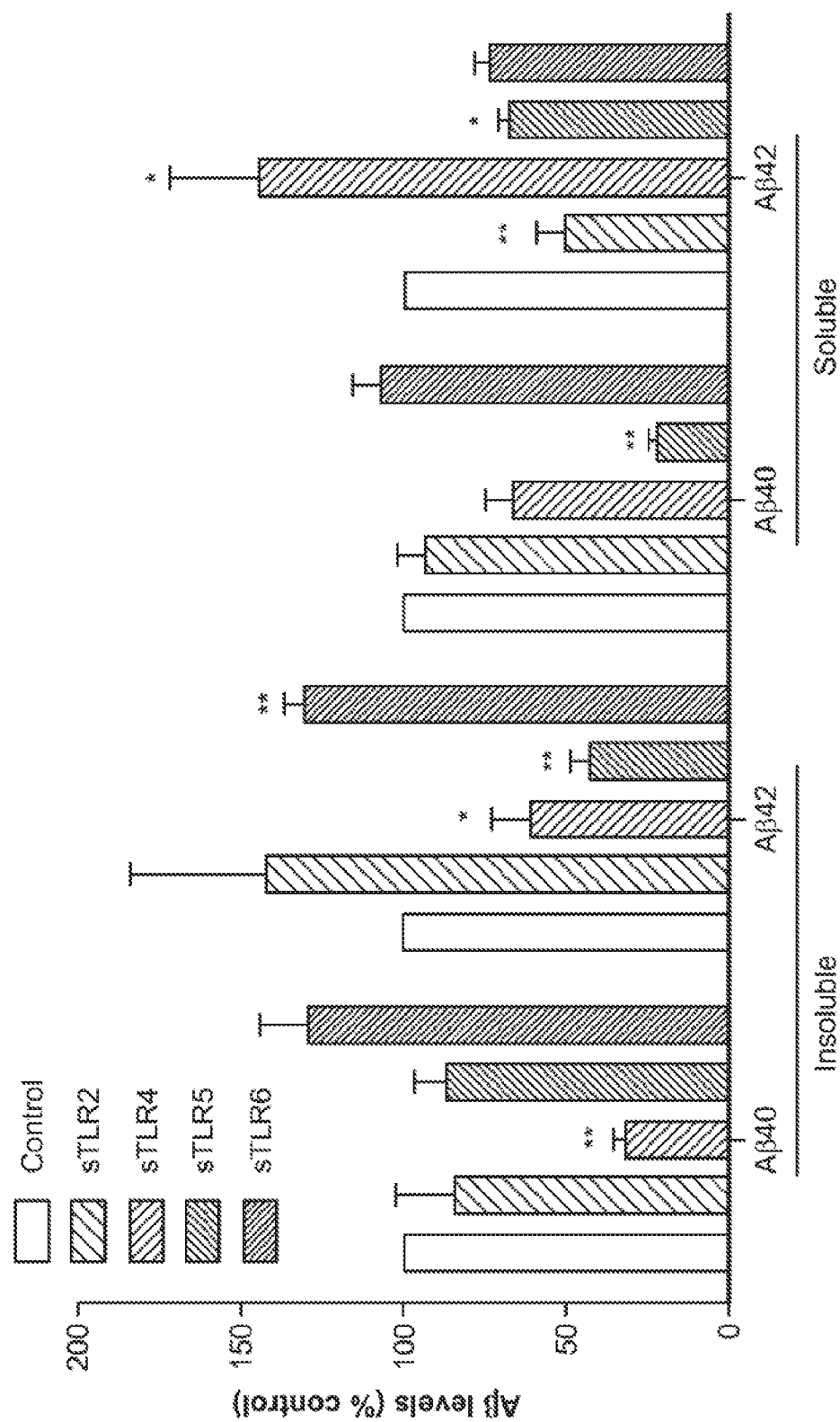
FIG. 8 is a graph depicting the effect of sTLRs on soluble and insoluble Aβ levels in 5 month old CRND8 mice. Quantification of effects of sTLRs 2, 4 and 5 on biochemical Aβ42 and Aβ40 loads were assessed by sandwich end-specific Aβ ELISA on brains sequentially extracted with RIPA, 2% SDS and 70% formic acid. Soluble fraction denotes SDS soluble Aβ and insoluble fraction denotes formic acid extractable Aβ. Aβ in the RIPA soluble fraction usually accounts for less than 1% of SDS soluble fraction. n=5/group; *p<0.05, **p<0.01, Two way ANOVA.
Figure 9:
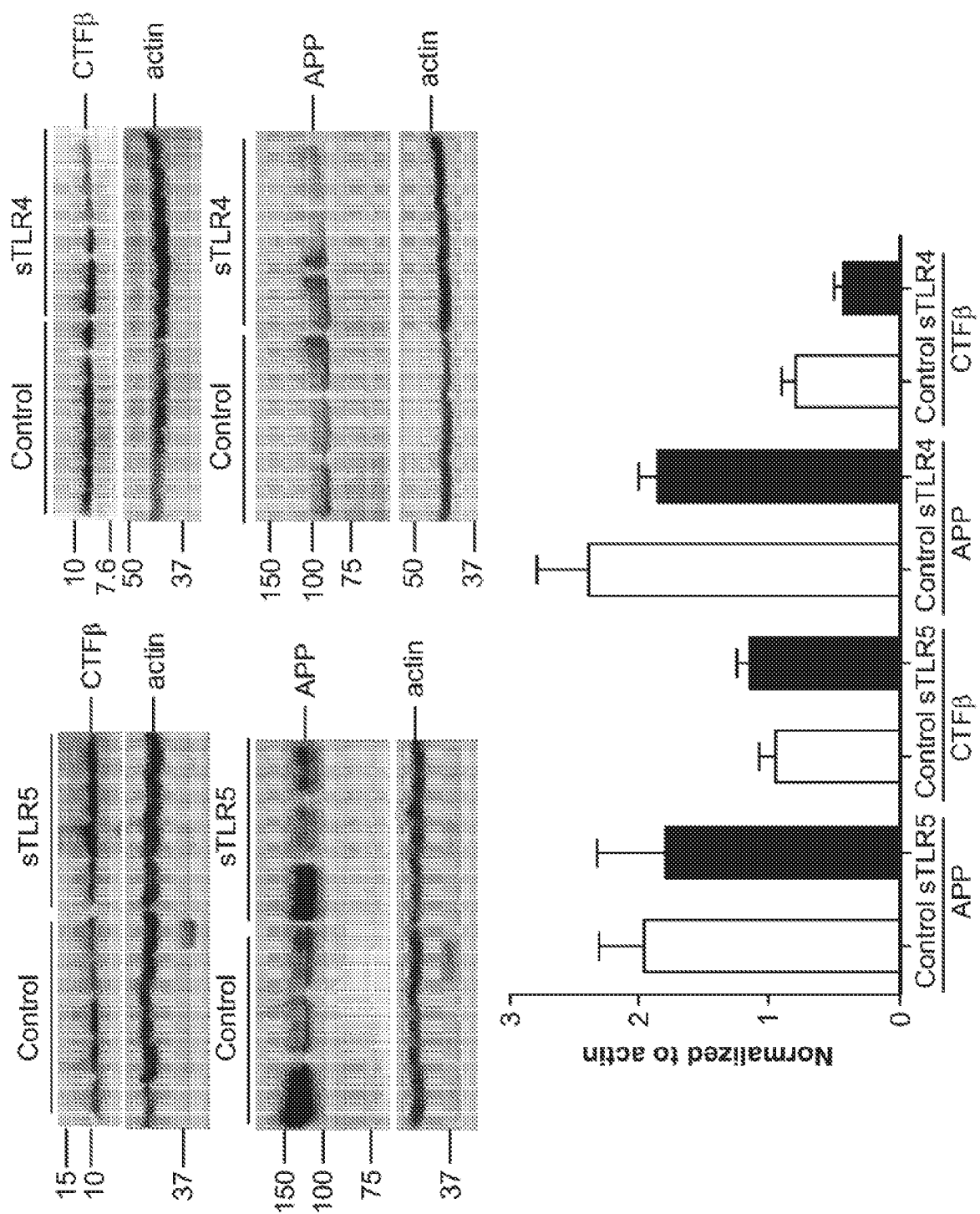
FIG. 9 depicts western blot analysis showing expression of sTLR4 or sTLR5 did not affect APP or CTF levels. RIPA soluble brain extracts of sTLR4-CRND8 and sTLR5-CRND8 were separated on SDS PAGE and probed with 82E1 (IBL International, for CTFβ) or CT20 (T Golde, for APP). The band intensity of individual proteins of interest was normalized to the internal control, β-actin. n=6/group, t test.

Recombinant AAV2/1 vectors encoding sTLRs 2, 4, 5 and 6 were used to transduce neonatal day P0 APP CRND8 mouse brain. Mice were aged to 5 months, brains were harvested and amyloid loads and gliosis were assessed. Expression of sTLR4 and 5 showed dramatic suppression of Aβ deposition (FIG. 4, FIG. 5) as well decreases in plaque associated microglia (FIG. 6) and astrocytes (FIG. 7). Both total plaque burden as well as total number of Thioflavin S cored plaques decreased in sTLR4 and sTLR5 expressing mice compared to controls (FIG. 4). Both sTLR4 and sTLR5 expression lowered biochemical insoluble Aβ levels (FIG. 8). On the other hand, sTLR2 did not significantly alter plaque burden or biochemical Aβ levels (FIG. 8). None of these sTLRs caused significant changes in APP or CTF levels (FIG. 9). A significant finding was that sTLR4 and sTLR5 expression also resulted in decreased over all gliosis, as assessed by Iba-1 (FIG. 6) and GFAP (FIG. 7) immunohistochemistry and cd11b (FIG. 6) and GFAP (FIG. 7) immunoblotting.

Figure 10:
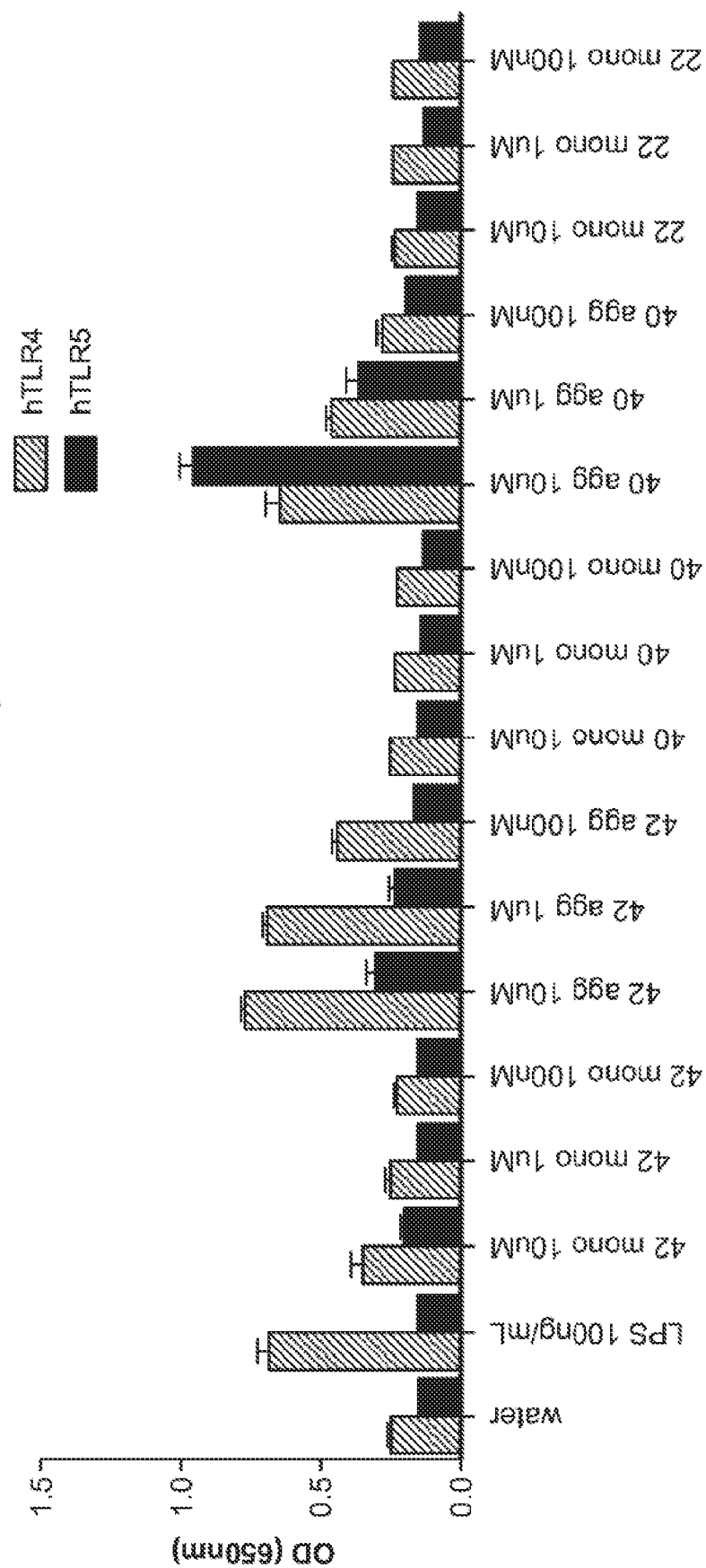
FIG. 10 is a graph depicting the effect of aggregated Aβ on TLR-SEAP assay. HEK-Blue TLR cells stably co-expressing human TLR4/MD-2gene or TLR5 gene and an NF-κB-inducible SEAP (secreted embryonic alkaline phosphatase) reporter gene was used to test whether different forms of Aβ act as TLR ligands in vitro. Assay was performed as per manufacturer's protocol (Invivogen). TLR binding and intracellular signaling was monitored using the SEAP detection media QUANTI-Blue at OD 650 nm. LPS, lipopolysaccharide, mono, monomeric, agg, aggregated.
Figure 11:
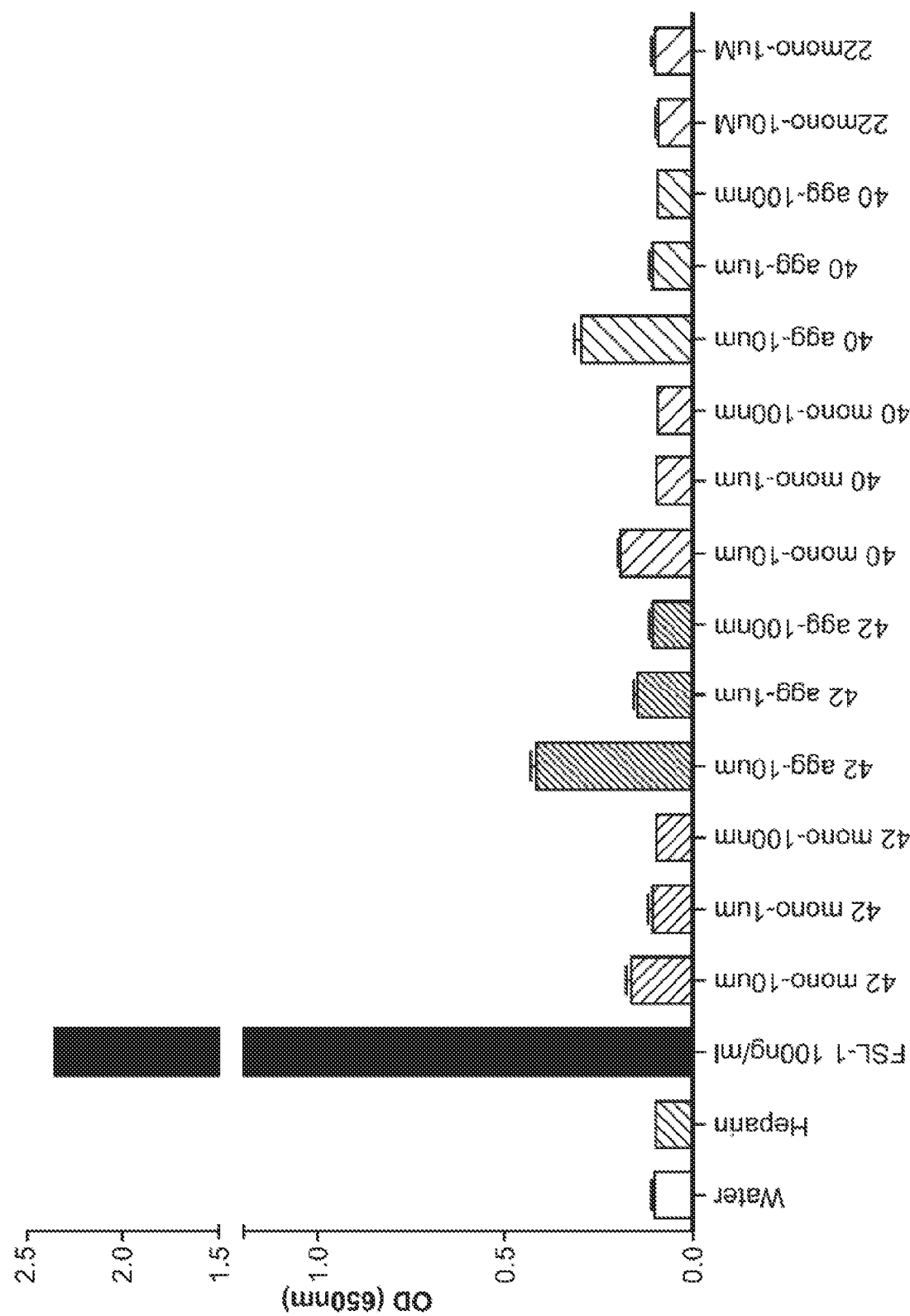
FIG. 11 is a graph depicting the effect of Aβ on TLR2-SEAP assay. HEK-Blue TLR cells stably co-expressing human TLR2 gene and an NF-κB-inducible SEAP (secreted embryonic alkaline phosphatase) reporter gene was used to test whether different forms of Aβ act as TLR ligands in vitro. Assay was performed as per manufacturer's protocol (Invivogen). TLR binding and intracellular signaling was monitored using the SEAP detection media QUANTI-Blue at OD 650 nm. FSL-1, synthetic diacetylated lipoprotein, mono, monomeric, agg, aggregated.
Figure 12:
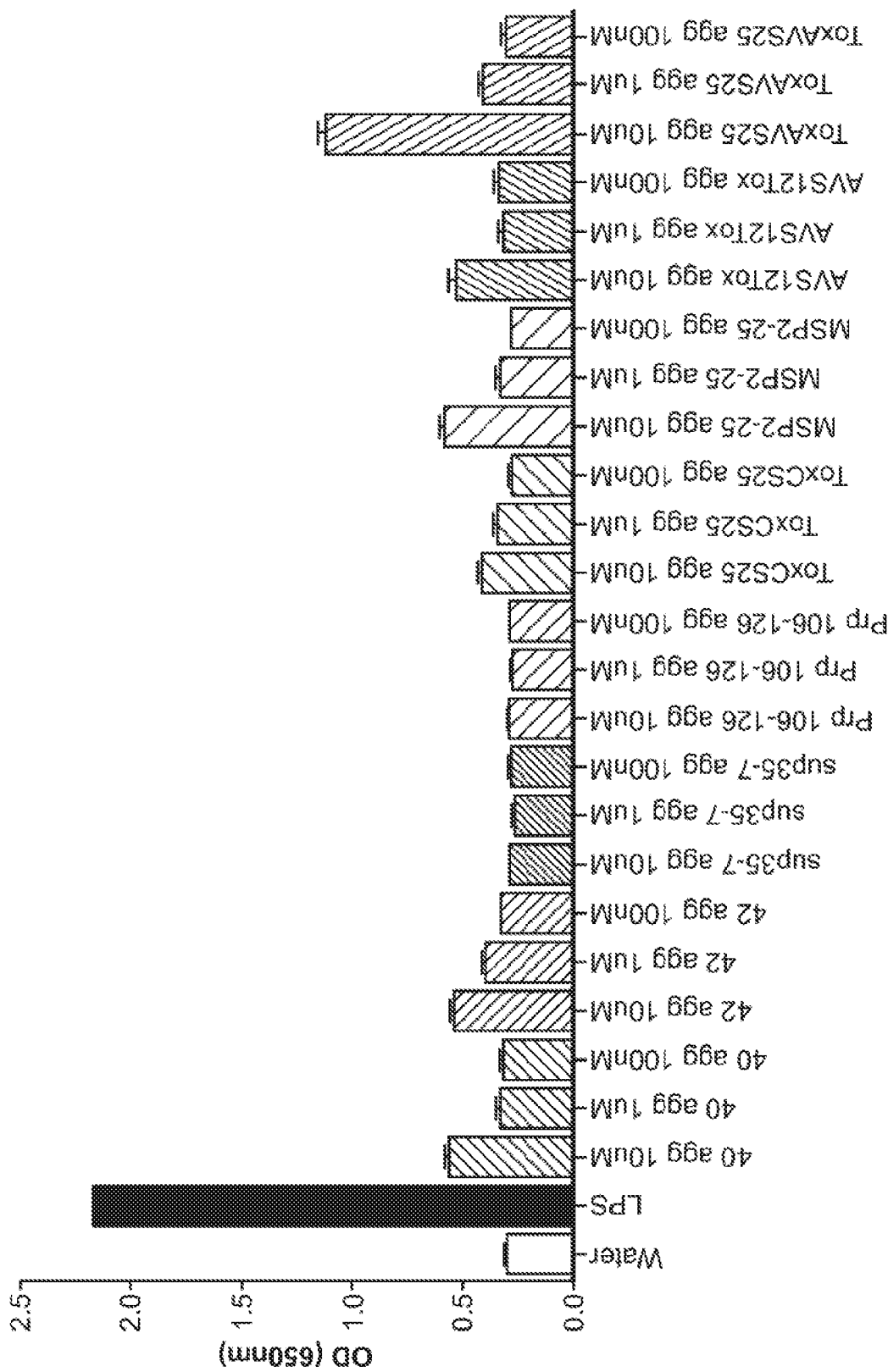
FIG. 12 is a graph depicting the effect of aggregated amyloid in TLR4-SEAP assay. HEK-Blue TLR cells stably co-expressing human TLR4/MD-2gene and an NF-κB-inducible SEAP (secreted embryonic alkaline phosphatase) reporter gene was used to test whether different species of 'heterologous' amyloid act as TLR ligands in vitro. Assay was performed as per manufacturer's protocol (Invivogen). TLR binding and intracellular signaling was monitored using the SEAP detection media QUANTI-Blue at OD 650 nm. LPS, lipopolysaccharide, agg, aggregated, 40, Aβ40, 42, Aβ42.

Whether toxic DAMPs, such as aggregated Aβ40, Aβ42, α-synuclein or tau acted as ligands of human TLRs and were capable of activating hTLRs was tested. In HEK293 cells stably co-expressing human TLR gene (TLR4/MD-2 or TLR5) and an NF-κB-inducible SEAP (secreted embryonic alkaline phosphatase) reporter gene, it was observed that these DAMPs had differential effect on TLR activation. Aβ42, Aβ40 (1 mg/ml California Peptide) were aggregated in vitro according to established protocols. Aggregated Aβ40 (but not aggregated Aβ42) bound and activated human TLR5 in a dose dependent manner whereas TLR4 mediated signaling was activated by both aggregated Aβ42 and aggregated Aβ40 (FIG. 10). Neither of the TLRs showed any activation in the presence of monomeric Aβ42 or monomeric Aβ40. A non-aggregatable Aβ construct Aβ1-22 ("22 mono") could not activate either TLR4 or 5. TLR2 activation was achieved to very modest levels only at the highest concentration of Aβ40 or 42 tested with no apparent dose-dependence activation, suggesting that Aβ does not elicit TLR2 signaling (FIG. 11). This agrees well with in vivo observations on the effect of sTLR2 overexpression in mouse brains (FIG. 8). Heterologous amyloids formed from other amyloidogenic proteins/peptides were also tested, some of which are not found in mouse or humans. These proteins were: sup 35-7 (from Sup35, a prion-like protein in yeast), prion protein fragment 106-126, Tox CS25 (Bacillus cold shock protein attached to T-helper toxoid peptide in the C terminal), MSP2 (Plasmodium merozoite surface protein 2), AVS12Tox (adenovirus type 2 shaft 12 amino acid peptide tagged to toxoid peptide on the C terminus) and ToxAVS25 (adenovirus type 2 shaft 25 amino acid peptide tagged to toxoid peptide on the N terminus). Of these different heterologous amyloids tested, ToxAVS12, AVS12Tox and MSP2 showed significant TLR4 activation) (FIG. 12).

Figure 13:
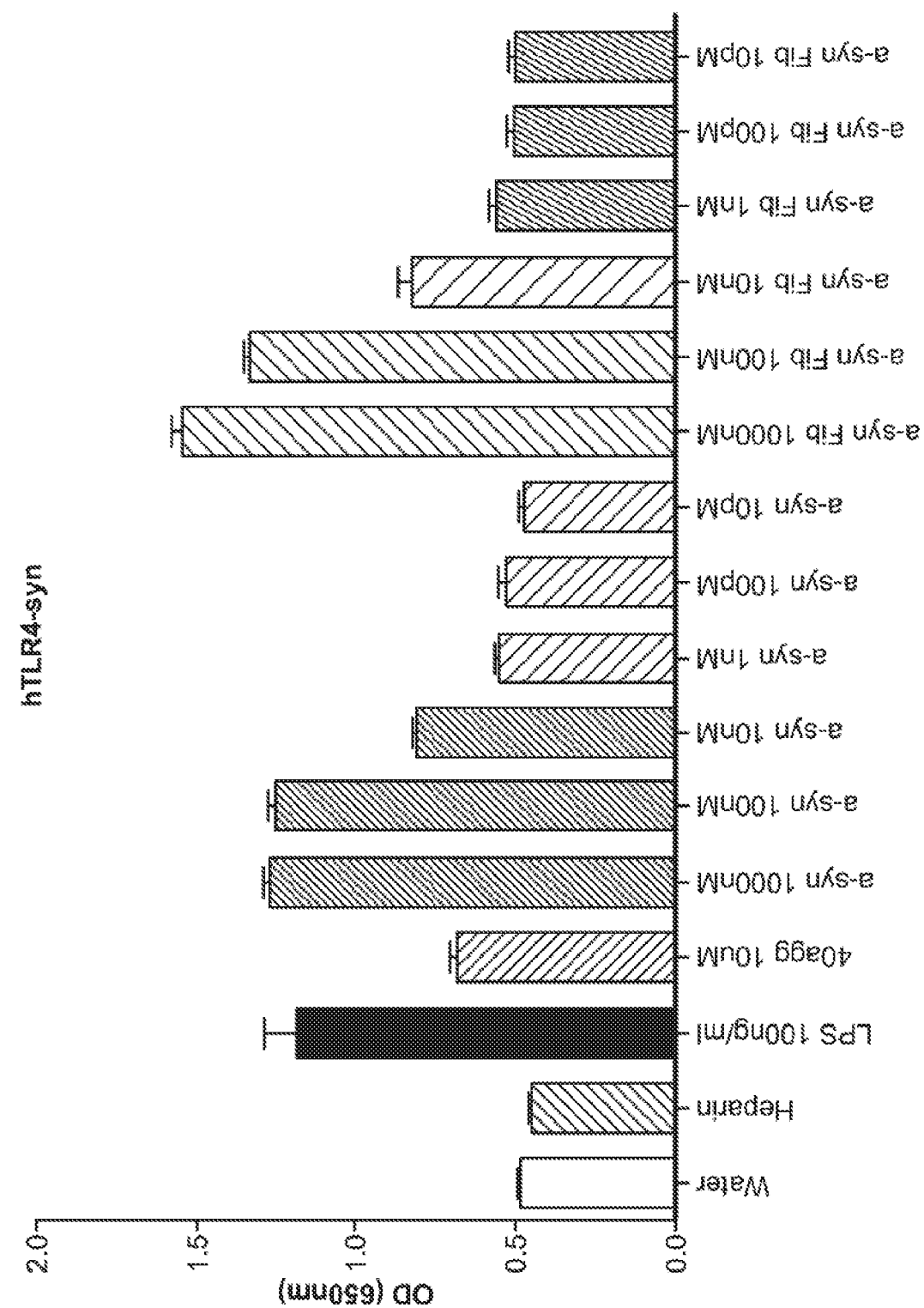
FIG. 13 is a graph depicting the effect of α-synuclein (a-syn) in TLR4-SEAP assay. HEK-Blue TLR cells stably co-expressing human TLR4/MD-2gene and an NF-κB-inducible SEAP (secreted embryonic alkaline phosphatase) reporter gene was used to test whether different forms of aggregated and monomeric synuclein act as TLR ligands in vitro. Assay was performed as per manufacturer's protocol (Invivogen). TLR binding and intracellular signaling was monitored using the SEAP detection media QUANTI-Blue at OD 650 nm. LPS, lipopolysaccharide, fib, fibrillar.
Figure 14B:
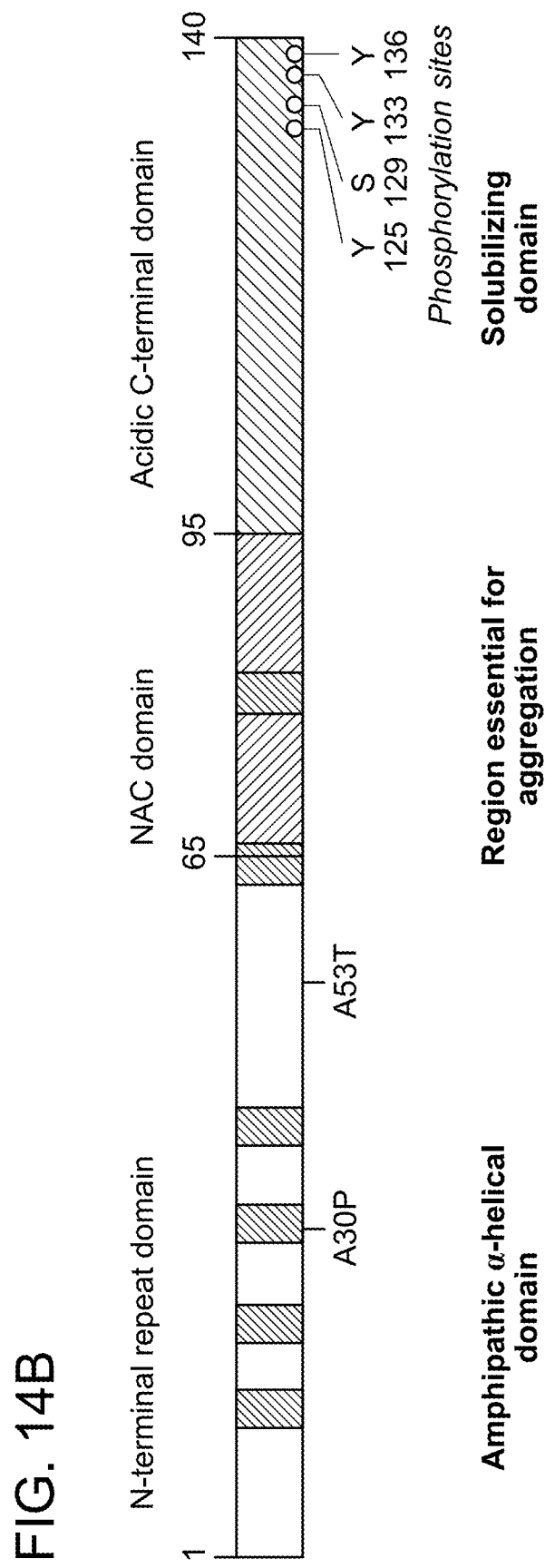
FIG. 14B is a schematic representation of monomeric α-synuclein, which contains an N-terminal repeat domain, NAC domain and acidic C-terminal domain.
Figure 15:
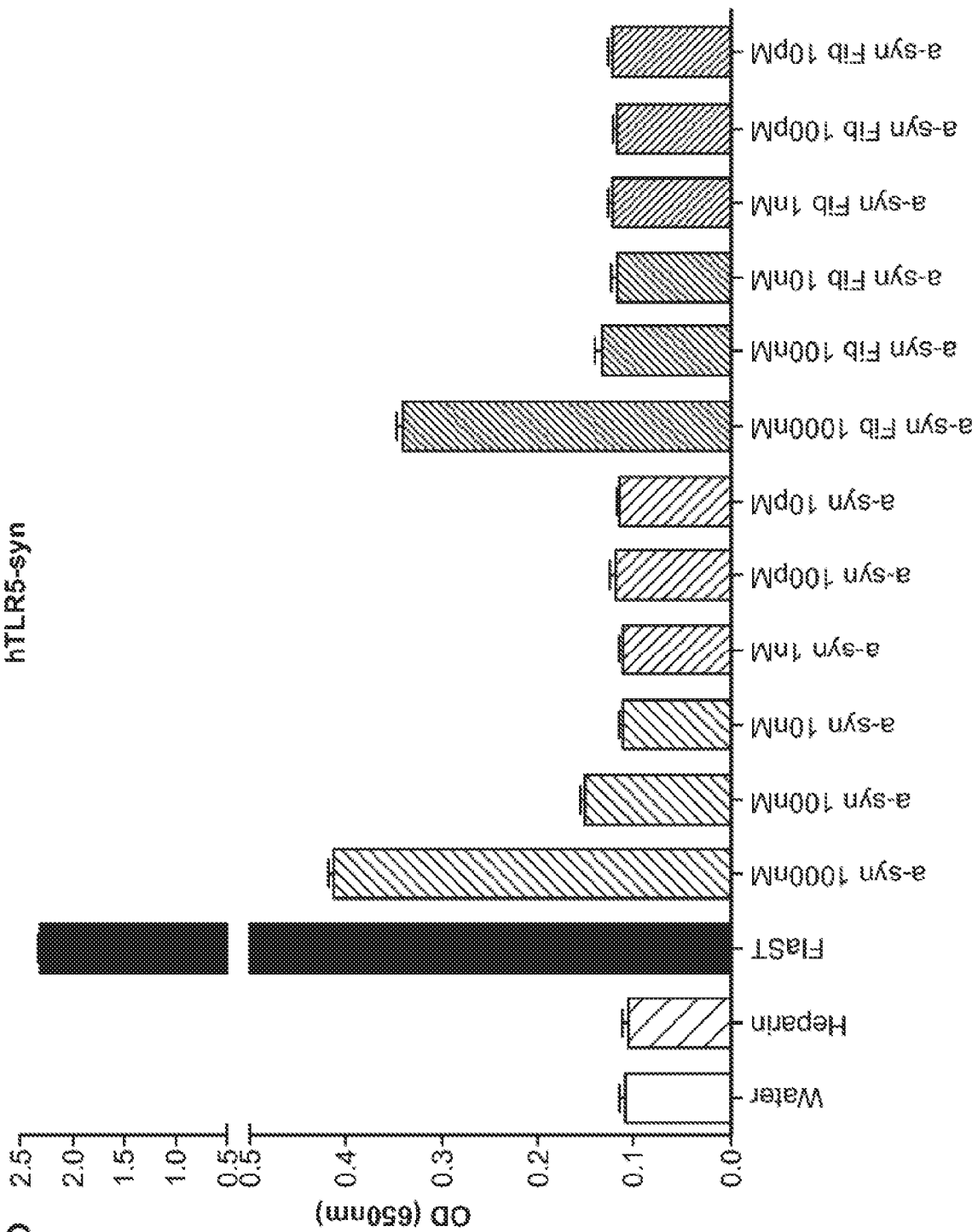
FIG. 15 is a graph depicting the effect of α-synuclein (a-syn) in TLR5-SEAP assay. HEK-Blue TLR cells stably co-expressing human TLR5 gene and an NF-κB-inducible SEAP (secreted embryonic alkaline phosphatase) reporter gene was used to test whether different fragments of monomeric and aggregated synuclein act as TLR ligands in vitro. Assay was performed as per manufacturer's protocol (Invivogen). TLR binding and intracellular signaling was monitored using the SEAP detection media QUANTI-Blue at OD 650 nm. FLA-ST, flagellin, mono, monomeric, fib, fibrillar (aggregated).
Figure 16:
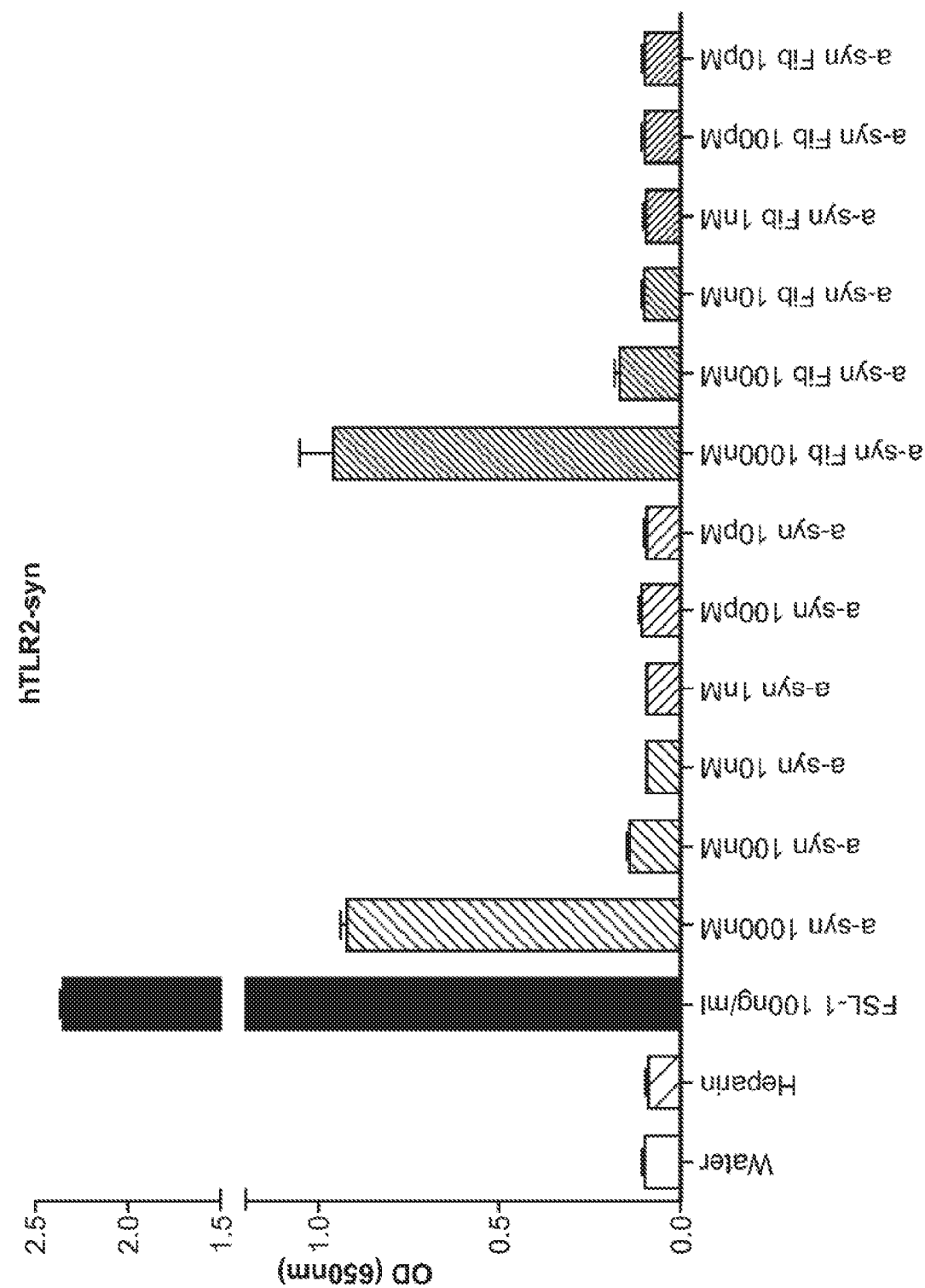
FIG. 16 is a graph depicting the effect of α-synuclein (a-syn) in TLR2-SEAP assay. HEK-Blue TLR cells stably co-expressing human TLR2 gene and an NF-κB-inducible SEAP (secreted embryonic alkaline phosphatase) reporter gene was used to test whether different fragments of monomeric and aggregated synuclein act as TLR ligands in vitro. Assay was performed as per manufacturer's protocol (Invivogen). TLR binding and intracellular signaling was monitored using the SEAP detection media QUANTI-Blue at OD 650 nm. FLA-ST, flagellin, fib, fibrillar (aggregated).

Synuclein (5 mg/ml) was aggregated in vitro according to established protocols. Aggregated as well as monomeric synuclein activated human TLR4 dramatically in a dose-dependent manner and activated TLR2 to a lesser extent at the highest concentration tested (FIGS. 13, 16). Synuclein weakly activated TLR5 signaling, only at the highest concentration tested (FIG. 15). A very interesting observation was that monomeric synuclein was also capable of eliciting TLR2, TLR4 and TLR5 signaling (FIGS. 13, 15). To test which sequence of monomeric synuclein actually can elicit TLR4 signaling, different peptides corresponding to internal and N-/C-terminal deletions were used (FIGS. 14A and 14B). The sequence deletion of amino acids 102-140 completely abolished TLR4 signaling whereas synuclein containing amino acids 1-110 was sufficient for TLR4 signaling. This indicates that the amino acids between 102 and 110 are important for synuclein mediated TLR4 activation.

Figure 17:
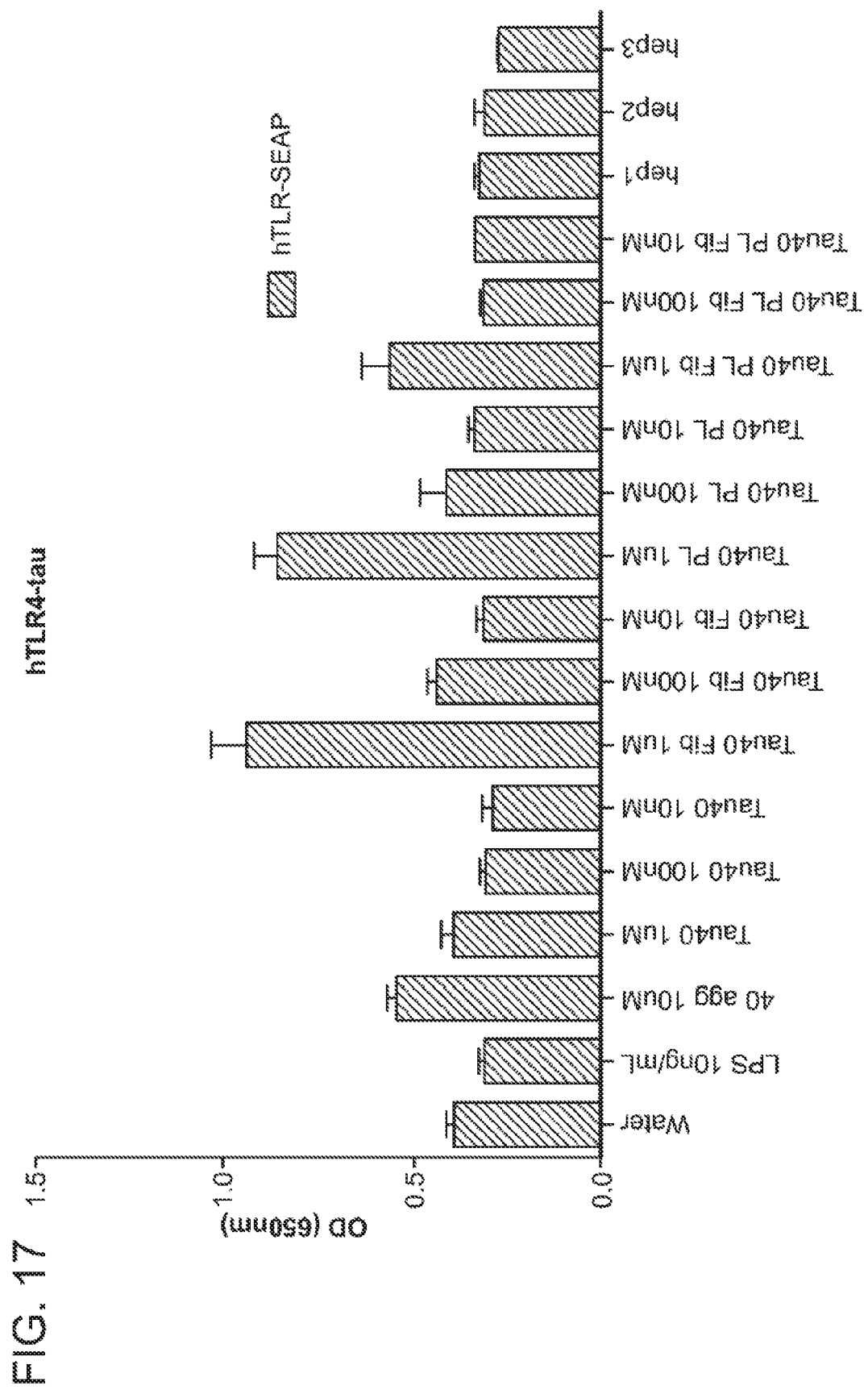
FIG. 17 is a graph depicting the effect of tau in TLR4-SEAP assay. HEK-Blue TLR cells stably co-expressing human TLR4/MD-2 gene and an NF-κB-inducible SEAP (secreted embryonic alkaline phosphatase) reporter gene was used to test whether monomeric and fibrillar wild type (Tau40) and disease associated mutant tau (Tau40 PL) act as TLR ligands in vitro. Assay was performed as per manufacturer's protocol (Invivogen). TLR binding and intracellular signaling was monitored using the SEAP detection media QUANTI-Blue at OD 650 nm. LPS, lipopolysaccharide, fib, fibrillar (aggregated).
Figure 18:
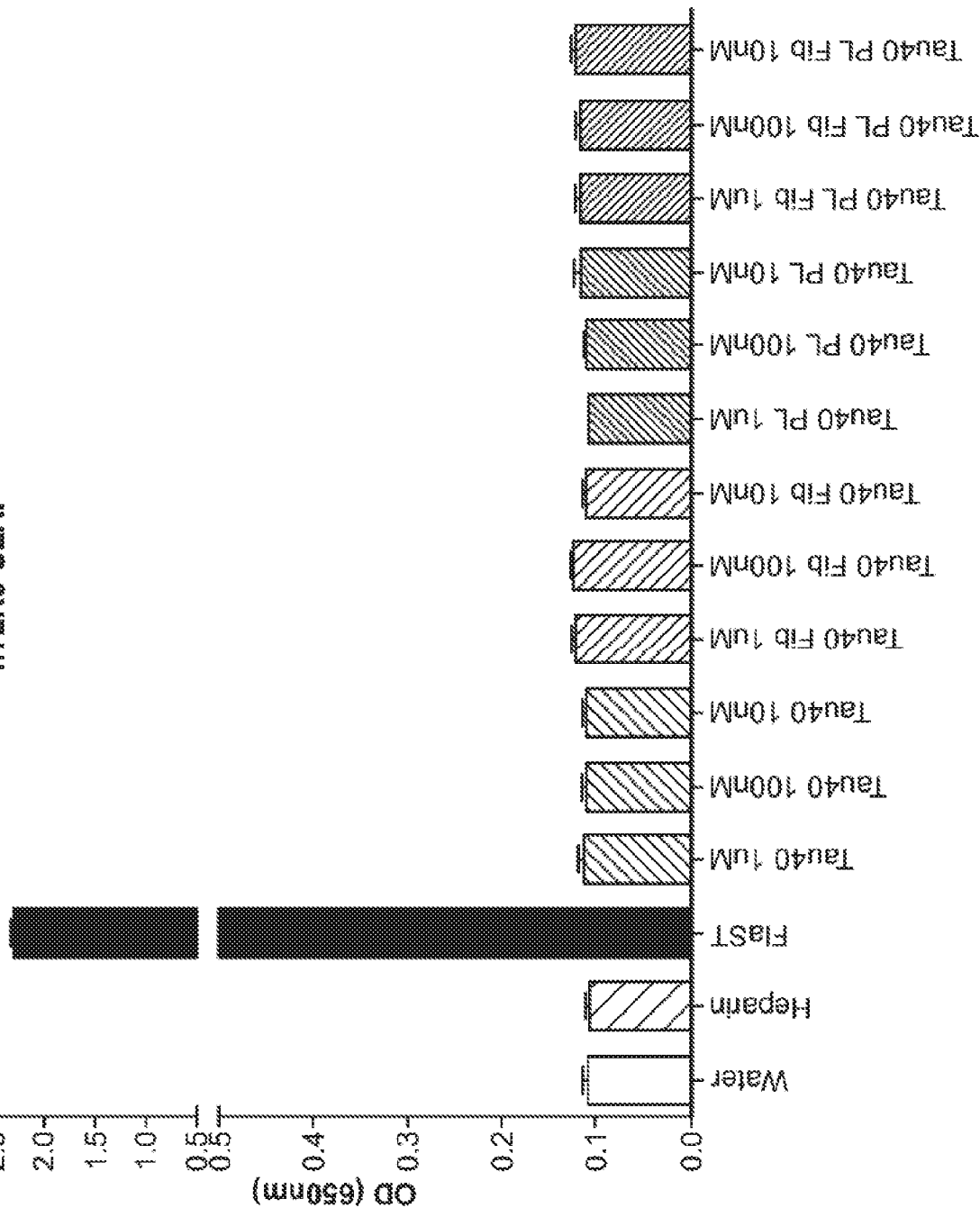
FIG. 18 is a graph depicting the effect of synuclein in TLR5-SEAP assay. HEK-Blue TLR cells stably co-expressing human TLR5 gene and an NF-κB-inducible SEAP (secreted embryonic alkaline phosphatase) reporter gene was used to test whether different fragments of monomeric and aggregated tau act as TLR ligands in vitro. Assay was performed as per manufacturer's protocol (Invivogen). TLR binding and intracellular signaling was monitored using the SEAP detection media QUANTI-Blue at OD 650 nm. FLA-ST, flagellin, fib, fibrillar (aggregated).
Figure 19:
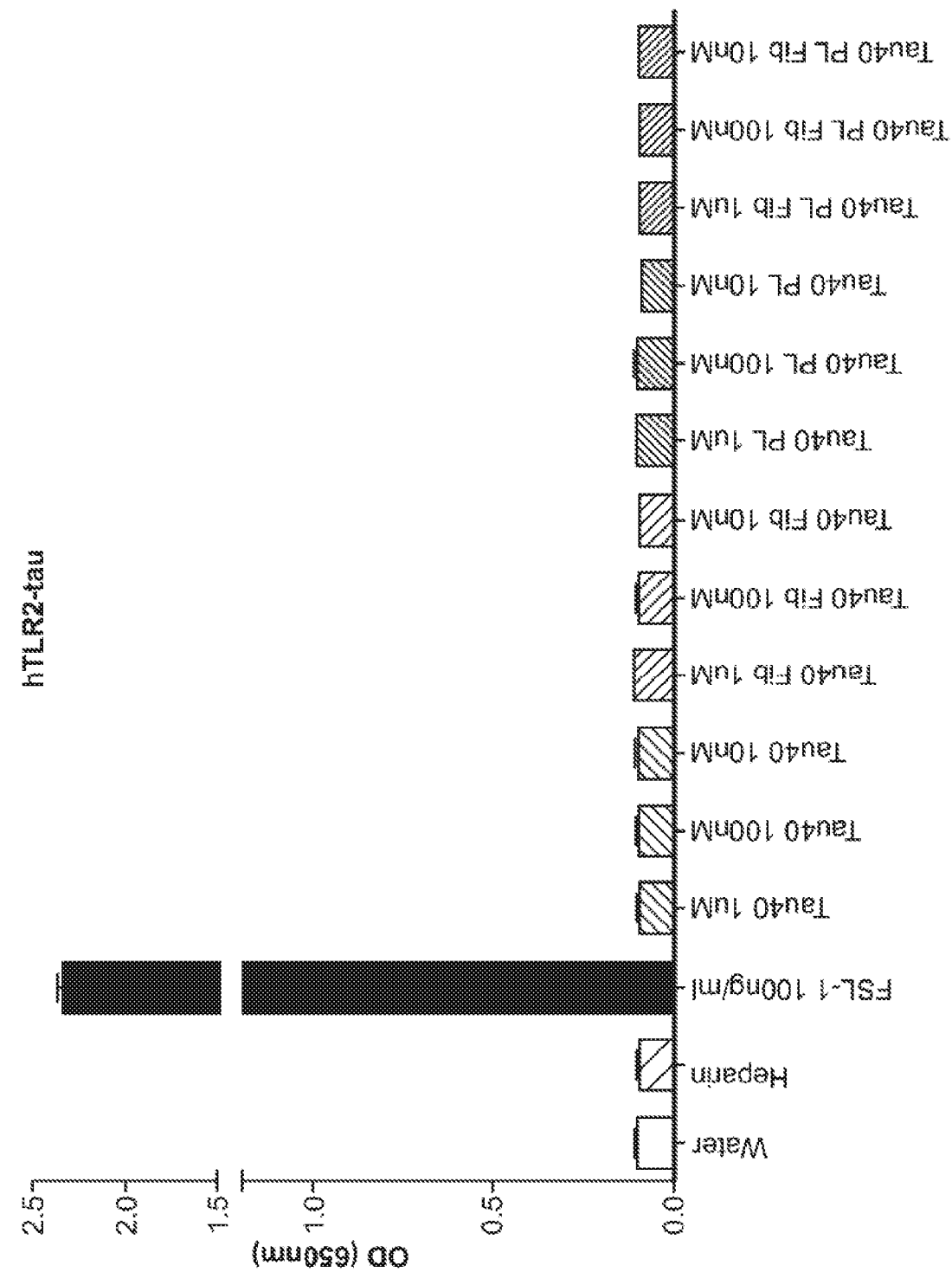
FIG. 19 is a graph depicting the effect of tau in TLR2-SEAP assay. HEK-Blue TLR cells stably co-expressing human TLR2 gene and an NF-κB-inducible SEAP (secreted embryonic alkaline phosphatase) reporter gene was used to test whether monomeric and fibrillar wild type (Tau40) and disease associated mutant tau (Tau40 PL) act as TLR ligands in vitro. Assay was performed as per manufacturer's protocol (Invivogen). TLR binding and intracellular signaling was monitored using the SEAP detection media QUANTI-Blue at OD650 nm. FSL-1, synthetic diacetylated lipoprotein, fib, fibrillar (aggregated).

Wild type tau T40 and disease associated mutant tau P301L ('Tau 40 PL') was fibrillized in the presence of heparin according to established protocols (Gias son, 2003). Neither monomeric wild type T40 nor heparin by itself activated human TLR4 or human TLR5 signaling (FIGS. 17-19). Aggregated wild type T40, aggregated T40 PL as well as monomeric T40PL could lead to TLR4 activation and signaling (FIG. 17), whereas none of these tau species tested activated either TLR5 or TLR6. Altogether, these experiments show that these proteins/peptides associated with different neurodegenerative diseases had very unique and distinct effects on TLR signaling, justifying their use as specific disease modifying tools targeting unique pathologic proteinopathic inclusions.

Whether expression of sTLRs can block Aβ and synuclein induced toxicity in primary mouse neuroglial cultures was also examined. In these studies, mouse neuroglial cultures were transduced with rAAV2/1 encoding sTLR2, 4 or 5, and after 7 days the cultures were exposed to aggregated Aβ42 (10 µM) or aggregated synuclein (1 µM) for 24 hours. In these studies both sTLR4 and 5 completely blocked Aβ-induced toxicity as assessed by PI/calcein cell viability assay (data not shown). sTLR2 could also block Aβ induced neurotoxicity but to a lesser extent. It was also tested whether these sTLRs could block α-synuclein induced neuronal death. sTLR2 and 4, but not sTLR5, were able to reverse α-synuclein induced cell death (data not shown), supporting the observations from the in vitro TLR activation assay (FIGS. 14-16).

The results indicated that: 1) sTLR 4 and 5 but not sTLR2 and 6 modulated Aβ plaque deposition in vivo, 2) sTLR 4 and 5 modulate plaque associated glial activation, 3) sTLR2, 4 and 5 blocked Aβ toxicity in primary neuronal cultures, 4) sTLR 2 and 4, but not sTLR5, blocked synuclein toxicity in primary neuronal culture, and 5) human full length TLR 2, 4 and 5 were differentially activated by Aβ, tau and synuclein.

Figure 20:
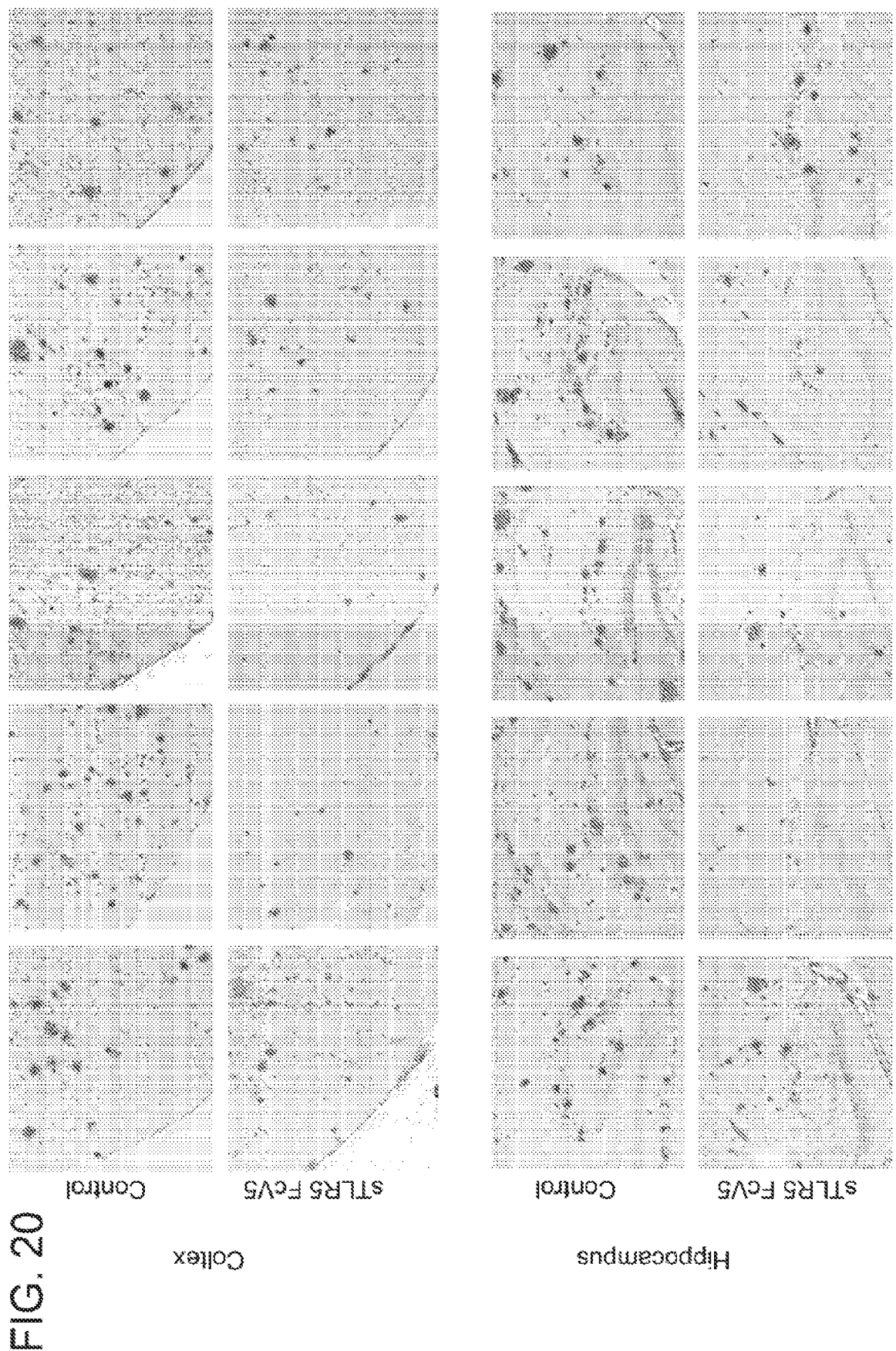
FIG. 20 shows that neonatal CRND8 mice injected with AAV2/1-sTLR5FcV5 or EGFP (Control) in the cerebral ventricles and then aged for 6 months, exhibited a striking reduction in Aβ cerebral plaque load in sTLR5FcV5-treated CRND8 mice, in both hippocampus and cortex sections.
Figure 21:
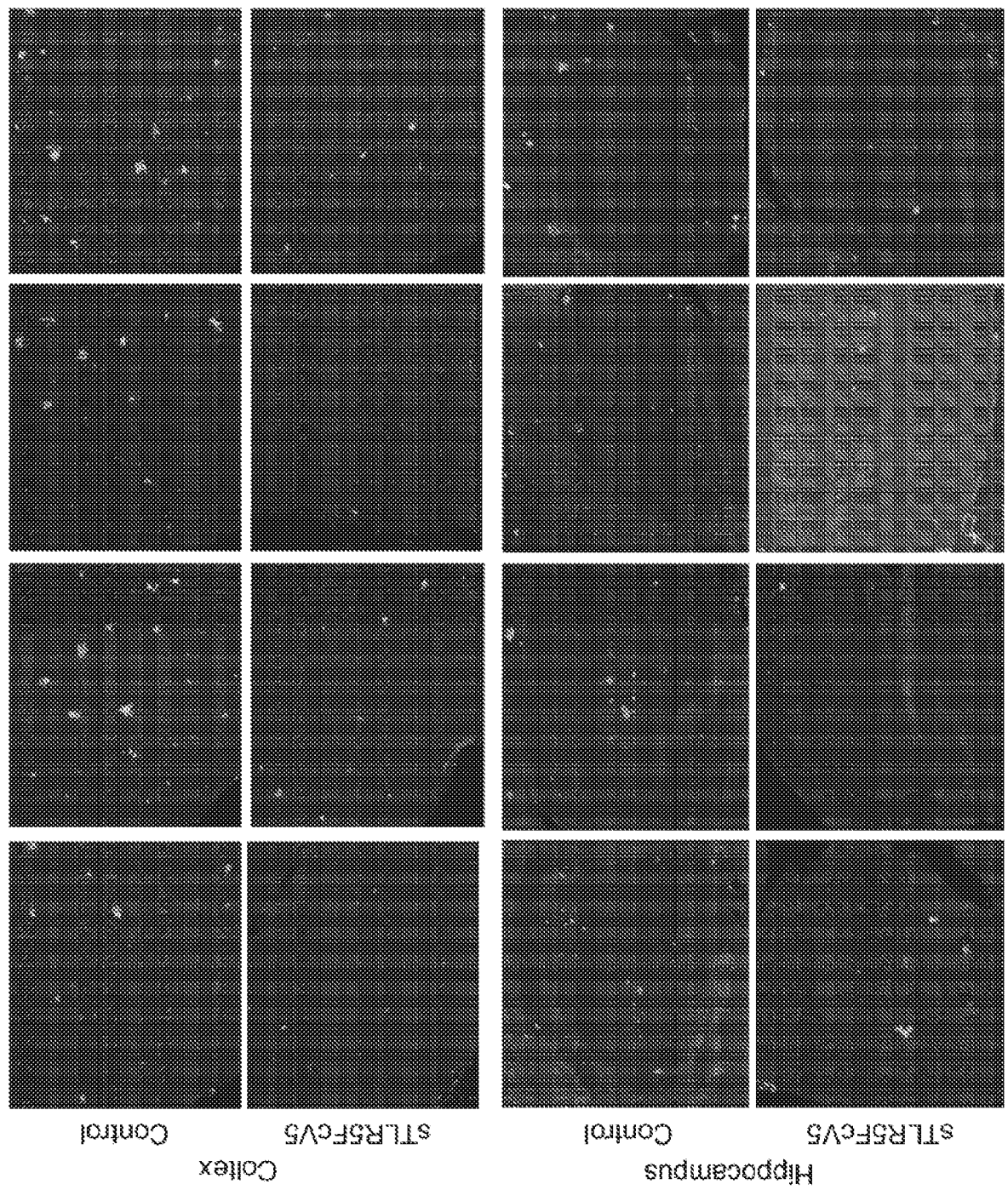
FIG. 21 shows that significant reductions in thioflavin S staining (thioflavin S labels beta-pleated sheets of plaques and neurofibrillary tangles (NFTs)) were seen in both hippocampus and cortex sections of neonatal CRND8 mice injected with AAV2/1-sTLR5FcV5 or EGFP (Control) in the cerebral ventricles and aged for 6 months.

Further experiments identified a striking reduction in Aβ cerebral plaque load in sTLR5FcV5-treated CRND8 mice. As shown in FIG. 20, when neonatal CRND8 mice were injected with AAV2/1-sTLR5FcV5 or EGFP (Control) in the cerebral ventricles and then aged for 6 months, post-sacrifice analysis of Aβ plaques in the hippocampus and cortex (stained with pan Aβ33.1.1 antibody) showed dramatic reduction in Aβ plaques in the sTLR5FcV5 injected mice, as compared to control mice (n=8-10 mice/group). Consistent with this reduction in Aβ plaques as ascertained by staining with pan Aβ33.1.1 antibody, a reduction in thioflavin S-stained Aβ plaques was also observed in CRND8 mice administered sTLR5FcV5. As shown in FIG. 21, significant reductions in thioflavin S staining (thioflavin S labels beta-pleated sheets of plaques and neurofibrillary tangles (NFTs)) were seen in neonatal CRND8 mice injected with AAV2/1-sTLR5FcV5 or EGFP (Control) in the cerebral ventricles and aged for 6 months. Analysis of Aβ plaques in the hippocampus and cortex (stained with Thioflavin S) showed reduced cored Aβ plaque in sTLR5FcV5 injected mice, as compared to control mice (n=8 mice/group). Thus, locally adminstered sTLR5FcV5 had a preventive effect upon the accumulation of Aβ plaques in CRND8 mice.

Figure 22:
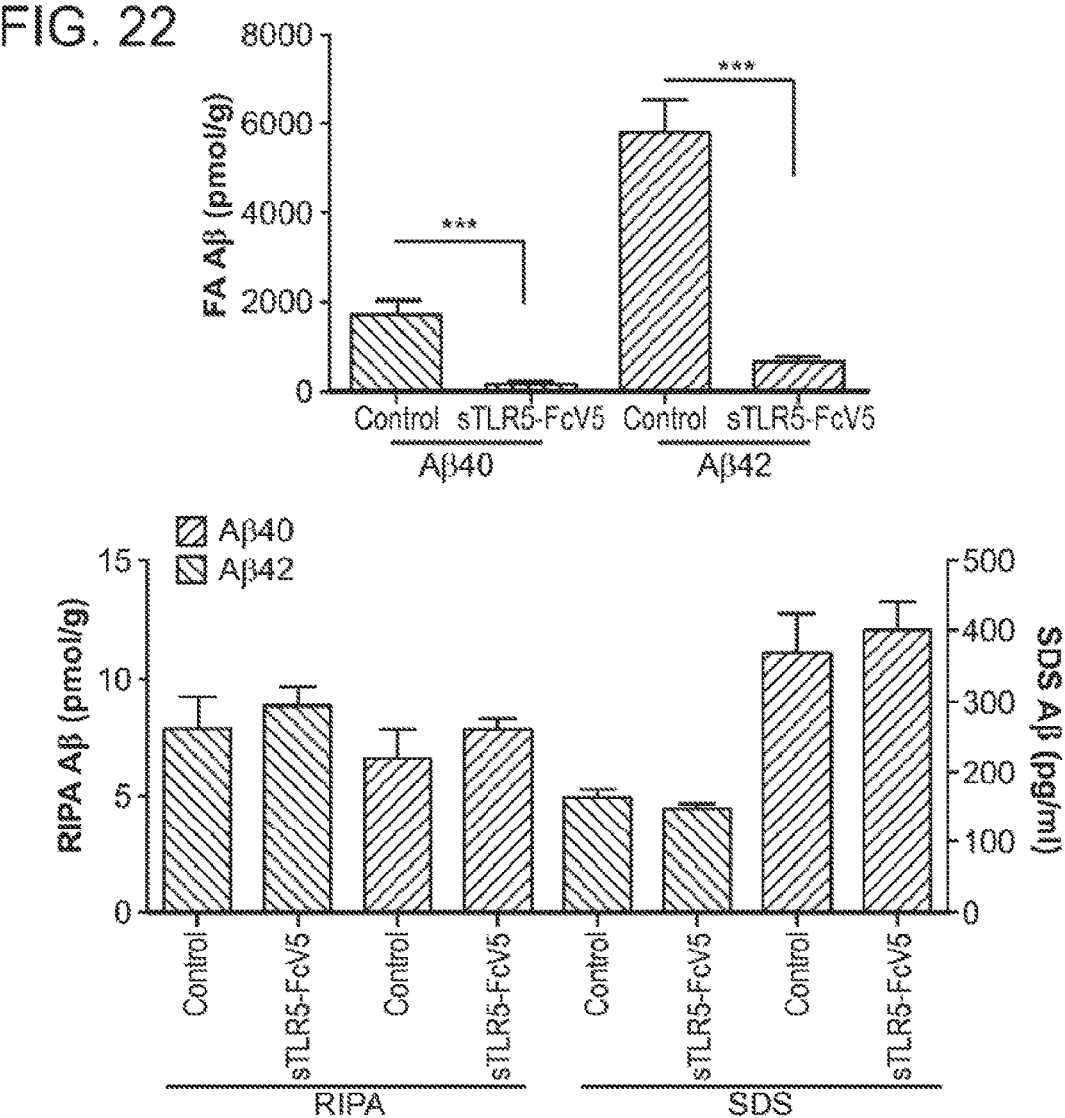
FIG. 22 demonstrates the selectivity of the sTLR5FcV5 effect for prevention and/or disruption of Aβ plaque deposits (extracted using formic acid (FA)), as opposed to impacting soluble forms of Aβ (extracted using RIPA or SDS), as observed in neonatal CRND8 mice that were injected with AAV2/1-sTLR5FcV5 or EGFP (Control) in the cerebral ventricles and aged for 6 months (n=8 mice/group; 1-way Anova, *p<0.05 and ***p<0.001).

The selectivity of the sTLR5FcV5 effect for prevention and/or disruption of Aβ plaque deposits, as compared to any impact upon soluble forms of Aβ, was examined in neonatal CRND8 mice that were injected with AAV2/1-sTLR5FcV5 or EGFP (Control) in the cerebral ventricles and aged for 6 months. As shown in FIG. 22, where Aβ levels in the forebrain were analyzed following serial extraction in formic acid (FA, representing amyloid plaque associated Aβ), RIPA (radio-immunoprecipitation assay) buffer or SDS (both RIPA and SDS results represent 'soluble' Aβ), there was a massive decrease in both FA-extracted Aβ42 and Aβ40 levels but no significant changes in RIPA- and SDS-extracted Aβ levels (n=8 mice/group; 1-way Anova, *p<0.05 and ***p<0.001). Thus, sTLR5FcV5 expression led to reduction in plaque-associated Aβ levels with a high level of selectivity of effect.

Example 2 sTLR5 FcV5 Produced a Survival Benefit in Alzheimer's Disease Model Mice

Figure 23:
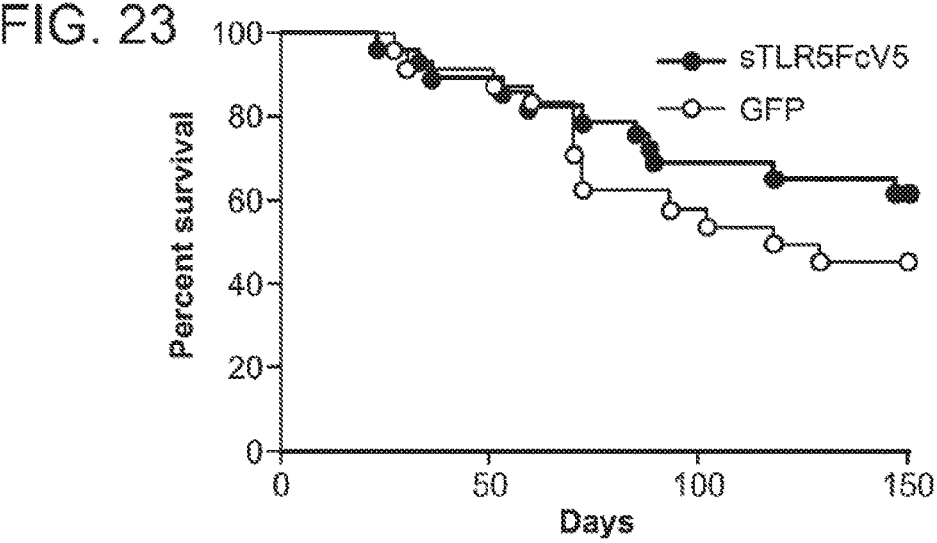
FIG. 23 shows that survival of transgenic CRND8 mice expressing either sTLR5FcV5 or EGFP (Control) was positively affected across a 150 day study by sTLR5FcV5 expression.

In view of the dramatic changes in Aβ plaque formation and disruption observed for sTLR5FcV5-administered mice, whether such changes also translated into a survival advantage for sTLR5FcV5-administered mice was examined. As shown in FIG. 23, survival was tracked in transgenic CRND8 mice expressing either sTLR5FcV5 or EGFP (Control). While high (approx. 80% or greater of the n=20-25 mice/group) rates of survival were observed in both groups over the first approximately 70 days, a dramatic and persistent divergence between the two groups was observed across the latter half of the study (FIG. 23). Thus, a greater proportion of sTLR5FcV5-expressing mice survived until the end of the 150 day study, indicating a survival benefit for sTLR5FcV5 expression.

Example 3

Figure 24:
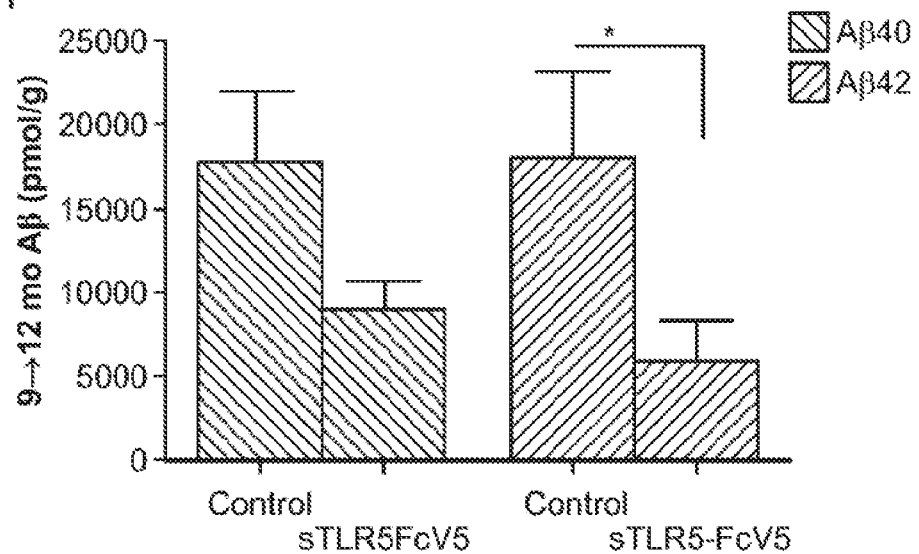
FIG. 24 shows that a sTLR5FcV5 treatment regimen performed via hippocampal expression for three months duration of sTLR5FcV5 (using rAAV2/1-sTLR5FcV5 or rAAV2/1-GFP as a control) in nine month old transgenic CRND8 mice resulted in reduced Aβ plaque levels, indicating a therapeutic effect of such sTLR5FcV5 treatment (n=5 mice/group. 1-way Anova, *p<0.05).

Therapeutic Impact of sTLR5 FcV5 Upon Aβ Plaques Confirmed in Alzheimer's Disease Model Mice To examine the impact of hippocampal expression of sTLR5FcV5 in non-neonatal CRND8 mice, nine month old transgenic CRND8 mice were injected in the hippocampus with rAAV2/1-sTLR5FcV5 or rAAV2/1-GFP and analyzed after three months. As shown in FIG. 24, this sTLR5 FcV5 treatment regimen resulted in reduced Aβ plaque levels. Specifically, analysis of formic acid-extracted Aβ levels in the hippocampus of the 9-12 month cohort showed reduced Aβ42 in sTLR5FcV5-injected mice, as compared to control mice. Meanwhile, there was no change in the RIPA and SDS soluble Aβ levels (data not shown; n=5 mice/group. 1-way Anova, *p<0.05). Thus, sTLR5 FcV5 had a therapeutic effect (as measured by Aβ plaque levels) upon nine month old CRND8 mice.

Example 4

Figure 25A:
FIGS. 25A and 25B demonstrate that overexpression of human sTLR5FcV5 in mouse brain via rAAV2/1 directed somatic brain transgenesis was confirmed via immunoprecipitation with anti-V5 antibody. The sTLR5FcV5 molecule containing the following regions is shown in FIG. 25A: (a) endogenous human TLR5 secretion signal, region (b) human TLR5 ectodomain, region (c) human IgG1 Fc domain and region (d) V5 molecular tag (regions are not to scale, and notations denote length of polypeptide (# amino acid)). Immunoprecipiation was used to examine expressed levels of human sTLR5FcV5 in neonatal CRND8 mice injected in the cerebral ventricles with either rAAV2/1-sTLR5FcV5 or rAAV2/1-GFP and aged to 6 months.
Figure 25B:
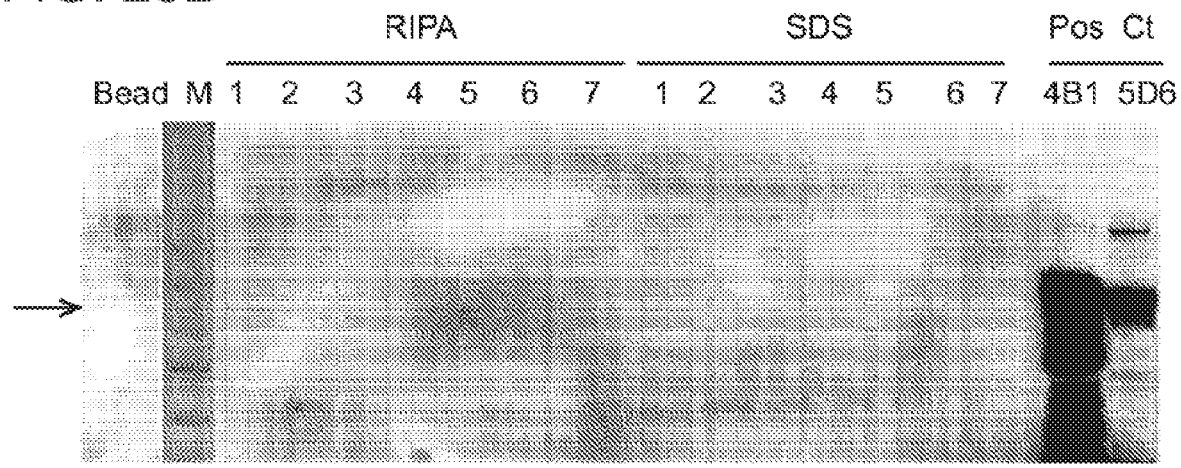

V5 Immunoprecipitation Confirmed the Overexpression of sTLR5FcV5 in Mice Administered sTLR5FcV5 Via rAAV2/1 Directed Somatic Brain Transgenesis Overexpression of human sTLR5FcV5 in mouse brain via rAAV2/1 directed somatic brain transgenesis was confirmed via immunoprecipitation with anti-V5 antibody. The sTLR5FcV5 molecule containing the following regions is shown in FIG. 25A: (a) endogenous human TLR5 secretion signal, region (b) human TLR5 ectodomain, region (c) human IgG1 Fc domain and region (d) V5 molecular tag (regions are not to scale, and notations denote length of polypeptide (# amino acid)). Immunoprecipitation was used to examine expressed levels of human sTLR5FcV5 in neonatal CRND8 mice injected in the cerebral ventricles with either rAAV2/1-sTLR5FcV5 or rAAV2/1-GFP and aged to 6 months. As shown in FIG. 25B, presence of sTLR5FcV5 protein was tested in sequentially extracted RIPA soluble and detergent (2% SDS) soluble fractions using a V5 immunoprecipitation (IP) assay. (In such experiments, "Bead" lane indicates a mock IP assay; "M" lane indicates molecular weight standards (from top to bottom in kDa, 250, 150, 100, 75, 50, 37); lanes 1-3, rAAV2/1-sTLR5FcV5 injected brain lysates and lanes 4-7, rAAV2/1-GFP injected mice brain lysates; Pos Ct=positive control lanes to test efficiency of V5 IP assay; "4B1" lane was media from sTLR4FcV5-CHO clonal cell line and "5D6" lane was media from sTLR5FcV5-CHO clonal cell line.) The arrow in FIG. 25B corresponds to the expected molecular weight of sTLR5FcV5 protein, which was most prominently observed in RIPA-extracted lanes 1-3, as well as in positive control lanes (the "4B1" lane that contained media from the sTLR4FcV5-CHO clonal cell line and the "5D6" lane that contained media from the sTLR5FcV5-CHO clonal cell line). Thus, overexpression of human sTLR5FcV5 in mouse brain via rAAV2/1 directed somatic brain transgenesis was confirmed via immunoprecipitation.

Example 5 sTLR5FcV5 Bound to Aβ In Vivo and In Vitro

Figure 26B:
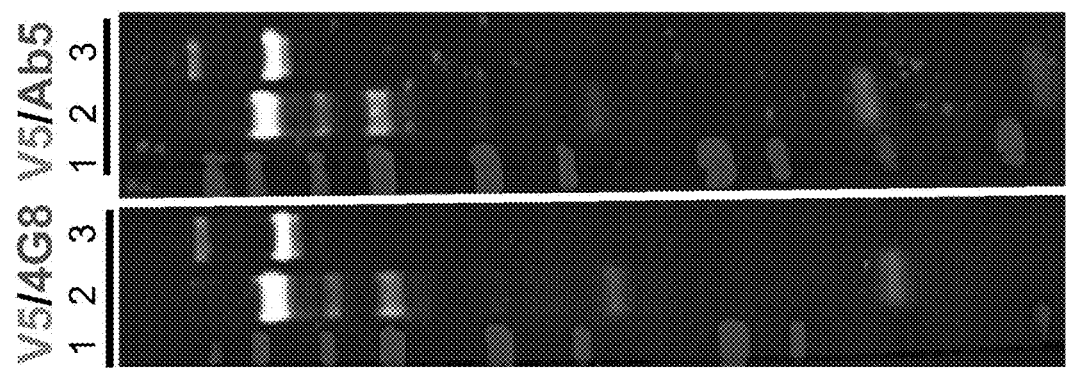
FIGS. 26A and 26B demonstrate that sTLR5FcV5 formed a complex with soluble Aβ in vivo.
Figure 26A:
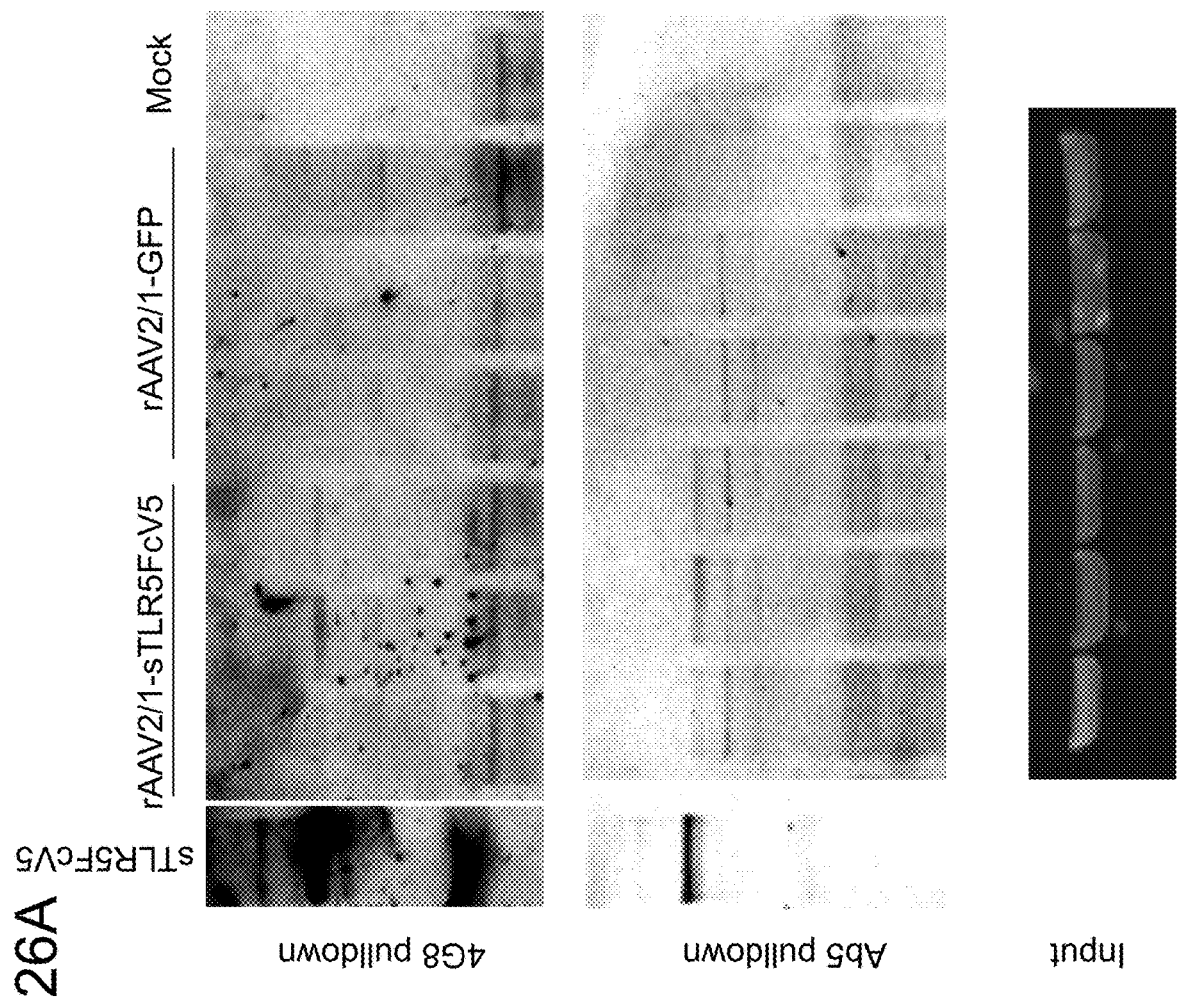

The dramatic impact of sTLR5FcV5 expression upon Aβ plaque levels indicated a direct effect of sTLR5FcV5 upon Aβ plaques. To examine whether sTLR5FcV5 might actually bind Aβ, a series of experiments (shown in FIGS. 26-29) was performed. Within the first such experiments, TBS-extracted soluble brain lysates obtained from 6 month old mice neonatally injected with rAAV2/1-sTLR5FcV5 or rAAV2/1-GFP were incubated with two different anti-Aβ antibodies bound to Sepharose beads: 4G8 (Covance) corresponding to amino acids 17-24 and Ab5 (T. Golde) corresponding to amino acids 1-16. After binding, immune complexes were then pulled down, separated on a SDS PAGE and tested for the presence of sTLR5FcV5 using anti V5 tag antibody. Such experiments demonstrated that sTLR5FcV5 formed a complex with soluble Aβ in vivo (FIG. 26A). (Meanwhile, a mock pulldown assay served as a negative control and a lane of purified sTLR5FcV5 protein was loaded at left to assist in molecular weight determination. Total inputs in each lane were assessed using an anti-actin antibody (FIG. 26A, lower panel).) As a further control, dual Li-Cor immunoblotting was used to show that neither purified sTLR5FcV5 nor purified sTLR4FcV5 was recognized by anti-Aβ antibodies 4G8 or Ab5 by themselves (FIG. 26B, where lanes 1 show molecular weight markers, lanes 2 show sTLR4FcV5 results and lanes 3 show sTLR5FcV5 results). Thus, sTLR5FcV5 bound Aβ in vivo.

Figure 27:
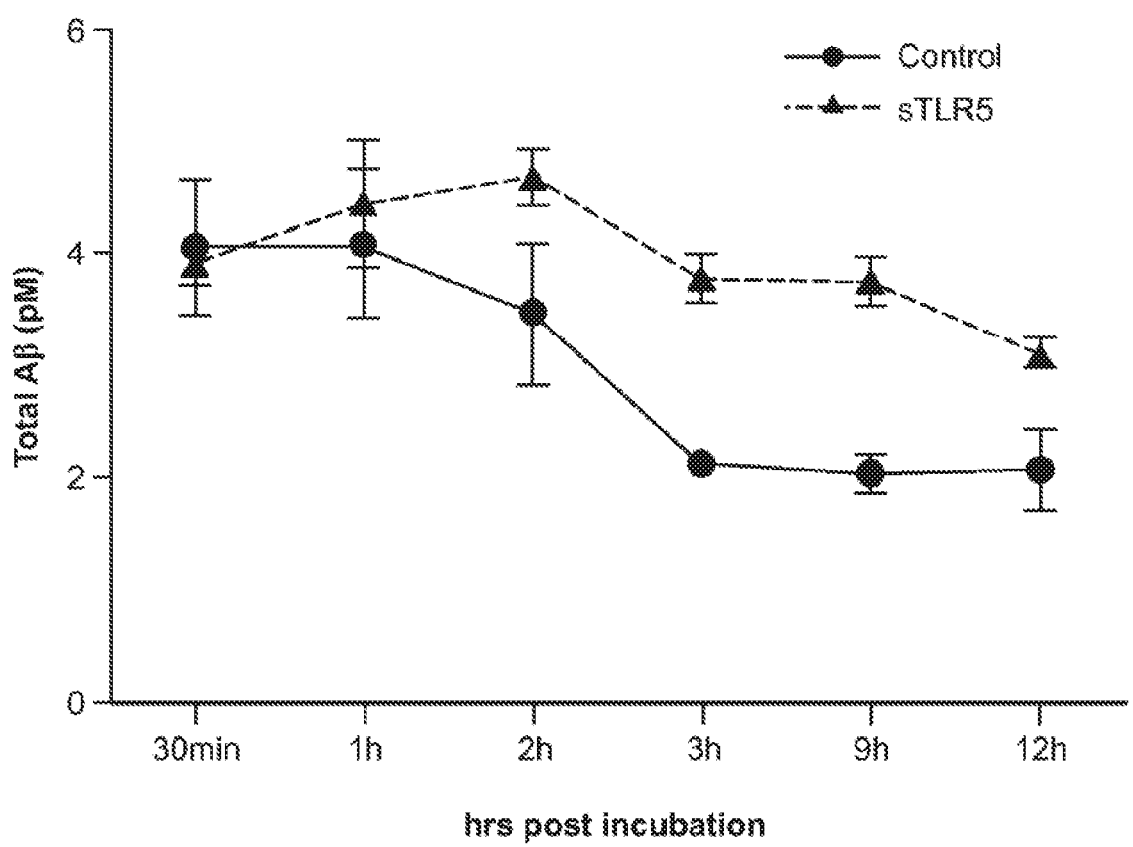
FIG. 27 shows that sTLR5FcV5 in the media of stable CHO cell lines expressing sTLR5FcV5, when incubated with aggregated Aβ42 for a 12 hour time course, bound Aβ42. ELISA analysis of Aβ in the media demonstrated that a proportionately higher amount of Aβ remained sequestered in sTLR5FcV5 media, as compared to control CHO cell media.

Initial in vivo observations of sTLR5FcV5-Aβ binding were then pursued in greater biochemical detail in vitro. In an initial in vitro experiment to detect sTLR5FcV5-Aβ binding, stable CHO cell lines expressing sTLR5FcV5 were incubated with aggregated Aβ42 for a 12 hour time course (FIG. 27). ELISA analysis of Aβ in the media demonstrated that a proportionately higher amount of Aβ remained sequestered in sTLR5FcV5 media, as compared to control CHO cell media. Thus, sTLR5FcV5 bound to aggregated Aβ42 in vitro.

Figure 28:
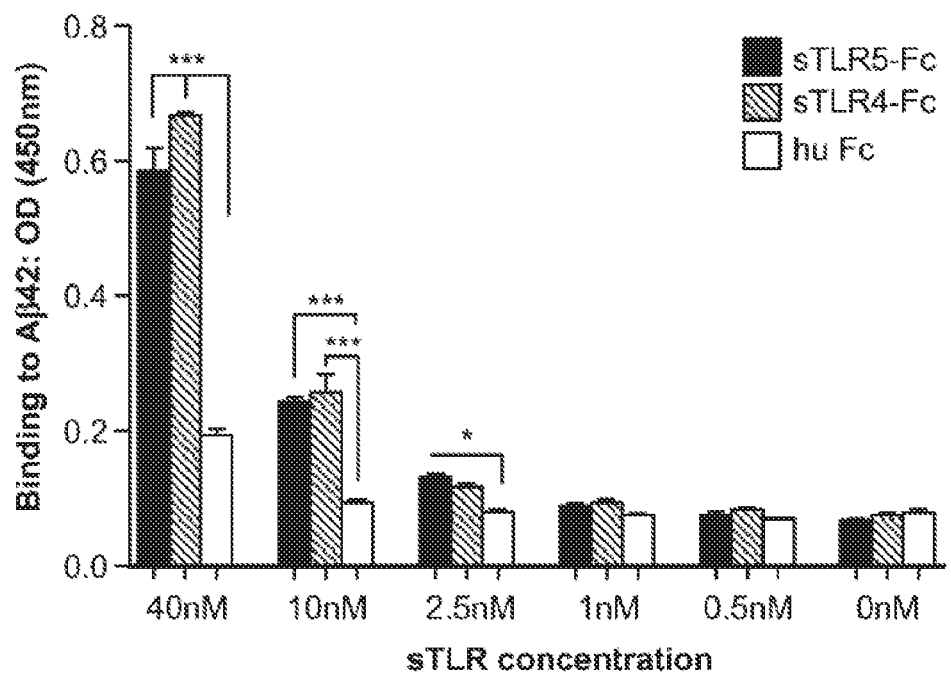
FIG. 28 shows the selectivity of the sTLR5FcV5 effect for aggregated Aβ as compared to monomeric Aβ. Specifically, sTLR5FcV5 and sTLR4FcV5 were observed to bind more efficiently to aggregated Aβ, as compared to monomeric Aβ. (Purified sTLR5FcV5, sTLR4FcV5 and FcV5 proteins were employed in a direct ELISA assay to assess binding to aggregated Aβ or monomeric Aβ. Detection was performed using HRP conjugated anti-Fc antibody. 1-way Anova, *p<0.05, ***p<0.01.)
Figure 28:
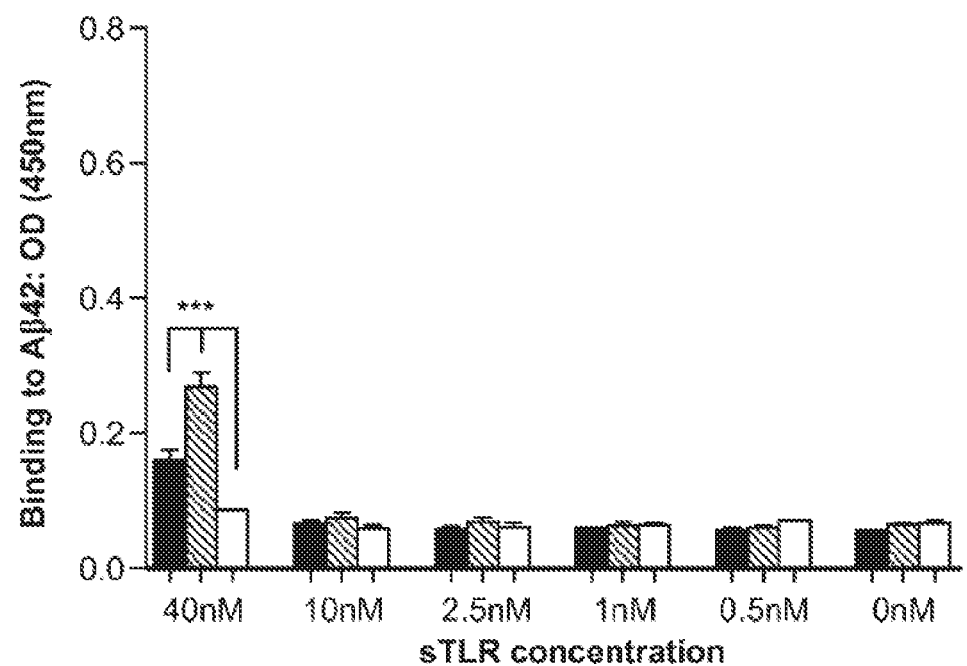

In vitro sTLR5FcV5-Aβ binding experiments also demonstrated a selectivity of effect for aggregated Aβ as compared to monomeric Aβ, which were consistent with the above-observed differential impacts upon Aβ plaques and soluble forms of Aβ. In such experiments, sTLR5FcV5 and sTLR4FcV5 were observed to bind more efficiently to aggregated Aβ, as compared to monomeric Aβ (FIG. 28). Specifically, purified sTLR5FcV5, sTLR4FcV5 and FcV5 proteins were employed in a direct ELISA assay to assess binding to aggregated Aβ or monomeric Aβ. Detection was performed using HRP conjugated anti-Fc antibody. 1-way Anova, *p<0.05, ***p<0.01.

Figure 29:
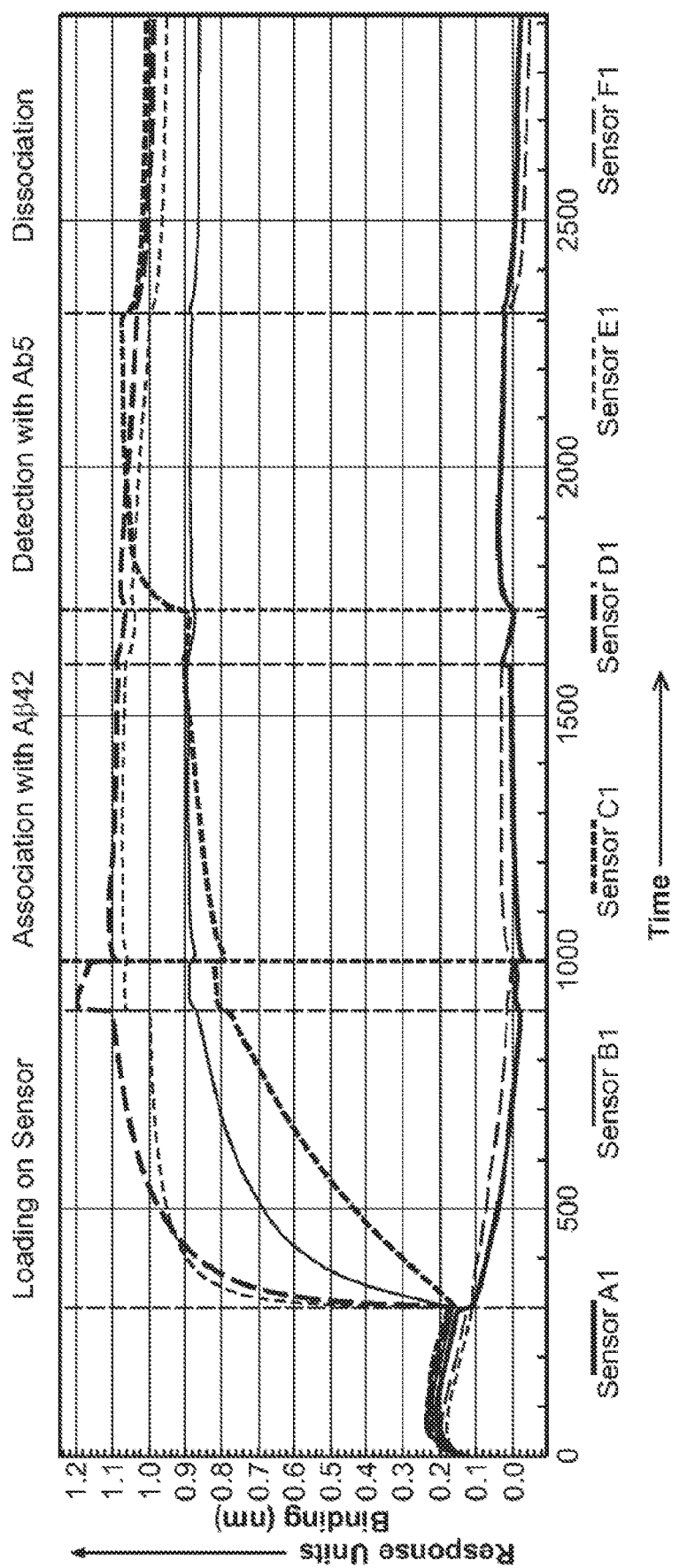
FIG. 29 demonstrates the ability of soluble, CHO cell-expressed sTLR5FcV5 present in CHO cell media to bind to Aβ, as examined using immobilized sTLR5FcV5 from CHO cell media as an immobilized ligand for Aβ.

In a final in vitro experiment, the ability of soluble, CHO cell-expressed sTLR5FcV5 present in CHO cell media to bind to Aβ was examined using immobilized sTLR5FcV5 from CHO cell media as an immobilized ligand for Aβ. As shown in FIG. 29, binding of sTLR5FcV5 to aggregated Aβ42 was observed in real time. Specifically, media from stable CHO cell lines expressing sTLR5FcV5, sTLR4FcV5, FcV5 or commercially available recombinant IgG1 Fc was immobilized on anti-human Fc sensor followed by association of sensor-immobilized ligand to aggregated Aβ42. Presence of bound Aβ42 was detected by anti Aβ1-16 antibody Ab5 only in the sensor incubated with sTLR5FcV5 (see, in particular, the sTLR5FcV5 media trace of the "Detection with Ab5" period of FIG. 29; in FIG. 29, the identities of the traces from lowest to highest at the end of the "Loading on Sensor" period are: (1) lowest=CHO WT media; (2) buffer only; (3) sTLR5FcV5 media; (4) sTLR4FcV5 media; (5) recombinant Fc; and (6) FcV5 media). Thus, sTLR5FcV5 demonstrated specific, real-time binding to Aβ.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference

We claim:

1. A method of modulating Aβ plaque deposition in a subject comprising administering to the subject an effective amount of an AAV vector comprising a nucleic acid molecule encoding a soluble polypeptide comprising a ligand binding site of a Toll-Like Receptor (TLR), wherein the ligand binding site is a ligand binding site of TLR5, and wherein the step of administering causes a reduction in Aβ plaque deposition.

2. The method of claim 1, wherein the AAV vector is a recombinant AAV2, AAV9 or AAV2/1 vector.

3. The method of claim 1, wherein the AAV vector is delivered peripherally or directly to the brain.

4. The method of claim 1, wherein the ligand binding site binds a disease associated molecular pattern (DAMP).

5. The method of claim 4, wherein the DAMP comprises Aβ amyloid.

6. The method of claim 4, wherein the DAMP comprises Aβ40 or Aβ42.

7. The method of claim 1, wherein the nucleic acid molecule encodes a fusion protein comprising a polypeptide that comprises a ligand binding site of a soluble Toll Like Receptor 5 (sTLR5) and an Fc polypeptide.

8. The method of claim 7, wherein the nucleic acid molecule comprises a nucleotide sequence that comprises the sequence of SEQ ID NO: 3 or SEQ ID NO: 6.

9. The method of claim 7, wherein the sTLR5 ligand binding site and the Fc polypeptide are connected by a peptide linker.

10. The method of claim 7, wherein the Fc polypeptide is an IgG1 polypeptide.

11. The method of claim 7, wherein nucleic acid molecule comprises a nucleotide sequence encoding an Fc polypeptide that comprises the sequence of SEQ ID NO: 8 or SEQ ID NO: 9.

12. The method of claim 7, wherein the C-terminus of the sTLR5 ligand binding site polypeptide is connected to the N-terminus of the Fc polypeptide.

13. The method of claim 1, wherein the nucleic acid molecule encodes a polypeptide comprising a fusion protein comprising a ligand binding site of a TLR, an Fc polypeptide, and a tag polypeptide.

14. The method of claim 13, wherein the tag is selected from a TAP, a FLAG, or a V5 polypeptide.

15. The method of claim 14, wherein the nucleic acid molecule comprises a nucleotide sequence encoding a TAP polypeptide that comprises the sequence of SEQ ID NO: 7.

16. The method of claim 14, wherein the polypeptide comprises one or more of the following: sTLR5-TAP, sTLR5-FLAG, sTLR5-Fc-V5, or sTLR5-Fc-FLAG.

* * * * *

SEQUENCE LISTING

```
<160> NUMBER OF SEQ ID NOS: 11

<210> SEQ ID NO 1
<211> LENGTH: 1800
<212> TYPE: DNA
<213> ORGANISM: Artificial Sequence
<220> FEATURE:
<223> OTHER INFORMATION: Synthetic Polynucleotide

<400> SEQUENCE: 1
atgccacata ctttgtggat ggtgtgggtc ttgggggtca tcatcagcct ctccaaggaa        60
gaatcctcca atcaggcttc tctgtcttgt gaccgcaatg gtatctgcaa gggcagctca       120
```

-continued

```
ggatctttaa actccattcc ctcagggctc acagaagctg taaaaagcct tgacctgtcc      180
aacaacagga tcacctacat tagcaacagt gacctacaga ggtgtgtgaa cctccaggct      240
ctggtgctga catccaatgg aattaacaca atagaggaag attcttttc ttccctgggc      300 agtcttgaac atttagactt atcctataat tacttatcta atttatcgtc ttcctggttc      360
aagccccttt cttctttaac attcttaaac ttactgggaa atccttacaa aaccctaggg     420
gaaacatctc tttttctca tctcacaaaa ttgcaaatcc tgagagtggg aaatatggac      480
accttcacta agattcaaag aaaagatttt gctggactta ccttccttga ggaacttgag     540
attgatgctt cagatctaca gagctatgag ccaaaaagtt tgaagtcaat tcagaacgta     600
agtcatctga tccttcatat gaagcagcat attttactgc tggagatttt tgtagatgtt     660
acaagttccg tggaatgttt ggaactgcga gatactgatt tggacacttt ccattttca     720 gaactatcca ctggtgaaac aaattcattg attaaaaagt ttacatttag aaatgtgaaa     780
atcaccgatg aaagtttgtt tcaggttatg aaacttttga atcagatttc tggattgtta     840
gaattagagt ttgatgactg tacccttaat ggagttggta attttagagc atctgataat     900
gacagagtta tagatccagg taaagtggaa acgttaacaa tccggaggct gcatattcca     960
aggttttact tatttatga tctgagcact ttatattcac ttacagaaag agttaaaaga    1020
atcacagtag aaaacagtaa agttttctg gttccttgtt tactttcaca acatttaaaa     1080
tcattagaat acttggatct cagtgaaaat ttgatggttg aagaatactt gaaaaattca    1140
gcctgtgagg atgcctggcc ctctctacaa actttaattt taaggcaaaa tcatttggca    1200
tcattggaaa aaaccggaga gactttgctc actctgaaaa acttgactaa cattgatatc    1260
agtaagaata gttttcattc tatgcctgaa acttgtcagt ggccagaaaa gatgaaatat    1320
ttgaacttat ccagcacacg aatacacagt gtaacaggct gcattcccaa gacactggaa    1380 atttagatg ttagcaacaa caatctcaat ttattttctt tgaatttgcc gcaactcaaa    1440
gaactttata tttccagaaa taagttgatg actctaccag atgcctccct cttacccatg    1500
ttactagtat tgaaaatcag taggaatgca ataactacgt ttttctaagga gcaacttgac    1560 tcatttcaca cactgaagac tttggaagct ggtggcaata acttcatttg ctcctgtgaa    1620
ttcctctcct tcactcagga gcagcaagca ctggccaaag tcttgattga ttggccagca    1680
aattacctgt gtgactctcc atcccatgtg cgtggccagc aggttcagga tgtccgcctc    1740
tcggtgtcgg aatgtcacag gacagcactg gtgtctggca tgtgctgtgc tctgttcctg    1800
```

<210> SEQ ID NO 2
<211> LENGTH: 1892
<212> TYPE: DNA
<213> ORGANISM: Artificial Sequence
<220> FEATURE:
<223> OTHER INFORMATION: Synthetic Polynucleotide

<400> SEQUENCE: 2

```
atgatgtctg cctcgcgcct ggctgggact ctgatcccag ccatggcctt cctctcctgc      60
gtgagaccag aaagctggga gccctgcgtg gaggtggttc ctaatattac ttatcaatgc     120
atggagctga atttctacaa aatccccgac aacctcccct tctcaaccaa gaacctggac     180
ctgagcttta atcccctgag gcatttaggc agctatagct tcttcagttt cccagaactg     240
caggtgctgg atttatccag gtgtgaaatc cagacaattg aagatggggc atatcagagc     300
ctaagccacc tctctacctt aatattgaca ggaaacccca tccagagttt agccctggga     360
gccttttctg gactatcaag tttacagaag ctggtggctg tggagacaaa tctagcatct     420
```

```
ctagagaact tccccattgg acatctcaaa actttgaaag aacttaatgt ggctcacaat      480
cttatccaat ctttcaaatt acctgagtat ttttctaatc tgaccaatct agagcacttg      540
gacctttcca gcaacaagat tcaaagtatt tattgcacag acttgcgggt tctacatcaa      600
atgcccctac tcaatctctc tttagacctg tccctgaacc ctatgaactt tatccaacca      660
ggtgcattta agaaattag gcttcataag ctgactttaa gaataatttt tgatagttta       720
aatgtaatga aaacttgtat tcaaggtctg gctggtttag aagtccatcg tttggttctg      780
ggagaattta gaaatgaagg aaacttggaa aagtttgaca atctgctct agagggcctg       840 tgcaatttga ccattgaaga attccgatta gcatacttag actactacct cgatgatatt      900
attgacttat ttaattgttt gacaaatgtt tcttcatttt ccctggtgag tgtgactatt       960
gaaagggtaa aagactttc ttataatttc ggatggcaac atttagaatt agttaactgt      1020
aaatttggac agtttcccac attgaaactc aaatctctca aaaggcttac tttcacttcc     1080
aacaaaggtg ggaatgcttt ttcagaagtt gatctaccaa gccttgagtt tctagatctc     1140
agtagaaatg gcttgagttt caaaggttgc tgttctcaaa gtgattttgg acaaccagc     1200 ctaaagtatt tagatctgag cttcaatggt gttattacca tgagttcaaa cttcttgggc     1260
ttagaacaac tagaacatct ggatttccag cattccaatt gaaacaaat gagtgagttt     1320 tcagtattcc tatcactcag aaacctcatt taccttgaca tttctcatac tcacaccaga    1380
gttgctttca atggcatctt caatggcttg tccagtctcg aagtcttgaa atggctggc     1440 aattcttttcc aggaaaactt ccttccagat atcttcacag agctgagaaa cttgaccttc   1500
ctggacctct ctcagtgtca actggagcag ttgtctccaa cagcatttaa ctcactctcc     1560
agtcttcagg tactaaatat gagccacaac aacttctttt cattggatac gtttccttat    1620
aagtgtctga actccctcca ggttcttgat tacagctcaa tcacataatg acttccaaaa    1680
aacaggaact acagcatttt ccaagtagtc tagctttctt aaatcttact cagaatgact    1740
ttgcttgtac ttgtgaacac cagagtttcc tgcaatggat caaggaccag aggcagctct   1800
tggtggaagt tgaacgaatg gaatgtgcaa caccttcaga taagcagggc atgcctgtgc   1860
tgagtttgaa tatcacctgt cagatgaata ag                                    1892

<210> SEQ ID NO 3
<211> LENGTH: 1907
<212> TYPE: DNA
<213> ORGANISM: Artificial Sequence
<220> FEATURE:
<223> OTHER INFORMATION: Synthetic Polynucleotide

<400> SEQUENCE: 3
atgggagacc acctggacct tctcctagga gtggtgctca tggccggtcc tgtgtttgga      60
attccttcct gctcctttga tggccgaata gccttttatc gtttctgcaa cctcacccag     120
gtcccccagg tcctcaacac cactgagagg ctcctgctga gcttcaacta tatcaggaca     180
gtcactgctt catccttccc ctttctggaa cagctgcagc tgctggagct cgggagccag     240
tataccccct tgactattga caaggaggcc ttcagaaacc tgcccaacct tagaatcttg     300
gacctgggaa gtagtaagat atacttcttg catccagatg cttttcaggg actgttccat     360
ctgtttgaac ttagactgta tttctgtggt ctctctgatg ctgtattgaa agatggttat     420 ttcagaaaatt taaggctttt aactcgcttg gatctatcca aaaatcagat tcgtagcctt     480
taccttcatc cttcatttgg gaagttgaat tccttaaagt ccatagattt ttcctccaac     540
```

| | |
|---|---|
| caaatattcc ttgtatgtga acatgagctc gagcccctac aagggaaaac gctctccttt | 600 |
| tttagcctcg cagctaatag cttgtatagc agagtctcag tggactgggg aaaatgtatg | 660 |
| aacccattca gaaacatggt gctggagata ctagatgttt ctggaaatgg ctggacagtg | 720 |
| gacatcacag gaaactttag caatgccatc agcaaaagcc aggccttctc tttgattctt | 780 |
| gcccaccaca tcatgggtgc cgggtttggc ttccataaca tcaaagatcc tgaccagaac | 840 |
| acatttgctg gcctggccag aagttcagtg agacacctgg atctttcaca tgggtttgtc | 900 |
| ttctccctga actcacgagt ctttgagaca ctcaaggatt gaaggttct gaaccttgcc | 960 |
| tacaacaaga taataagat tgcagatgaa gcattttacg gacttgacaa cctccaagtt | 1020 |
| ctcaatttgt catataacct tctgggggaa ctttacagtt cgaatttcta tggactacct | 1080 |
| aaggtagcct acattgattt gcaaaagaat cacattgcaa taattcaaga ccaaacattc | 1140 |
| aaattcctgg aaaaattacg gaccttggat ctccgagaca atgctcttac aaccattcat | 1200 |
| tttattccaa gcatacccga tatcttcttg agtggcaata aactagtgac tttgccaaag | 1260 |
| atcaaccta cagcgaacct catccactta tcagaaaaca ggctagaaaa tctagatatt | 1320 |
| ctctactttc tcctacgggt acctcatctc cagattctca ttttaaatca aaatcgcttc | 1380 |
| tcctcctgta gtggagatca aaccccttca gagaatccca gctagaaaca gcttttcctt | 1440 |
| ggagaaaata tgttgcaact tgcctgggaa actgagctct gttgggatgt ttttgaggga | 1500 |
| cttctctcatc ttcaagttct gtatttgaat cataactatc ttaattccct tccaccagga | 1560 |
| gtatttagcc atctgactgc attaagggga ctaagcctca actccaacgg ctgacagttc | 1620 |
| tttctcacaa tgatttacct gctaatttag agatcctgga catatccagg aaccagctcc | 1680 |
| tagctcctaa tcctgatgta tttgtatcac ttagtgtctt ggatataact cataacaagt | 1740 |
| tcatttgtga atgtgaactt agcacttta tcaattggct taatcacacc aatgtcacta | 1800 |
| tagctgggcc tcctgcagac atatattgtg tgtaccctga ctcgttctct ggggtttccc | 1860 |
| tcttctctct ttccacggaa ggttgtgatg aagaggaagt cttaaag | 1907 |

<210> SEQ ID NO 4
<211> LENGTH: 1764
<212> TYPE: DNA
<213> ORGANISM: Artificial Sequence
<220> FEATURE:
<223> OTHER INFORMATION: Synthetic Polynucleotide

<400> SEQUENCE: 4

| | |
|---|---|
| atgccacata cttttgtggat ggtgtgggtc ttgggggtca tcatcagcct ctccaaggaa | 60 |
| gaatcctcca atcaggcttc tctgtcttgt gaccgcaatg gtatctgcaa gggcagctca | 120 |
| ggatctttaa actccattcc ctcagggctc acagaagctg taaaaagcct tgacctgtcc | 180 |
| aacaacagga tcacctacat tagcaacagt gacctacaga ggtgtgtgaa cctccaggct | 240 |
| ctggtgctga catccaatgg aattaacaca atagaggaag attctttttc ttccctgggc | 300 |
| agtcttgaac atttagactt atcctataat tacttatcta atttatcgtc ttcctggttc | 360 |
| aagcccctt cttctttaac attcttaaac ttactgggaa atccttacaa aaccctaggg | 420 |
| gaaacatctc ttttttctca tctcacaaaa ttgcaaatcc tgagagtggg aaatatggac | 480 |
| accttcacta agattcaaag aaaagatttt gctggactta ccttccttga ggaacttgag | 540 |
| attgatgctt cagatctaca gagctatgag ccaaaaagtt tgaagtcaat tcagaacgta | 600 |
| agtcatctga tccttcatat gaagcagcat attttactgc tggagatttt tgtagatgtt | 660 |
| acaagttccg tggaatgttt ggaactgcga gatactgatt tggacacttt ccattttca | 720 |

-continued

```
gaactatcca ctggtgaaac aaattcattg attaaaaagt ttacatttag aaatgtgaaa      780
atcaccgatg aaagtttgtt tcaggttatg aaacttttga atcagatttc tggattgtta      840
gaattagagt ttgatgactg taccctttaat ggagttggta attttagagc atctgataat     900
gacagagtta tagatccagg taaagtggaa acgttaacaa tccggaggct gcatattcca      960
aggttttact tattttatga tctgagcact ttatattcac ttacagaaag agttaaaaga    1020
atcacagtag aaaacagtaa agttttctg gttccttgtt tactttcaca acatttaaaa     1080
tcattagaat acttggatct cagtgaaaat ttgatggttg aagaatactt gaaaaattca    1140
gcctgtgagg atgcctggcc ctctctacaa actttaattt taaggcaaaa tcatttggca     1200
tcattggaaa aaccggaga actttgctc actctgaaaa acttgactaa cattgatatc      1260
agtaagaata gttttcattc tatgcctgaa acttgtcagt ggccagaaaa gatgaaatat    1320
ttgaacttat ccagcacacg aatacacagt gtaacaggct gcattcccaa gacactggaa    1380 atttttagatg ttagcaacaa caatctcaat ttatttttctt tgaatttgcc gcaactcaaa   1440
gaactttata tttccagaaa taagttgatg actctaccag atgcctccct cttacccatg    1500
ttactagtat tgaaaatcag taggaatgca ataactacgt tttctaagga gcaacttgac    1560
tcatttcaca cactgaagac tttggaagct ggtggcaata acttcatttg ctcctgtgaa    1620
ttcctctcct tcactcagga gcagcaagca ctggccaaag tcttgattga ttggccagca    1680
aattacctgt gtgactctcc atcccatgtg cgtggccagc aggttcagga tgtccgcctc    1740
tcggtgtcgg aatgtcacag gaca                                          1764
```

<210> SEQ ID NO 5
<211> LENGTH: 1773
<212> TYPE: DNA
<213> ORGANISM: Artificial Sequence
<220> FEATURE:
<223> OTHER INFORMATION: Synthetic Polynucleotide

<400> SEQUENCE: 5

```
atggagctga atttctacaa atccccgac aacctcccct ctcaaccaa gaacctggac        60 ctgagcttta atccctgag gcatttaggc agctatagct tcttcagttt cccagaactg      120
caggtgctgg atttatccag gtgtgaaatc cagacaattg aagatggggc atatcagagc     180
ctaagccacc tctctaccct aatattgaca ggaaaccca tccagagttt agccctggga      240 gcctttctg gactatcaag tttacagaag ctggtggctg tggagacaaa tctagcatct      300
ctagagaact tccccattgg acatctcaaa actttgaaag aacttaatgt ggctcacaat      360
cttatccaat ctttcaaatt acctgagtat ttttctaatc tgaccaatct agagcacttg     420 gaccttttcca gcaacaagat tcaaagtatt tattgcacag acttgcgggt ctacatcaa     480 atgcccctac tcaatctctc tttagacctg tccctgaacc ctatgaactt tatccaacca     540
ggtgcattta agaaattag gcttcataag ctgactttaa gaaataattt tgatagttta     600
aatgtaatga aaacttgtat tcaaggtctg gctggtttag aagtccatcg tttggttctg     660
ggagaattta gaaatgaagg aaacttggaa aagtttgaca aatctgctct agagggcctg     720
tgcaatttga ccattgaaga attccgatta gcatacttag actactacct cgatgatatt     780
attgacttat ttaattgttt gacaaatgtt tcttcatttt ccctggtgag tgtgactatt     840
gaaagggtaa aagacttttc ttataatttc ggatggcaac atttagaatt agttaactgt     900
aaatttggac agtttcccac attgaaactc aaatctctca aaaggcttac tttcacttcc     960
```

-continued

| | | | |
|---|---|---|---|
| aacaaaggtg | ggaatgcttt | ttcagaagtt gatctaccaa gccttgagtt tctagatctc | 1020 |
| agtagaaatg | gcttgagttt | caaaggttgc tgttctcaaa gtgattttgg gacaaccagc | 1080 |
| ctaaagtatt | tagatctgag | cttcaatggt gttattacca tgagttcaaa cttcttgggc | 1140 |
| ttagaacaac | tagaacatct | ggatttccag cattccaatt tgaaacaaat gagtgagttt | 1200 |
| tcagtattcc | tatcactcag | aaacctcatt taccttgaca tttctcatac tcacaccaga | 1260 |
| gttgctttca | atggcatctt | caatggcttg tccagtctcg aagtcttgaa atggctggc | 1320 |
| aattcttttcc | aggaaaactt | ccttccagat atcttcacag agctgagaaa cttgaccttc | 1380 |
| ctggacctct | ctcagtgtca | actggagcag ttgtctccaa cagcatttaa ctcactctcc | 1440 |
| agtcttcagg | tactaaatat | gagccacaac aacttctttt cattggatac gtttccttat | 1500 |
| aagtgtctga | actccctcca | ggttcttgat tacagtctca atcacataat gacttccaaa | 1560 |
| aaacaggaac | tacagcattt | tccaagtagt ctagctttct taaatcttac tcagaatgac | 1620 |
| tttgcttgta | cttgtgaaca | ccagagtttc ctgcaatgga tcaaggacca gaggcagctc | 1680 |
| ttggtggaag | ttgaacgaat | ggaatgtgca acaccttcag ataagcaggg catgcctgtg | 1740 |
| ctgagtttga | atatcacctg | tcagatgaat aag | 1773 |

<210> SEQ ID NO 6
<211> LENGTH: 1917
<212> TYPE: DNA
<213> ORGANISM: Artificial Sequence
<220> FEATURE:
<223> OTHER INFORMATION: Synthetic Polynucleotide

<400> SEQUENCE: 6

| | | | |
|---|---|---|---|
| atgggagacc | acctggacct | tctcctagga gtggtgctca tggccggtcc tgtgtttgga | 60 |
| attccttcct | gctccttga | tggccgaata gccttttatc gtttctgcaa cctcacccag | 120 |
| gtcccccagg | tcctcaacac | cactgagagg ctcctgctga gcttcaacta tatcaggaca | 180 |
| gtcactgctt | catccttccc | cttctggaa cagctgcagc tgctggagct cgggagccag | 240 |
| tataccccct | tgactattga | caaggaggcc ttcagaaacc tgcccaacct tagaatcttg | 300 |
| gacctgggaa | gtagtaagat | atacttcttg catccagatg cttttcaggg actgttccat | 360 |
| ctgtttgaac | ttagactgta | tttctgtggt ctctctgatg ctgtattgaa agatggttat | 420 |
| ttcagaaatt | taaaggcttt | aactcgcttg gatctatcca aaaatcagat tcgtagcctt | 480 |
| taccttcatc | cttcatttgg | gaagttgaat tccttaaagt ccatagattt ttcctccaac | 540 |
| caaatattcc | ttgtatgtga | acatgagctc gagcccctac aagggaaaac gctctccttt | 600 |
| tttagcctcg | cagctaatag | cttgtatagc agagtctcag tggactgggg aaaatgtatg | 660 |
| aacccattca | gaaacatggt | gctggagata ctagatgttt ctggaaatgg ctggacagtg | 720 |
| gacatcacag | gaaactttag | caatgccatc agcaaaagcc aggccttctc tttgattctt | 780 |
| gcccaccaca | tcatgggtgc | cgggtttggc ttccataaca tcaaagatcc tgaccagaac | 840 |
| acatttgctg | gcctggccag | aagttcagtg agacacctgg atctttcaca tgggtttgtc | 900 |
| ttctccctga | actcacgagt | ctttgagaca ctcaaggatt tgaaggttct gaaccttgcc | 960 |
| tacaacaaga | taaataagat | tgcagatgaa gcattttacg gacttgacaa cctccaagtt | 1020 |
| ctcaatttgt | catataacct | tctgggggaa ctttacagtt cgaatttcta tggactacct | 1080 |
| aaggtagcct | acattgattt | gcaaaagaat cacattgcaa taattcaaga ccaaacattc | 1140 |
| aaattcctgg | aaaaattacg | gaccttggat ctccgagaca atgctcttac aaccattcat | 1200 |
| tttattccaa | gcatacccga | tatcttcttg agtggcaata aactagtgac tttgccaaag | 1260 |

```
atcaaccta cagcgaacct catccactta tcagaaaaca ggctagaaaa tctagatatt    1320
ctctactttc tcctacgggt acctcatctc cagattctca ttttaaatca aaatcgcttc    1380
tcctcctgta gtggagatca aaccccttca gagaatccca gcttagaaca gcttttcctt    1440
ggagaaaata tgttgcaact tgcctgggaa actgagctct gttgggatgt ttttgaggga    1500 cttctcatc ttcaagttct gtatttgaat cataactatc ttaattccct tccaccagga    1560
gtatttagcc atctgactgc attaagggga ctaagcctca actccaacag ctgacagtt    1620 ctttctcaca tgatttacc tgctaattta gagatcctgg acatatccag gaaccagctc    1680
ctagctccta atcctgatgt atttgtatca cttagtgtct tggatataac tcataacaag    1740
ttcatttgtg aatgtgaact tagcactttt atcaattggc ttaatcacac caatgtcact    1800
atagctgggc ctcctgcaga catatattgt gtgtaccctg actcgttctc tggggtttcc    1860
ctcttctctc tttccacgga aggttgtgat gaagaggaag tcttaaagtc cctaaag      1917

<210> SEQ ID NO 7
<211> LENGTH: 168
<212> TYPE: DNA
<213> ORGANISM: Artificial Sequence
<220> FEATURE:
<223> OTHER INFORMATION: Synthetic Polynucleotide

<400> SEQUENCE: 7
gattataaag atgatgatga taaagggtcg gccgccagct ggagccaccc tcagttcgag     60
aagggaggag gaagcggcgg aggcagcgga ggaggaagct ggagccaccc gcagttcgag    120
aaacatcatc accatcacca taccggtcat catcaccatc accattga                 168

<210> SEQ ID NO 8
<211> LENGTH: 726
<212> TYPE: DNA
<213> ORGANISM: Artificial Sequence
<220> FEATURE:
<223> OTHER INFORMATION: Synthetic Polynucleotide

<400> SEQUENCE: 8
gtgcccaggg attgtggttg taagccttgc atatgtacag tcccagaagt atcatctgtc     60
ttcatcttcc ccccaaagcc caaggatgtg ctcaccatta ctctgactcc taaggtcacg    120
tgtgttgtgg tagacatcag caaggatgat cccgaggtcc agttcagctg gtttgtagat    180
gatgtggagg tgcacacagc tcagacgcaa ccccgggagg agcagttcaa cagcactttc    240
cgctcagtca gtgaacttcc catcatgcac caggactggc tcaatggcaa ggagttcaaa    300
tgcagggtma acagtgcagc tttccctgcc cccatcgaga aaaccatctc caaaaccaaa    360
ggcagaccga aggctccaca ggtgtacacc attccacctc caaggagca gatggccaag    420 gataaagtca gtctgacctg catgataaca gacttcttcc ctgaagacat tactgtggag    480
tggcagtgga atgggcagcc agcggagaac tacaagaaca ctcagcccat catggacaca    540
gatggctctt acttcgtcta cagcaagctc aatgtgcaga gagcaactg ggaggcagga    600 aatactttca cctgctctgt gttacatgag ggcctgcaca accaccatac tgagaagagc    660
ctctaccacc tggtaaatag cggtaagcct atccctaacc ctctcctcgg tctcgattct    720
acgtaa                                                                726

<210> SEQ ID NO 9
<211> LENGTH: 732
<212> TYPE: DNA
```

<213> ORGANISM: Artificial Sequence
<220> FEATURE:
<223> OTHER INFORMATION: Synthetic Polynucleotide

<400> SEQUENCE: 9

| | | | | | |
|---|---|---|---|---|---|
| gagtccaaat | atggtccccc | atgcccatca | tgcccagcac | ctgagttcct | gggggggacca | 60 |
| tcagtcttcc | tgttcccccc | aaacccaag | gacactctca | tgatctcccg | gaccccctgag | 120 |
| gtcacgtgcg | tggtggtgga | cgtgagccag | aagaccccg | aggtccagtt | caactggtac | 180 |
| gtggatggcg | tggaggtgca | taatgccaag | acaaagccgc | gggaggagca | gttcaacagc | 240 |
| acgtaccgtg | tggtcagcgt | cctcaccgtc | ctgcaccagg | actggctgaa | cggcaaggag | 300 |
| tacaagtgca | aggtctccaa | caaaggcctc | ccgtcctcca | tcgagaaaac | catctccaaa | 360 |
| gccaaagggc | agccccgaga | gccacaggtg | tacaccctgc | ccccatccca | ggaggagatg | 420 |
| accaagaacc | aggtcagcct | gacctgcctg | gtcaaaggct | tctaccccag | cgacatcgcc | 480 |
| gtggagtggg | agagcaatgg | gcagccggag | aacaactaca | agaccacgcc | tcccgtgctg | 540 |
| gactccgacg | gctccttctt | cctctacagc | aggctaaccg | tggacaagag | caggtggcag | 600 |
| gagggggaatg | tcttctcatg | ctccgtgatg | catgaggctc | tgcacaacca | ctacacacag | 660 |
| aagagcctct | ccctgtctct | gggtaaactc | gagggaggag | gaagcgatta | taaagatgat | 720 |
| gatgataaat | aa | | | | | 732 |

<210> SEQ ID NO 10
<211> LENGTH: 6078
<212> TYPE: DNA
<213> ORGANISM: Artificial Sequence
<220> FEATURE:
<223> OTHER INFORMATION: Synthetic Polynucleotide

<400> SEQUENCE: 10

| | | | | | |
|---|---|---|---|---|---|
| gacggatcgg | gagatcgatc | ccgttgacat | tgattattga | ctagttatta | atagtaatca | 60 |
| attacggggt | cattagttca | tagcccatat | atggagttcc | gcgttacata | acttacggta | 120 |
| aatggcccgc | ctggctgacc | gcccaacgac | ccccgcccat | tgacgtcaat | aatgacgtat | 180 |
| gttcccatag | taacgccaat | agggactttc | cattgacgtc | aatgggtgga | ctatttacgg | 240 |
| taaactgccc | acttggcagt | acatcaagtg | tatcatatgc | caagtacgcc | ccctattgac | 300 |
| gtcaatgacg | gtaaatggcc | cgcctggcat | tatgcccagt | acatgacctt | atgggacttt | 360 |
| cctacttggc | agtacatcta | cgtatcgagg | tgagccccac | gttctgcttc | actctcccca | 420 |
| tctcccccc | ctccccaccc | ccaattttgt | atttatttat | tttttaatta | ttttgtgcag | 480 |
| cgatggggggc | gggggggggg | ggggcgcgcg | ccaggcgggg | cggggcgggg | cgaggggcgg | 540 |
| ggcggggcga | ggcggagagg | tgcggcggca | gccaatcaga | gcggcgcgct | ccgaaagttt | 600 |
| ccttttatgg | cgaggcggcg | gcggcggcgg | ccctataaaa | agcgaagcgc | gcggcgggcg | 660 |
| ggagtcgctg | cgttgccttc | gccccgtgcc | ccgctccgcg | ccgcctcgcg | ccgcccgccc | 720 |
| cggctctgac | tgaccgcgtt | actcccacag | gtgagcgggc | gggacggccc | ttctcctccg | 780 |
| ggctgtaatt | agcgcttggt | ttaatgacgg | ctcgtttctt | ttctgtggct | gcgtgaaagc | 840 |
| cttaaagggc | tccggagggg | cccttttgtgc | ggggggggagc | ggctcggggg | gtgcgtgcgt | 900 |
| gtgtgtgtgc | gtggggagcg | ccgcgtgcgg | cccgcgctgc | ccggcggctg | tgagcgctgc | 960 |
| gggcgcggcg | cggggctttg | tgcgctccgc | gtgtgcgcga | ggggagcgcg | gccgggggcg | 1020 |
| gtgccccgcg | gtgcggggg | gctgcgaggg | gaacaaaggc | tgcgtgcggg | gtgtgtgcgt | 1080 |
| gggggggtga | gcaggggggtg | tgggcgcggc | ggtcgggctg | taaccccccc | ctgcaccccc | 1140 |

```
ctccccgagt tgctgagcac ggcccggctt cgggtgcggg gctccgtgcg gggcgtggcg    1200
cggggctcgc cgtgccgggc ggggggtggc ggcaggtggg ggtgccggac ggggcggggc    1260
cgcctcgggc cggggagggc tcggggagg ggcgcggcgg ccccggagcg ccggcggctg    1320
tcgaggcgcg gcgagccgca gccattgcct tttatggtaa tcgtgcgaga gggcgcaggg    1380
acttcctttg tcccaaatct ggcggagccg aaatctggga ggcgccgccg cacccctct    1440 agcgggcgcg ggcgaagcgg tgcggcgccg gcaggaagga aatgggcggg gagggccttc    1500
gtgcgtcgcc gcgccgccgt ccccttctcc atctccagcc tcggggctgc cgcagggggga    1560 cggctgcctt cggggggggac ggggcagggc ggggttcggc ttctggcgtg tgaccggcgg    1620
gtctagacct ctgctaacca tgttcatgcc ttcttctctt tcctacagct cctgggcaac    1680
gtgctggttg ttgtgctgtc tcatcatttt ggcaaagaag cttggtaccg agctcggatc    1740
cactagtcca gtgtggtgga attctgcaga tatccagcac agtggcggcc gctcgagtct    1800
agagggccct attctatagt gtcacctaaa tgctagagct cgctgatcag cctcgactgt    1860
gccttctagt tgccagccat ctgttgtttg cccctccccc gtgccttcct tgaccctgga    1920
aggtgccact cccactgtcc tttcctaata aaatgaggaa attgcatcgc attgtctgag    1980
taggtgtcat tctattctgg ggggtggggt ggggcaggac agcaagggg aggattggga    2040 agacaatagc aggcatgctg gggatgttta aacccgctga tcagcctcga ctgtgccttc    2100
tagttgccag ccatctgttg tttgcccctc ccccgtgcct tccttgaccc tggaaggtgc    2160
cactcccact gtccttttcct aataaaatga ggaaattgca tcgcattgtc tgagtaggtg    2220
tcattctatt ctgggggtg gggtggggca ggacagcaag gggaggatt gggaagacaa    2280 tagcaggcat gctggggatg cggtgggctc tatggcttct gaggcggaaa gaaccagctg    2340
gggctctagg gggtatcccc acgcgccctg tagcggcgca ttaagcgcgg cgggtgtggt    2400
ggttacgcgc agcgtgaccg ctacacttgc cagcgcccta gcgcccgctc ctttcgcttt    2460
cttcccttcc tttctcgcca cgttcgccgg ctttccccgt caagctctaa atcggggcat    2520
ccctttaggg ttccgattta gtgctttacg gcacctcgac cccaaaaaac ttgattaggg    2580
tgatggttca cgtagtgggc catcgccctg atagacggtt tttcgccctt tgacgttgga    2640
gtccacgttc tttaatagtg gactcttgtt ccaaactgga acaacactca accctatctc    2700
ggtctattct tttgatttat aagggatttt ggggatttcg gcctattggt taaaaaatga    2760
gctgatttaa caaaaattta acgcgaatta attctgtgga atgtgtgtca gttagggtgt    2820
ggaaagtccc caggctcccc aggcaggcag aagtatgcaa agcatgcatc tcaattagtc    2880
agcaaccagg tgtggaaagt ccccaggctc cccagcaggc agaagtatgc aaagcatgca    2940
tctcaattag tcagcaacca tagtcccgcc cctaactccg cccatcccgc cctaactcc    3000 gcccagttcc gcccattctc cgccccatgg ctgactaatt tttttatttt atgcagaggc    3060
cgaggccgcc tctgcctctg agctattcca aagtagtga ggaggctttt ttggaggcct    3120
aggcttttgc aaaaagctcc cgggagcttg tatatccatt ttcggatctg atcagcacgt    3180
gttgacaatt aatcatcggc atagtatatc ggcatagtat aatacgacaa ggtgaggaac    3240
taaaccatgg ccaagttgac cagtgccgtt ccggtgctca ccgcgcgcga cgtcgccgga    3300
gcggtcgagt tctggaccga ccggctcggg ttctcccggg acttcgtgga ggacgacttc    3360
gccggtgtgg tccgggacga cgtgaccctg ttcatcagcg cggtccagga ccaggtggtg    3420
ccggacaaca ccctggcctg ggtgtgggtg cgcggcctgg acgagctgta cgccgagtgg    3480
```

```
tcggaggtcg tgtccacgaa cttccgggac gcctccgggc cggccatgac cgagatcggc   3540
gagcagccgt gggggcggga gttcgccctg cgcgacccgg ccggcaactg cgtgcacttc   3600
gtggccgagg agcaggactg acacgtgcta cgagatttcg attccaccgc cgccttctat   3660
gaaaggttgg gcttcggaat cgttttccgg gacgccggct ggatgatcct ccagcgcggg   3720
gatctcatgc tggagttctt cgcccacccc aacttgttta ttgcagctta taatggttac   3780
aaataaagca atagcatcac aaatttcaca aataaagcat ttttttcact gcattctagt   3840
tgtggtttgt ccaaactcat caatgtatct tatcatgtct gtataccgtc gacctctagc   3900
tagagcttgg cgtaatcatg gtcatagctg tttcctgtgt gaaattgtta tccgctcaca   3960
attccacaca acatacgagc cggaagcata aagtgtaaag cctggggtgc ctaatgagtg   4020
agctaactca cattaattgc gttgcgctca ctgcccgctt tccagtcggg aaacctgtcg   4080
tgccagctgc attaatgaat cggccaacgc gcggggagag gcggtttgcg tattgggcgc   4140
tcttccgctt cctcgctcac tgactcgctg cgctcggtcg ttcggctgcg gcgagcggta   4200
tcagctcact caaaggcggt aatacggtta tccacagaat caggggataa cgcaggaaag   4260
aacatgtgag caaaaggcca gcaaaaggcc aggaaccgta aaaaggccgc gttgctggcg   4320
tttttccata ggctccgccc ccctgacgag catcacaaaa atcgacgctc aagtcagagg   4380
tggcgaaacc cgacaggact ataaagatac caggcgtttc ccctggaag ctccctcgtg   4440 cgctctcctg ttccgaccct gccgcttacc ggatacctgt ccgcctttct cccttcggga   4500
agcgtggcgc tttctcaatg ctcacgctgt aggtatctca gttcggtgta ggtcgttcgc   4560
tccaagctgg gctgtgtgca cgaaccccc gttcagcccg accgctgcgc cttatccggt   4620
aactatcgtc ttgagtccaa cccggtaaga cacgacttat cgccactggc agcagccact   4680
ggtaacagga ttagcagagc gaggtatgta ggcggtgcta cagagttctt gaagtggtgg   4740
cctaactacg gctacactag aaggacagta tttggtatct gcgctctgct gaagccagtt   4800
accttcggaa aaagagttgg tagctcttga tccggcaaac aaaccaccgc tggtagcggt   4860
ggtttttttg tttgcaagca gcagattacg cgcagaaaaa aaggatctca agaagatcct   4920
ttgatctttt ctacggggtc tgacgctcag tggaacgaaa actcacgtta agggattttg   4980
gtcatgagat tatcaaaaag gatcttcacc tagatccttt taaattaaaa atgaagtttt   5040
aaatcaatct aaagtatata tgagtaaact tggtctgaca gttaccaatg cttaatcagt   5100
gaggcaccta tctcagcgat ctgtctattt cgttcatcca tagttgcctg actccccgtc   5160
gtgtagataa ctacgatacg ggagggctta ccatctggcc ccagtgctgc aatgataccg   5220
cgagacccac gctcaccggc tccagattta tcagcaataa accagccagc cggaagggcc   5280
gagcgcagaa gtggtcctgc aactttatcc gcctccatcc agtctattaa ttgttgccgg   5340
gaagctagag taagtagttc gccagttaat agtttgcgca acgttgttgc cattgctaca   5400
ggcatcgtgg tgtcacgctc gtcgtttggt atggcttcat tcagctccgg ttcccaacga   5460
tcaaggcgag ttacatgatc ccccatgttg tgcaaaaaag cggttagctc cttcggtcct   5520
ccgatcgttg tcagaagtaa gttggccgca gtgttatcac tcatggttat ggcagcactg   5580
cataattctc ttactgtcat gccatccgta agatgctttt ctgtgactgg tgagtactca   5640
accaagtcat tctgagaata gtgtatgcgg cgaccgagtt gctcttgccc ggcgtcaata   5700
cgggataata ccgcgccaca tagcagaact ttaaaagtgc tcatcattgg aaaacgttct   5760
tcggggcgaa aactctcaag gatcttaccg ctgttgagat ccagttcgat gtaacccact   5820
cgtgcaccca actgatcttc agcatctttt actttcacca gcgtttctgg gtgagcaaaa   5880
```

```
acaggaaggc aaaatgccgc aaaaaaggga ataagggcga cacggaaatg ttgaatactc      5940
atactcttcc tttttcaata ttattgaagc atttatcagg gttattgtct catgagcgga      6000
tacatatttg aatgtattta gaaaaataaa caaataggggg ttccgcgcac atttccccga     6060
aaagtgccac ctgacgtc                                                    6078

<210> SEQ ID NO 11
<211> LENGTH: 5393
<212> TYPE: DNA
<213> ORGANISM: Artificial Sequence
<220> FEATURE:
<223> OTHER INFORMATION: Synthetic Polynucleotide

<400> SEQUENCE: 11
gggggggggg ggggggggtt ggccactccc tctctgcgcg ctcgctcgct cactgaggcc        60
gggcgaccaa aggtcgcccg acgcccgggc tttgcccggg cggcctcagt gagcgagcga       120
gcgcgcagag agggagtggc caactccatc actaggggtt cctagatctg aattcggtac       180
cctagttatt aatagtaatc aattacgggg tcattagttc atagcccata tatggagttc      240
cgcgttacat aacttacggt aaatggcccg cctggctgac cgcccaacga ccccccgccca     300 ttgacgtcaa taatgacgta tgttcccata gtaacgccaa tagggacttt ccattgacgt      360
caatgggtgg actatttacg gtaaactgcc cacttggcag tacatcaagt gtatcatatg      420
ccaagtacgc cccctattga cgtcaatgac ggtaaatggc ccgcctggca ttatgcccag      480
tacatgacct tatgggactt tcctacttgg cagtacatct acgtattagt catcgctatt      540
accatggtcg aggtgagccc cacgttctgc ttcactctcc ccatctcccc ccctcccca      600 cccccaattt tgtatttatt tatttttaa ttattttgtg cagcgatggg ggcggggggg       660
gggggggggc gcgcgccagg cggggcgggg cgggcgaggg ggcggggcgg ggcgaggcgg      720
agaggtgcgg cggcagccaa tcagagcggc gcgctccgaa agtttccttt tatggcgagg      780
cggcggcggc ggcggcccta taaaaagcga agcgcgcggc gggcgggagt cgctgcgacg      840
ctgccttcgc cccgtgcccc gctccgccgc cgcctcgcgc cgcccgcccc ggctctgact      900
gaccgcgtta ctcccacagg tgagcgggcg gacggcccct tctcctccgg gctgtaatta      960
gcgcttggtt taatgacggc ttgtttcttt tctgtggctg cgtgaaagcc ttgaggggct     1020 ccggagggc cctttgtgcg ggggggagcg ggctcgggggg tgcgtgcgtg tgtgtgtgcg    1080
tggggagcgc cgcgtgcggc ccgcgctgcc cggcggctgt gagcgctgcg ggcgcggcgc    1140
ggggctttgt gcgctccgca gtgtgcgcga ggggagcgcg gccgggggcg gtgccccgcg    1200
gtgcgggggg ggctgcgagg ggaacaaagg ctgcgtgcgg ggtgtgtgcg tgggggggtg     1260 agcaggggt gtgggcgcgg cggtcgggct gtaaccccccc cctgcacccc cctccccgag    1320
ttgctgagca cggcccggct tcgggtgcgg ggctccgtac ggggcgtggc gcggggctcg    1380
ccgtgccggg cggggggtgg cggcaggtgg gggtgccggg cggggcgggg ccgcctcggg    1440
ccggggaggg ctcgggggag gggcgcggcg gcccccggag cgccggcggc tgtcgaggcg    1500
cggcgagccg cagccattgc cttttatggt aatcgtgcga gagggcgcag ggacttcctt    1560
tgtcccaaat ctgtgcggag ccgaaatctg ggaggcgccg ccgcaccccc tctagcgggc    1620
gcggggcgaa gcggtgcggc gccggcagga aggaaatggg cggggagggc cttcgtgcgt    1680
cgccgcgccg ccgtcccctt ctccctctcc agcctcgggg ctgtccgcgg gggacggct    1740 gccttcgggg gggacgggc agggcggggt tcggcttctg gcgtgtgacc ggcggctcta    1800
```

```
gagcctctgc taaccatgtt catgccttct tcttttcct acagctcctg ggcaacgtgc    1860
tggttattgt gctgtctcat cattttggca agaattcct cgaagatcta ggcctgcagg    1920
cggccgcact agtaagcttg atatcctcga ggctagcgga tccgattata agatgatga    1980 tgataaaggg tcggccgcca gctggagcca ccctcagttc gagaagggag gaggaagcgg    2040
cggaggcagc ggaggaggaa gctggagcca cccgcagttc gagaaacatc atcaccatca    2100
ccataccggt catcatcacc atcaccattg agtttaaacc cgctgatcag cgtcgactag    2160
agctcgctga tcagcctcga ctgtgccttc tagttgccag ccatctgttg tttgccctc     2220 ccccgtgcct tccttgaccc tggaaggtgc cactcccact gtcctttcct aataaaatga    2280
ggaaattgca tcgcattgtc tgagtaggtg tcattctatt ctggggggtg gggtggggca    2340
ggacagcaag ggggaggatt gggaagacaa tagcaggcat gctggggaga gatctaggaa    2400
cccctagtga tggagttggc cactccctct ctgcgcgctc gctcgctcac tgaggccgcc    2460
cgggcaaagc ccgggcgtcg ggcgaccttt ggtcgcccgg cctcagtgag cgagcgagcg    2520
cgcagagagg gagtggccaa ccccccccc cccccctg cagccctgca ttaatgaatc       2580
ggccaacgcg cggggagagg cggtttgcgt attgggcgct cttccgcttc ctcgctcact    2640
gactcgctgc gctcggtcgt tcggctgcgg cgagcggtat cagctcactc aaaggcggta    2700
atacggttat ccacagaatc aggggataac gcaggaaaga acatgtgagc aaaaggccag    2760
caaaaggcca ggaaccgtaa aaaggccgcg ttgctggcgt ttttccatag gctccgcccc    2820
cctgacgagc atcacaaaaa tcgacgctca agtcagaggt ggcgaaaccc gacaggacta    2880
taaagatacc aggcgtttcc ccctggaagc tccctcgtgc gctctcctgt tccgaccctg    2940
ccgcttaccg gatacctgtc cgcctttctc ccttcgggaa gcgtggcgct ttctcaatgc    3000
tcacgctgta ggtatctcag ttcggtgtag tcgttcgct ccaagctggg ctgtgtgcac     3060
gaaccccccg ttcagcccga ccgctgcgcc ttatccggta actatcgtct tgagtccaac    3120
ccggtaagac acgacttatc gccactggca gcagccactg gtaacaggat tagcagagcg    3180
aggtatgtag gcggtgctac agagttcttg aagtggtggc ctaactacgg ctacactaga    3240
aggacagtat ttggtatctg cgctctgctg aagccagtta ccttcggaaa aagagttggt    3300
agctcttgat ccggcaaaca aaccaccgct ggtagcggtg ttttttttgt ttgcaagcag    3360
cagattacgc gcagaaaaaa aggatctcaa gaagatcctt tgatctttc tacgggtct      3420 gacgctcagt ggaacgaaaa ctcacgttaa gggattttgg tcatgagatt atcaaaaagg    3480
atcttcacct agatcctttt aaattaaaaa tgaagtttta aatcaatcta agtatatat     3540 gagtaaactt ggtctgacag ttaccaatgc ttaatcagtg aggcacctat ctcagcgatc    3600
tgtctatttc gttcatccat agttgcctga ctccccgtcg tgtagataac tacgatacgg    3660
gagggcttac catctggccc cagtgctgca atgataccgc gagacccacg ctcaccggct    3720
ccagatttat cagcaataaa ccagccagcc ggaagggccg agcgcagaag tggtcctgca    3780
actttatccg cctccatcca gtctattaat tgttgccggg aagctagagt aagtagttcg    3840
ccagttaata gtttgcgcaa cgttgttgcc attgctacag gcatcgtggt gtcacgctcg    3900
tcgtttggta tggcttcatt cagctccggt tcccaacgat caaggcgagt tacatgatcc    3960
cccatgttgt gcaaaaaagc ggttagctcc ttcggtcctc cgatcgttgt cagaagtaag    4020
ttggccgcag tgttatcact catggttatg gcagcactgc ataattctct tactgtcatg    4080
ccatccgtaa gatgcttttc tgtgactggt gagtactcaa ccaagtcatt ctgagaatag    4140
tgtatgcggc gaccgagttg ctcttgcccg gcgtcaatac gggataatac cgcgccacat    4200
```

```
agcagaactt taaaagtgct catcattgga aaacgttctt cggggcgaaa actctcaagg    4260
atcttaccgc tgttgagatc cagttcgatg taacccactc gtgcacccaa ctgatcttca    4320
gcatctttta ctttcaccag cgtttctggg tgagcaaaaa caggaaggca aaatgccgca    4380
aaaaagggaa taagggcgac acggaaatgt tgaatactca tactcttcct ttttcaatat    4440
tattgaagca tttatcaggg ttattgtctc atgagcggat acatatttga atgtatttag    4500
aaaaataaac aaatagggt tccgcgcaca tttccccgaa aagtgccacc tgacgtctaa    4560
gaaaccatta ttatcatgac attaacctat aaaaataggc gtatcacgag gccctttcgt    4620
ctcgcgcgtt tcggtgatga cggtgaaaac ctctgacaca tgcagctccc ggagacggtc    4680
acagcttgtc tgtaagcgga tgccgggagc agacaagccc gtcagggcgc gtcagcgggt    4740
gttggcgggt gtcggggctg gcttaactat gcggcatcag agcagattgt actgagagtg    4800
caccatatgc ggtgtgaaat accgcacaga tgcgtaagga gaaataccg catcaggaaa    4860 ttgtaaacgt taatattttg ttaaaattcg cgttaaattt ttgttaaatc agctcatttt    4920
ttaaccaata ggccgaaatc ggcaaaatcc cttataaatc aaaagaatag accgagatag    4980
ggttgagtgt tgttccagtt tggaacaaga gtccactatt aaagaacgtg gactccaacg    5040
tcaaagggcg aaaaccgtc tatcagggcg atggcccact acgtgaacca tcaccctaat    5100 caagttttt ggggtcgagg tgccgtaaag cactaaatcg aaccctaaa gggagccccc    5160 gatttagagc ttgacgggga aagccggcga acgtggcgag aaaggaaggg aagaaagcga    5220
aaggagcggg cgctagggcg ctggcaagtg tagcggtcac gctgcgcgta accaccacac    5280
ccgccgcgct taatgcgccg ctacagggcg cgtcgcgcca ttcgccattc aggctacgca    5340
actgttggga agggcgatcg gtgcgggcct cttcgctatt acgccaggct gca           5393
```